US012778928B2

(12) United States Patent
Hwang et al.

(10) Patent No.: US 12,778,928 B2
(45) Date of Patent: Nov. 3, 2026

(54) ANTI-INFLAMMATORY COMPOSITION COMPRISING BENZOFURAN-BASED N-ACYLHYDRAZONE DERIVATIVES

(71) Applicant: KOREA RESEARCH INSTITUTE OF BIOSCIENCE AND BIOTECHNOLOGY, Daejeon (KR)

(72) Inventors: Joon Sung Hwang, Daejeon (KR); Bo Yeon Kim, Daejeon (KR); Nak Kyun Soung, Daejeon (KR); Kyung Ho Lee, Daejeon (KR); Seung Cheol Lee, Daejeon (KR); Hyun Joo Cha, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 761 days.

(21) Appl. No.: 18/017,339

(22) PCT Filed: Jul. 21, 2021

(86) PCT No.: PCT/KR2021/009447

§ 371 (c)(1),
(2) Date: Jan. 20, 2023

(87) PCT Pub. No.: WO2022/019663

PCT Pub. Date: Jan. 27, 2022

(65) Prior Publication Data

US 2023/0293487 A1 Sep. 21, 2023

(30) Foreign Application Priority Data

Jul. 22, 2020 (KR) ........................ 10-2020-0091182
Jan. 12, 2021 (KR) ........................ 10-2021-0004150

(51) Int. Cl.
*A61K 31/404* (2006.01)
*A61P 29/00* (2006.01)

(52) U.S. Cl.
CPC ............ *A61K 31/404* (2013.01); *A61P 29/00* (2018.01)

(58) Field of Classification Search
CPC ...... A61K 31/404; A61K 31/405; A61K 8/49; A61K 8/4973; A61P 29/00; A23K 20/111; A23K 20/121; A23K 20/137; A23K 20/132; A23L 33/10; A61Q 19/00; A23V 2002/00; A23V 2200/324; A23V 2250/30
See application file for complete search history.

(56) References Cited

U.S. PATENT DOCUMENTS

2002/0091148 A1 7/2002 BaMaung et al.
2002/0128292 A1 9/2002 Cai et al.

FOREIGN PATENT DOCUMENTS

WO WO-2013/032907 A1 3/2013

OTHER PUBLICATIONS

Freire et al (Periodontol 2000, 2013; 63(1): 149-164) (Year: 2013).*
Patil et al (Int. J. Mol. Sci., 2019; 20:4367 pp. 1-38) (Year: 2019).*
Prescott et al (Cells, 2018; 7:115 pp. 1-34) (Year: 2018).*
Tabas et al (Science, 2013; 339(6116): 166-172) (Year: 2013).*
Chemical Abstract Compound, STN express. RN 2220348-97-8 (Apr. 27, 2018).
Chemical Abstract Compound, STN express. RN 444671-24-3 (Aug. 22, 2002), RN 444292-03-9 (Aug. 20, 2002).
Zhang et al., "Discovery of Novel Small-Molecule Inhibitors of NF-κB Signaling with Antiinflammatory and Anticancer Properties," J. Med. Chem. 61:5881-5899 (2018).
Goldminz et al., "NF-κB: An Essential Transcription Factor in Psoriasis," Journal of Dermatological Science 69 (2013) pp. 89-94.
Numomura et al., "Periostin Activates Distinct Modules of Inflammation and Itching Downstream of the Type 2 Inflammation Pathway", (2023).
Guo et al., "Signaling Pathways and Targeted Therapies for Psoriasis", Signal Transduction and Targeted Therapy (2023)8:437.

* cited by examiner

*Primary Examiner* — Rayna Rodriguez
(74) *Attorney, Agent, or Firm* — MARSHALL, GERSTEIN & BORUN LLP

(57) ABSTRACT

A pharmaceutical composition for preventing or treating an inflammatory disease, comprising a benzofuran-based N-acylhydrazone compound, a stereoisomer thereof, or a pharmaceutically acceptable salt thereof. This benzofuran-based N-acylhydrazone compound inhibits the activity of NF-κB, which is a major signal transmitter in the inflammatory response, thereby disrupting the initial pathway and process of the biological inflammatory response system and inhibiting inflammatory immune cells and inflammatory cytokines, and thus can prevent and treat various pathological diseases caused by the inflammatory response.

3 Claims, 8 Drawing Sheets

【Fig.1】
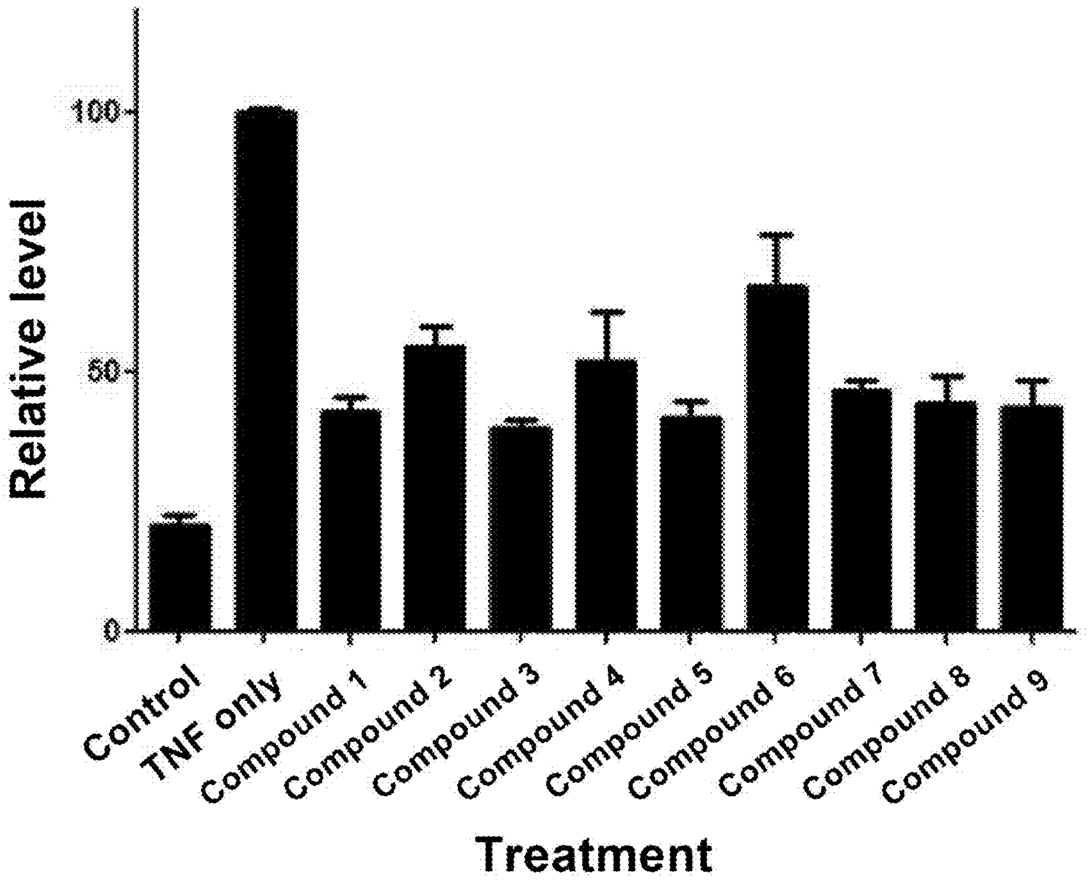

【Fig.2】
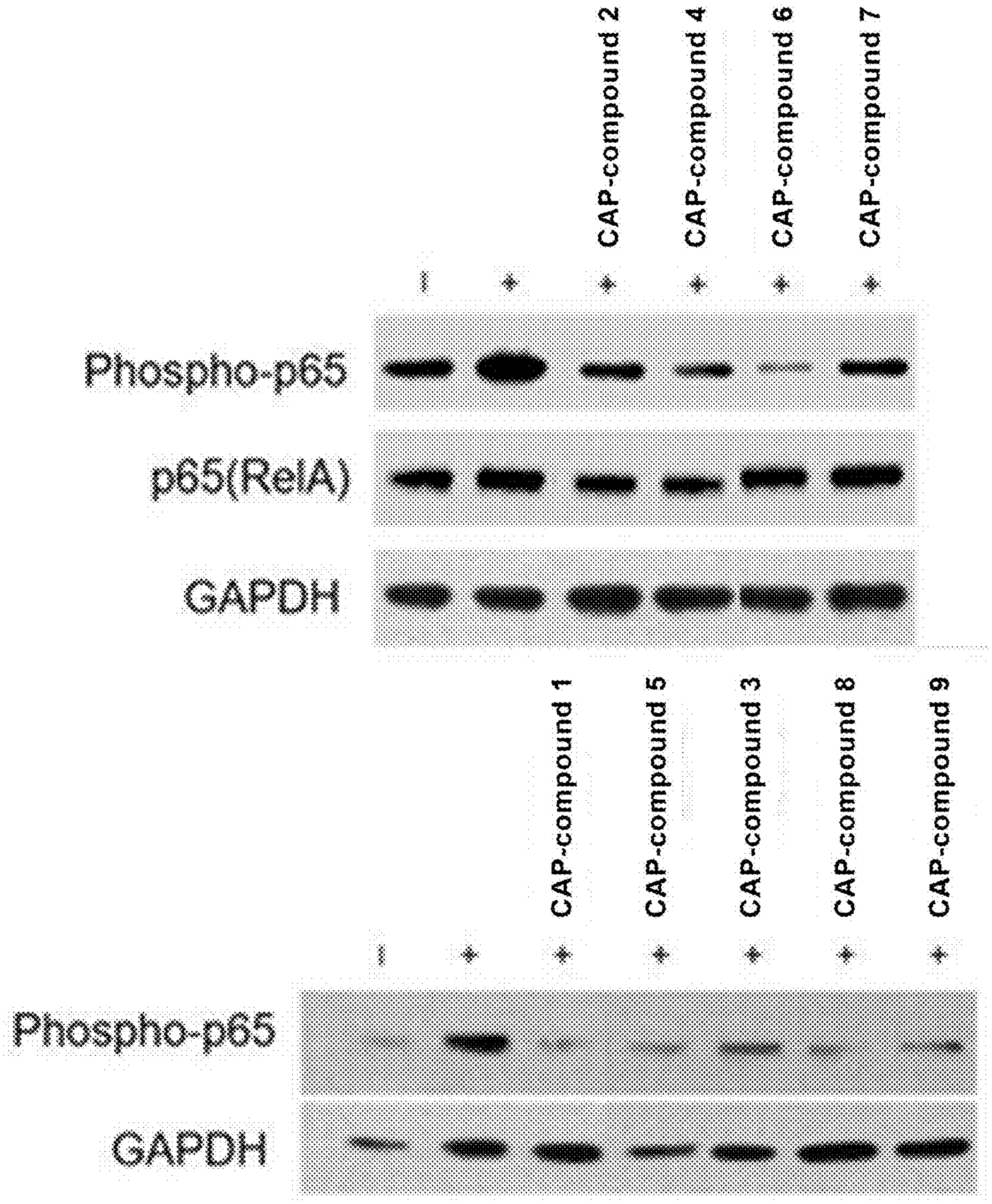

【Fig.3】
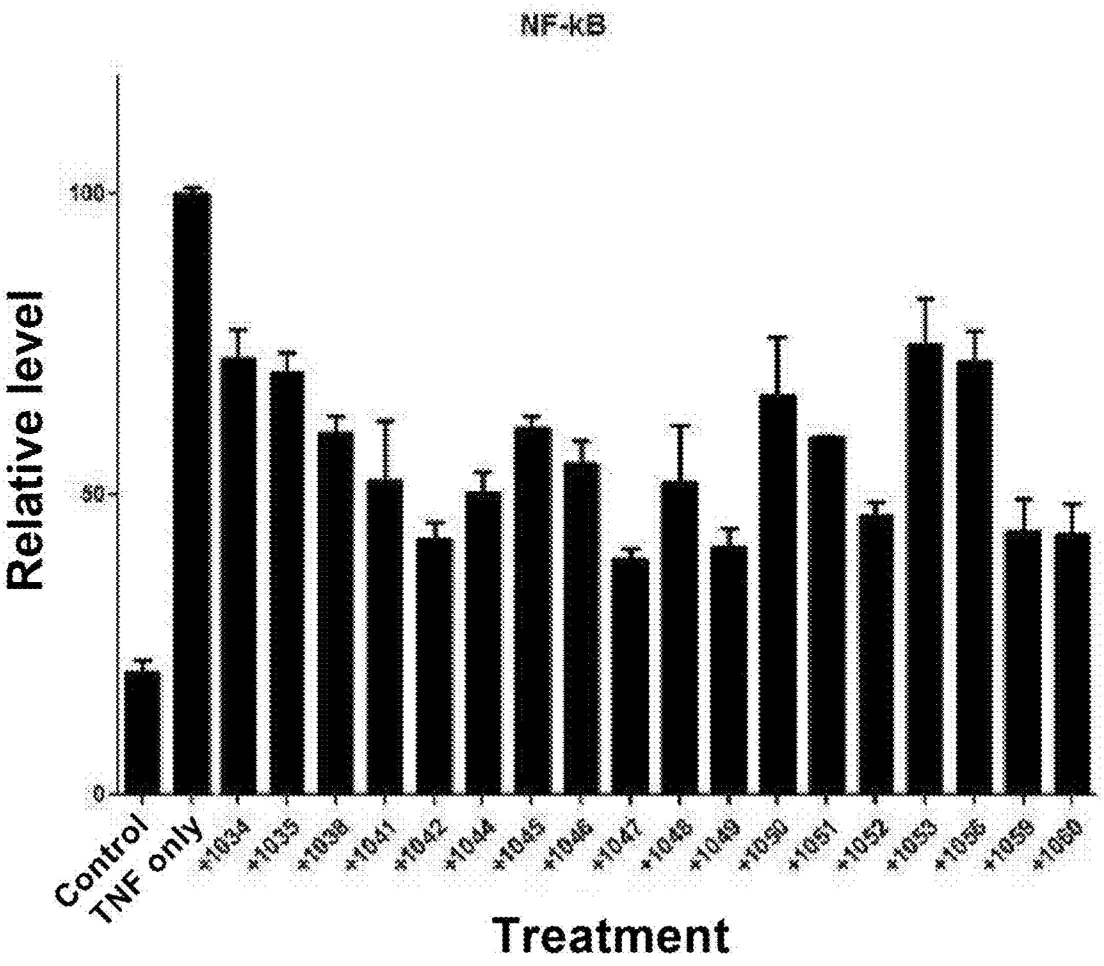

【Fig.4】
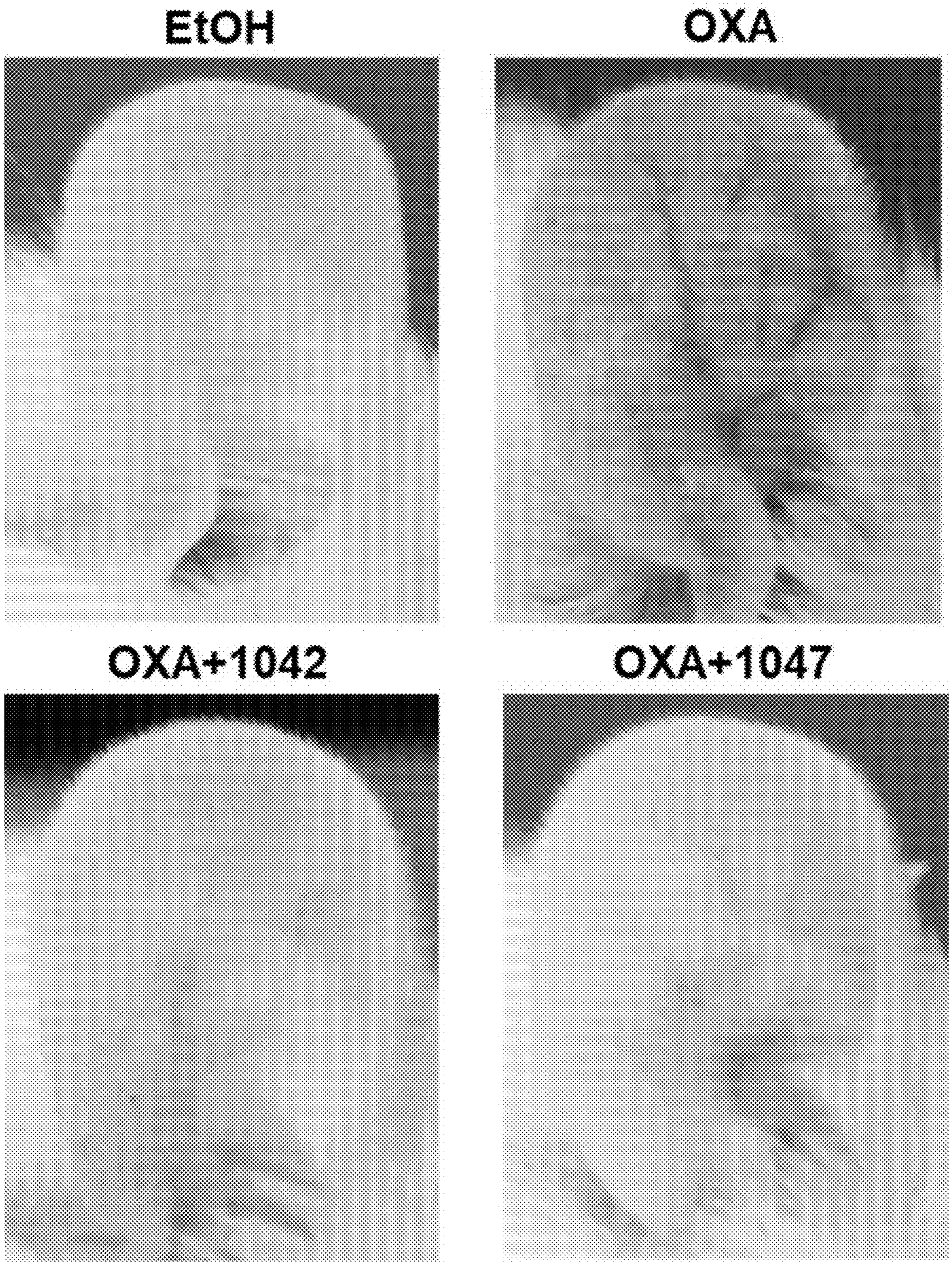

【Fig.5】
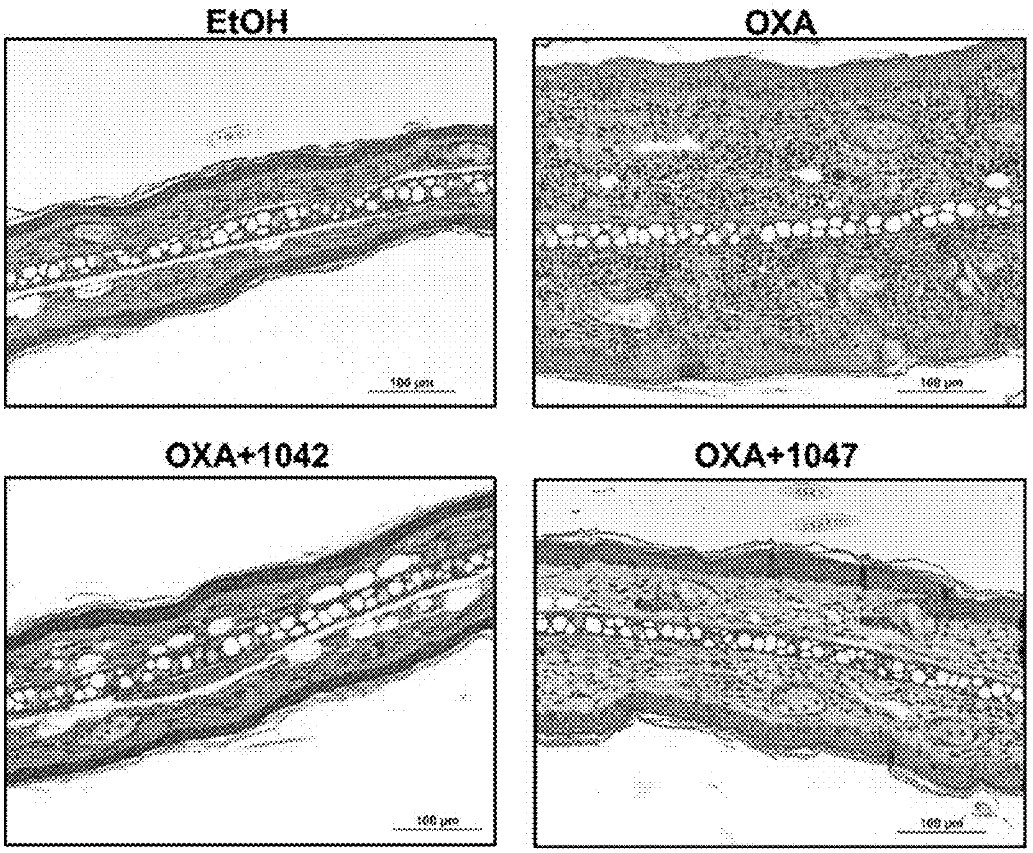
【Fig.6】
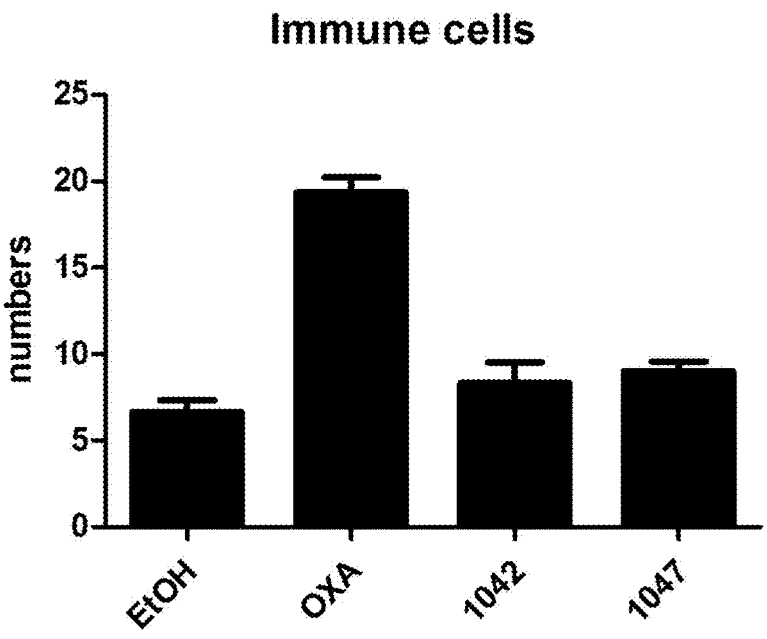

【Fig.7】
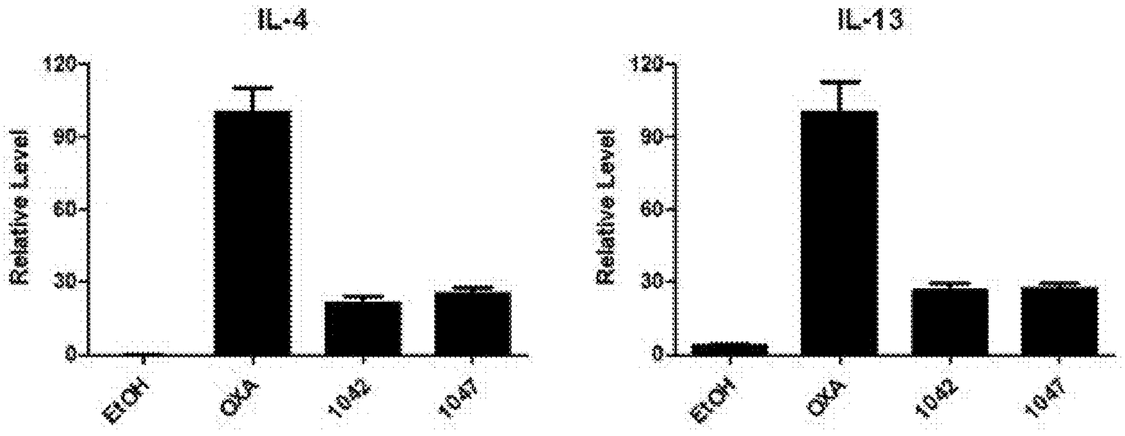
【Fig.8】
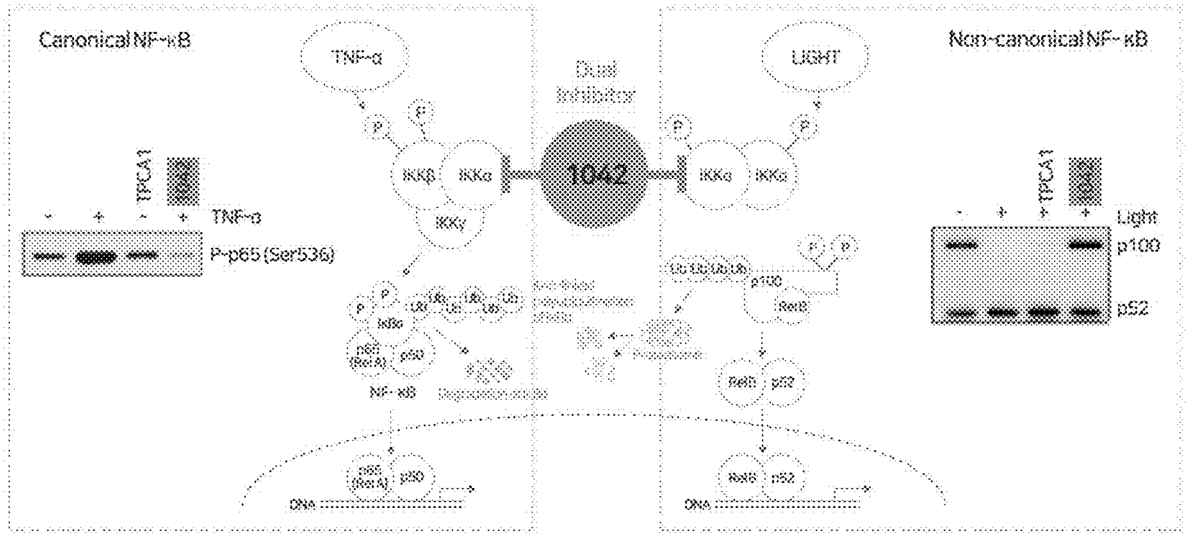

【Fig.9】
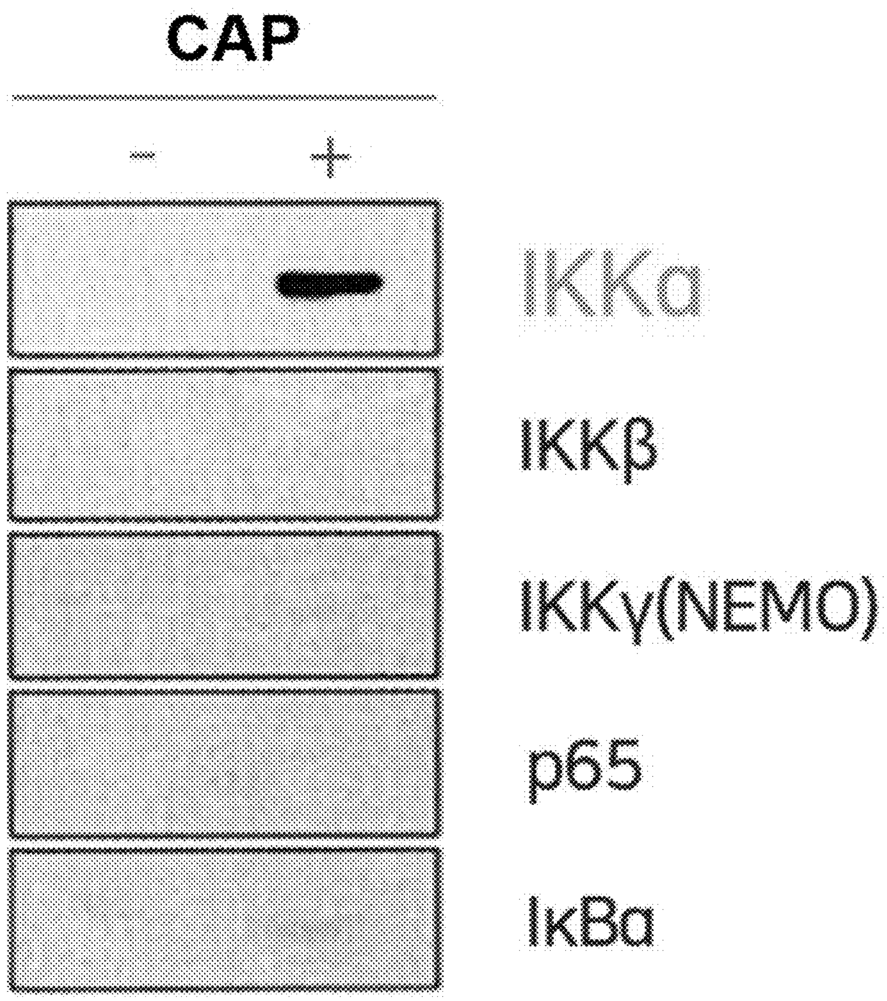
【Fig.10】
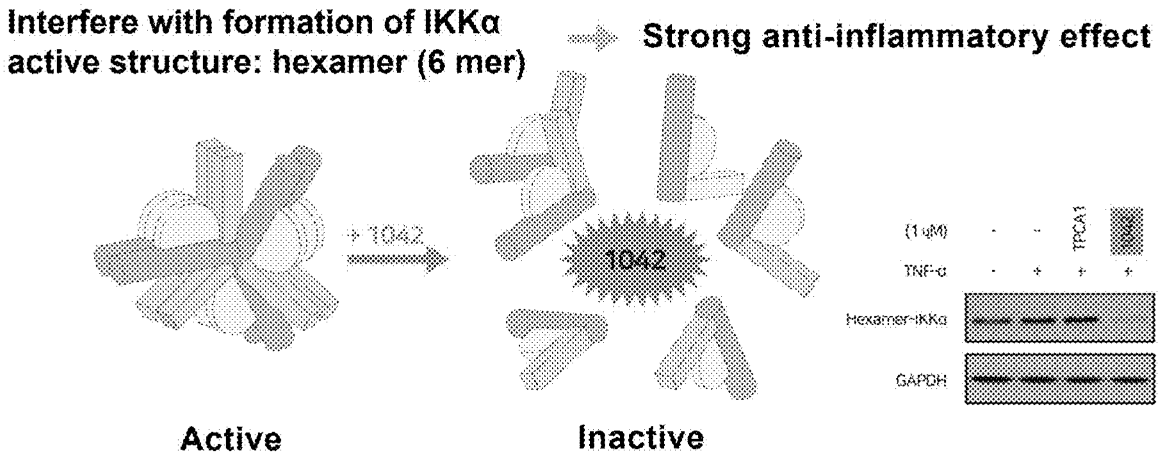

【Fig.11a】
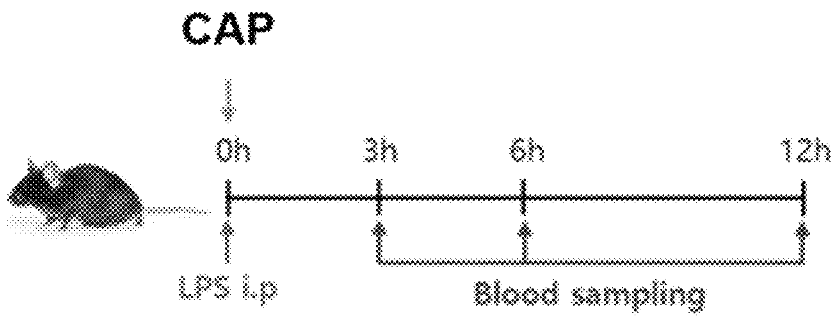
【Fig.11b】
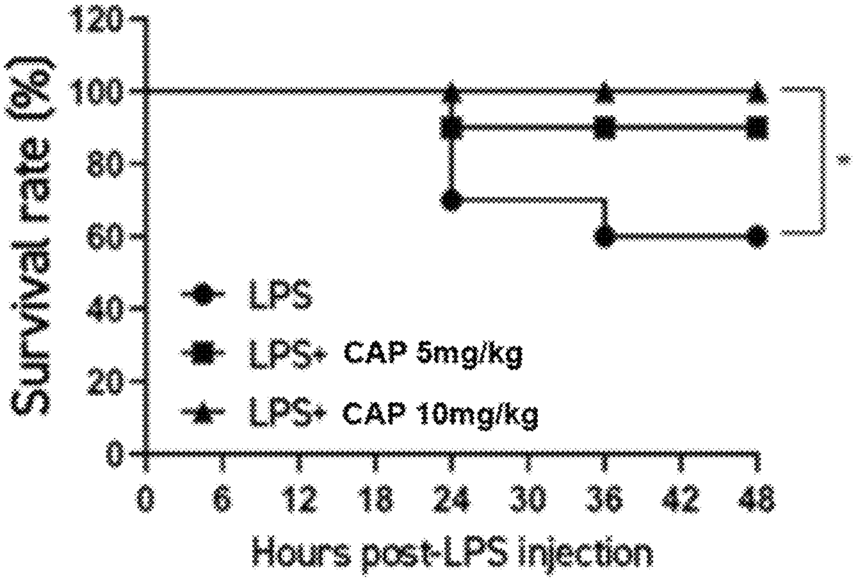
【Fig.11c】
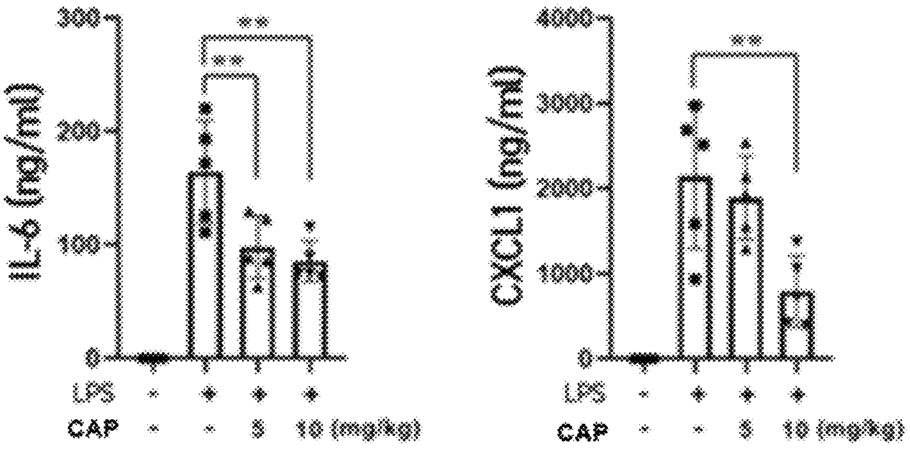

ANTI-INFLAMMATORY COMPOSITION COMPRISING BENZOFURAN-BASED N-ACYLHYDRAZONE DERIVATIVES

CROSS-REFERENCE TO RELATED APPLICATIONS

This is a U.S. National Phase of International Application No. PCT/KR2021/009447, filed Jul. 21, 2021, which claims priority to Korean Patent Application No. 10-2020-0091182, filed Jul. 22, 2020, and Korean Patent Application No. 10-2021-0004150, filed Jan. 12, 2021.

TECHNICAL FIELD

The present disclosure relates to an anti-inflammatory composition comprising a benzofuran-based N-acylhydrazone derivative, and specifically, to a compound having an inhibitory effect on an inflammatory response regulatory pathway that may be associated with NF-κB.

BACKGROUND ART

In normal cases, the inflammation neutralizes or removes onset factors through an inflammatory reaction in vivo and regenerates damaged tissue to restore normal structures and functions, but becomes a problem when the degree of inflammation exceeds a certain level or becomes chronic and progresses to a disease state such as chronic inflammation. An inflammatory response may be observed in almost all of the clinical diseases.

NF-κB is a transcriptional protein that regulates various signal transductions related to inflammatory response, immune function, aging, tumors, and the like, and has been identified in a wide range of organisms from drosophila to mammals. There are about 60 target genes of NF-κB known to date, which have been studied to play a pivotal role in various reactions. Therefore, the activity of NF-κB may be regulated to selectively control the initial pathway and process of various reactions and used as an indicator for disease treatment.

The proper balance of activation and inactivation of NF-κB helps to maintain homeostasis in the body, but when excessive activation of NF-κB initiates an inflammatory response, the production of inflammatory prostaglandins, eicosanoids, and nitric oxide is abnormally increased. This causes the body's immune response to continue excessively, induces aging, tumor onset, proliferation, and metastasis, and is related to various pathological conditions including arteriosclerosis and tissue transplant host response, and the like. In particular, the NF-κB is highly related to chronic inflammatory diseases.

In previous studies, NF-κB has been reported in a number of studies as an inflammatory transcription factor for regulating the expression of various inflammatory genes. NF-κB is highly directly related to cytokine storm or cytokine release syndrome by the activity, and is known as a therapeutic target factor for these diseases.

"Cytokine storm" or "cytokine release syndrome" is associated with a variety of conditions including infectious diseases, non-infectious diseases, autoimmune reactions, and drug side effects. Inflammation is part of the complex biological response of body tissues to harmful stimuli such as viruses, damaged cells or irritants. It is a protective response involving the immune system, blood vessels and numerous proteins. The purpose of inflammation is to eliminate the initial cause of cell damage, remove dead and dying cells, and initiate tissue repair. Under normal circumstances, inflammation has a short lifespan and the damaged tissue usually begins to repair 2-3 days after symptom onset. In the inflammatory hyperreaction, when high levels of proinflammatory proteins (cytokines) are released, blood vessels in the lungs and other tissues are damaged, resulting in a cytokine storm or cytokine release syndrome, and the inflammatory response at this time induces the deterioration of the function of each body organ.

The function of NF-κB as a key regulator of cytokine storm or cytokine release syndrome has been reported a lot, and in particular, the role of NF-κB in infectious diseases is recognized as important. Infections caused by viruses or the like induce cell death and subsequent activation of macrophages, leading to ROS production, which results in epithelial cell inflammation accompanied by cytokine production and cell destruction. Proinflammatory cytokines may also be produced by secondary infected cells through activation of NF-κB, which induces transcription of various inflammatory genes, and activation of inflammation in a ROS-dependent manner, which mediates the production and secretion of cytokines. In addition, destruction of the epithelial cell barrier eventually leads to increased susceptibility to bacterial infection.

Accordingly, it has been revealed that even in relation to the recent epidemic of infectious diseases caused by Sars-Cov2, cytokine storm is known to be the main cause of death of patients dying from the viral infection, and NF-κB signaling pathway is an important inflammatory signaling pathway that causes this cytokine storm (Trends Endocrinol Metab. 2020 November; 31(11):802-803, Pablo Guisado-Vasco et al.; Front Immunol. 2020 Dec. 10; 11:598444., Ralf Kircheis et al.).

Therefore, it is required to develop a novel compound having the effect capable of preventing and treating various pathological diseases caused by inflammatory reactions by regulating NF-κB, which is a major signal transmitter in the inflammatory response, to disrupt the initial pathway and process of the biological inflammatory response system.

Under this background, the present inventors confirmed that benzofuran-based N-acylhydrazone-based compounds as novel compounds having high stability and solubility in the body, regulated NF-κB, a major signal transmitter in the inflammatory response, to disrupt the initial pathway and process of the biological inflammatory response system, thereby preventing and treating various pathological diseases caused by inflammatory response, and completed the present disclosure.

DISCLOSURE

Technical Problem

An object of the present disclosure is to provide a pharmaceutical composition for preventing or treating an inflammatory disease, comprising a benzofuran-based N-acylhydrazone compound, a stereoisomer thereof, or a pharmaceutically acceptable salt thereof.

In addition, another object of the present disclosure is to provide a food composition, a feed composition or health functional food, for preventing or improving an inflammatory disease, comprising a benzofuran-based N-acylhydrazone compound, a stereoisomer thereof or a pharmaceutically acceptable salt thereof.

Still another object of the present disclosure is to provide a cosmetic composition for relieving skin irritation and/or skin inflammation, comprising a benzofuran-based N-acylhydrazone compound, a stereoisomer thereof or a pharmaceutically acceptable salt thereof.

Technical Solution

In one general aspect, the present disclosure provides a pharmaceutical composition for preventing or treating an inflammatory disease, comprising a compound represented by the following Chemical Formula 1, a stereoisomer thereof, or a pharmaceutically acceptable salt thereof:

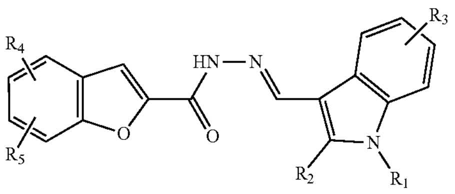

in Chemical Formula 1, $R_1$ is H, $C_{1-6}$alkyl, $C_{1-3}$alkoxycarbonyl$C_{1-3}$alkyl, or $C_{1-6}$alkoxy$C_{1-3}$alkyl;

$R_2$ is halogen, $C_{1-6}$alkyl or halo$C_{1-6}$alkyl;

$R_3$ is H, halogen, $C_{1-6}$alkyl, $C_{1-6}$alkoxy, or halo$C_{1-6}$alkoxy; and $R_4$ and $R_5$ are each independently H, halogen, $C_{1-6}$alkyl, $C_{1-6}$alkoxy, or $C_{1-6}$ alkylcarbonylamino.

The $C_{1-6}$alkyl may include $C_{1-3}$alkyl, $C_{3-6}$alkyl, $C_{2-4}$alkyl, $C_{2-6}$alkyl, and the like.

In addition, the $C_{1-6}$alkoxy may include $C_{1-3}$alkoxy, $C_{3-6}$alkoxy, $C_{2-4}$alkoxy, $C_{2-6}$alkoxy, and the like.

Further, the halo$C_{1-6}$alkyl and halo$C_{1-6}$alkoxy may each have 1 to 10 or 1 to 3 the same or different halogens.

According to an embodiment, in Chemical Formula 1, $R_1$ is H, $—CH_3$, $—CH_2CO_2CH_2CH_3$, $—CH_2OCH_2CH_3$, $—CH_2CH_2OCH_2CH_3$ or $—CH_2CH_2OCH_3$.

According to another embodiment, in the Chemical Formula 1, $R_2$ is Cl, Br, $—CH_3$, or $—CF_3$.

According to another embodiment, in the Chemical Formula 1, $R_3$ is H, F, Cl, $—CH_3$, $—OCH_3$, or $—OCF_3$.

According to another embodiment, in the Chemical Formula 1, $R_4$ and $R_5$ are each independently H, Cl, $—CH_3$, $—OCH_3$, or $—NHCOCH_3$.

According to still another embodiment, in the Chemical Formula 1, $R_1$ is H, $—CH_3$, $—CH_2CO_2CH_2CH_3$, $—CH_2OCH_2CH_3$, $—CH_2CH_2OCH_2CH_3$ or $—CH_2CH_2OCH_3$; $R_2$ is Cl, Br, $—CH_3$ or $—CF_3$; $R_3$ is H, F, Cl, $—CH_3$, $—OCH_3$, or $—OCF_3$; and $R_4$ and $R_5$ are each independently H, Cl, $—CH_3$, $—OCH_3$, or $—NHCOCH_3$.

The compound represented by Chemical Formula 1, a stereoisomer thereof or a pharmaceutically acceptable salt thereof according to the present disclosure may regulate the activity of NF-κB, thereby disrupting the initial pathway and process of the biological inflammatory response system and regulating inflammatory immune cells and inflammatory cytokines. In particular, it is possible to exhibit the action of dual inhibition that regulates both canonical and non-canonical pathways in the regulation of NF-κB. For example, this dual inhibition may perform an inhibitory action on an acute inflammatory response such as severe cytokine release syndrome (CRS) and/or a cytokine storm, thereby exhibiting a therapeutic effect on the disease. In particular, the compound according to the present disclosure may exhibit excellent effects in the treatment of inflammatory diseases by selectively binding to IKKα, which is a main common factor in the canonical and non-canonical pathways of NF-κB inflammatory signaling pathway.

Thus, the compound represented by Chemical Formula 1, a stereoisomer thereof, or a pharmaceutically acceptable salt thereof according to the present disclosure may be usefully employed for the prevention or treatment of an inflammatory disease.

According to the present disclosure, the inflammatory disease may be any one or more selected from the group consisting of dermatitis, cytokine release syndrome (CRS), cytokine storm, allergy, nasal polyps, rhinitis, chronic sinusitis, nasal congestion, nasal itching, asthma, chronic obstructive pulmonary disease, rheumatoid arthritis, conjunctivitis, keratoconjunctivitis, ophthalmia, dry eye, heart failure, arrhythmia, atherosclerosis, multiple sclerosis, inflammatory bowel disease, inflammatory pain, neurogenic pain, osteoarthritis pain, lupus, sepsis, Crohn's disease, gout, Sjögren's syndrome, Alzheimer's disease, Parkinson's disease, thyroid autoimmune disease, multiple sclerosis, Guillain-Barré syndrome, autism, hemolytic dyslipidemia, thyroiditis, Hashimoto's disease, Graves' disease, ankylosing spondylitis, polymyalgic rheumatoiditis, celiac disease, ulcerative colitis, type 1 diabetes, peripheral neuropathy, diabetic peripheral neuropathy, Wegener's granulomatosis, muscular dystrophy, Fibromyalgia, systemic lupus erythematosus, Behcet's disease, uveitis, glomerulonephritis, Goodpasture syndrome, glandular autoimmune syndrome, Churg-Strauss syndrome, Henoch-Schonlein purpura, Polyarteritis nodosa, Takayasu's arteritis, temporal arteritis, relapsing polychondritis, alopecia areata, severe acute respiratory syndrome coronavirus 2 infection disease and narcolepsy.

According to the present disclosure, the inflammatory disease may be dermatitis.

The dermatitis may be, for example, any one or more selected from the group consisting of atopic dermatitis, contact dermatitis, allergic dermatitis, acne, eczema, rosacea, oily skin, psoriasis, eczema, prurtis, skin itching, urticaria, chronic idiopathic urticaria, systemic sclerosis, leukoplakia, scleroderma, Behcet's disease, and contact transmission impetigo.

According to the present disclosure, cytokine release syndrome (CRS) and/or cytokine storm is a type of systemic inflammatory response syndrome capable of being induced by various factors such as infection, specific drugs, and the like.

The cytokine release syndrome (CRS) and/or cytokine storm according to the present disclosure may be more specifically a cytokine release syndrome (CRS) and/or cytokine storm caused by a viral infection.

For example, the virus may be any one or more viruses selected from the group consisting of influenza virus, influenza A virus subtype H1N1, avian influenza virus, rhinovirus, adenovirus, coronavirus, MERS Corona Virus, severe acute respiratory syndrome coronavirus 2, parainfluenza virus, respiratory syncytial virus, herpesvirus (HSV), human immunodeficiency virus (HIV), and hepatitis virus.

The compound represented by Chemical Formula 1, a stereoisomer thereof or a pharmaceutically acceptable salt thereof according to the present disclosure may inhibit the cytokine storm that rapidly progresses through the action of dual inhibition that regulates both canonical and non-canonical pathways in the regulation of NF-κB, thereby exhibiting excellent effects in the treatment of diseases. In particular, the compound represented by Chemical Formula 1, a stereoisomer thereof or a pharmaceutically acceptable salt thereof according to the present disclosure may exhibit excellent treatment and improvement effects against viral infections in which acute inflammatory responses, particularly cytokine storms, are problematic, such as infection caused by severe acute respiratory syndrome coronavirus 2.

According to the present disclosure, the inflammatory disease may be sepsis.

According to the present disclosure, the inflammatory disease may be severe acute respiratory syndrome coronavirus 2 infection disease.

According to the present disclosure, the benzofuran-based N-acylhydrazone compound, a stereoisomer thereof or a pharmaceutically acceptable salt thereof may inhibit the activity of NF-κB to inhibit cytokine release syndrome (CRS) and cytokine storms or to exhibit anti-inflammatory activity. In particular, the benzofuran-based N-acylhydrazone compound, a stereoisomer thereof or a pharmaceutically acceptable salt thereof according to the present disclosure may exhibit the action of dual inhibition that regulates both canonical and non-canonical pathways in the regulation of NF-κB. Further, the benzofuran-based N-acylhydrazone compound, a stereoisomer thereof or a pharmaceutically acceptable salt thereof according to the present disclosure may selectively bind to IKKα, an important factor in the NF-κB inflammatory signaling pathway, thereby inhibiting the formation of active structures and disrupting the NF-κB signaling pathway.

According to the present disclosure, the benzofuran-based N-acylhydrazone compound, a stereoisomer thereof, or a pharmaceutically acceptable salt thereof may exhibit an anti-inflammatory activity by disrupting the phosphorylation of p65.

According to the present disclosure, the benzofuran-based N-acylhydrazone compound, a stereoisomer thereof, or a pharmaceutically acceptable salt thereof may exhibit the anti-inflammatory activity by reducing the number of inflammatory immune cells.

According to the present disclosure, the benzofuran-based N-acylhydrazone compound, a stereoisomer thereof, or a pharmaceutically acceptable salt thereof may exhibit the anti-inflammatory activity by inhibiting the expression of inflammatory cytokines.

According to the present disclosure, the benzofuran-based N-acylhydrazone compound, a stereoisomer thereof, or a pharmaceutically acceptable salt thereof may exhibit a particularly excellent anti-inflammatory effect in dermatitis by suppressing epithelial hyperplasia caused by an inflammatory response.

According to the present disclosure, the benzofuran-based N-acylhydrazone compound, a stereoisomer thereof or a pharmaceutically acceptable salt thereof may exhibit excellent effects as a therapeutic agent for sepsis by inhibiting cytokine release syndrome (CRS) and cytokine storm while simultaneously strongly suppressing the inflammatory response in the lung.

In addition, the benzofuran-based N-acylhydrazone compound, a stereoisomer thereof or a pharmaceutically acceptable salt thereof according to the present disclosure may have excellent anti-inflammatory effects together with inhibition of cytokine release syndrome (CRS) and cytokine storm, thereby exhibiting an excellent therapeutic effect for severe acute respiratory syndrome coronavirus 2 infection disease which has problems with cytokine storm and strong inflammatory response in the lung.

In addition, the present disclosure provides a food composition, a feed composition or health functional food, for preventing or improving an inflammatory disease, comprising the benzofuran-based N-acylhydrazone compound represented by Chemical Formula 1, a stereoisomer thereof or a pharmaceutically acceptable salt thereof.

In addition, the present disclosure provides a cosmetic composition for preventing or improving dermatitis, comprising the benzofuran-based N-acylhydrazone compound represented by Chemical Formula 1, a stereoisomer thereof or a pharmaceutically acceptable salt thereof.

Further, the present disclosure provides a cosmetic composition for relieving skin irritation and/or skin inflammation, comprising the benzofuran-based N-acylhydrazone compound represented by Chemical Formula 1, a stereoisomer thereof or a pharmaceutically acceptable salt thereof.

Advantageous Effects

The benzofuran-based N-acylhydrazone compound according to the present disclosure may inhibit the activity of NF-κB, which is a major signal transmitter in the inflammatory response, to disrupt the initial pathway and process of the biological inflammatory response system and to inhibit inflammatory immune cells and inflammatory cytokines, thereby being usefully employed as a pharmaceutical composition, food composition, feed composition, health functional food or cosmetic composition capable of preventing and treating various pathological diseases caused by the inflammatory response.

DESCRIPTION OF DRAWINGS

FIG. 1 shows results of the inflammatory response inhibitory efficacy through the NF-κB reporter assay for compounds of Examples according to the present disclosure.

FIG. 2 shows results of the NF-κB signal pathway inhibitory effect of the compounds of Examples according to the present disclosure.

FIG. 3 shows results confirming that the compounds of Examples according to the present disclosure inhibit the expression of related factors in the NF-κB pathway.

FIG. 4 shows visual results of inflammation inhibitory effect confirmed with the naked eye by treating dermatitis-induced models with the compounds of Examples according to the present disclosure.

FIG. 5 shows H&E staining results of epithelial hyperplasia suppressed by treating the dermatitis-induced models with the compounds of Examples according to the present disclosure.

FIG. 6 shows results confirming that the number of inflammatory immune cells is reduced by treating the dermatitis-induced models with the compounds of Examples according to the present disclosure.

FIG. 7 shows results confirming that the expression of inflammatory cytokines is reduced by treating the dermatitis-induced models with the compounds of Examples according to the present disclosure.

FIG. 8 shows results confirming that the compounds of Examples according to the present disclosure regulate both canonical and non-canonical pathways.

FIG. 9 shows results confirming that the compound of Example according to the present disclosure selectively bound to IKKα.

FIG. 10 shows results confirming that the compounds of Examples according to the present disclosure inhibit the formation of hexamer IKKα.

FIG. 11 shows results of confirming the effect of the compounds of Examples according to the present disclosure on inhibiting the mortality due to sepsis and on inhibiting the expression of inflammatory cytokines and chemokines in a cytokine storm model (based on a sepsis model).

BEST MODE

Hereinafter, the present disclosure will be described in more detail.

In the present specification, the term "halogen" means F, Cl, Br or I unless otherwise specified.

The term "alkyl," unless otherwise specified, refers to a linear or branched saturated hydrocarbon moiety. For example, "C1-6alkyl" refers to alkyl having a backbone comprising 1 to 6 carbon atoms. Specifically, C1-6alkyl may include methyl, ethyl, n-propyl, i-propyl, n-butyl, i-butyl, t-butyl, n-pentyl, i-pentyl, t-pentyl, sec-pentyl, neopentyl, hexyl; and the like.

The term "alkoxy", unless otherwise specified, refers to a linear or branched alkyl-oxy moiety. For example, "C1-6alkoxy" refers to alkyl-oxy having a backbone comprising 1 to 6 carbons. Specifically, C1-6alkoxy may include methoxy, ethoxy, n-propoxy, i-propoxy, n-butoxy, i-butoxy, t-butoxy, n-pentoxy, i-pentoxy, t-pentoxy, sec-pentoxy, neopentoxy, hexyloxy, and the like.

The term "haloalkyl" or "haloalkoxy" means an alkyl or alkoxy substituted with one or more halogens. Specifically, haloalkyl or haloalkoxy may be alkyl or alkoxy in which one or more homogeneous or heterogeneous halogens are substituted.

The term "substitution" refers to the replacement of a hydrogen atom in a molecular structure with a substituent so as to form a compound that is chemically stable from this substitution without exceeding the valence on the designated atom. For example, "Group A is substituted with substituent B" may indicate that a hydrogen atom bonded to an atom such as carbon constituting the backbone of Group A is replaced with the substituent B, thereby forming a covalent bond between group A and substituent B.

The present disclosure provides a pharmaceutical composition for preventing or treating an inflammatory disease, comprising a compound represented by the following Chemical Formula 1, a stereoisomer thereof, or a pharmaceutically acceptable salt thereof:

[Chemical Formula 1]

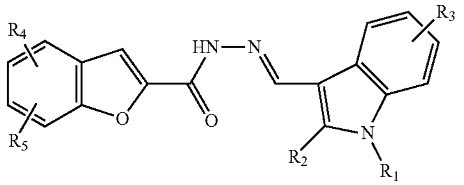

in Chemical Formula 1, $R_1$ is H, $C_{1-6}$alkyl, $C_{1-6}$alkoxycarbonyl$C_{1-3}$alkyl, or $C_{1-6}$alkoxy$C_{1-3}$alkyl;

$R_2$ is halogen, $C_{1-6}$alkyl or halo$C_{1-6}$alkyl;

$R_3$ is H, halogen, $C_{1-6}$alkyl, $C_{1-6}$alkoxy, or halo$C_{1-6}$alkoxy; and $R_4$ and $R_5$ are each independently H, halogen, $C_{1-6}$alkyl, $C_{1-6}$alkoxy, or $C_{1-6}$ alkylcarbonylamino.

The $C_{1-6}$alkyl may include $C_{1-3}$alkyl, $C_{3-6}$alkyl, $C_{2-4}$alkyl, $C_{2-6}$alkyl, and the like.

In addition, the $C_{1-6}$alkoxy may include $C_{1-6}$alkoxy, $C_{3-6}$alkoxy, $C_{2-4}$alkoxy, $C_{2-6}$alkoxy, and the like.

Further, the halo$C_{1-6}$alkyl and the halo$C_{1-6}$alkoxy may each have 1 to 10, or 1 to 3, of the same or different halogens.

According to an embodiment, in Chemical Formula 1, $R_1$ is $—CH_3$, $—CH_2CO_2CH_2CH_3$, $—CH_2OCH_2CH_3$, $—CH_2CH_2OCH_2CH_3$ or $—CH_2CH_2OCH_3$.

According to another embodiment, in Chemical Formula 1, $R_2$ is Cl, Br, $—CH_3$, or $—CF_3$.

According to still another embodiment, in Chemical Formula 1, $R_3$ is H, F, Cl, $—CH_3$, $—OCH_3$, or $—OCF_3$.

According to another embodiment, in Chemical Formula 1, $R_4$ and $R_5$ are each independently H, Cl, $—CH_3$, $—OCH_3$, or $—NHCOCH_3$.

According to still another embodiment, in Chemical Formula 1, $R_1$ is H, $—CH_3$, $—CH_2CO_2CH_2CH_3$, $—CH_2OCH_2CH_3$, $—CH_2CH_2OCH_2CH_3$ or $—CH_2CH_2OCH_3$; $R_2$ is Cl, Br, $—CH_3$ or $—CF_3$; $R_3$ is H, F, Cl, $—CH_3$, $—OCH_3$, or $—OCF_3$; and $R_4$ and $R_5$ are each independently H, Cl, $—CH_3$, $—OCH_3$, or $—NHCOCH_3$.

Specific examples of the compound represented by Chemical Formula 1 are as follows:

1(compound 7). (E)-N'-[(2-chloro-1H-indol-3-yl)methylene]-5-methylbenzofuran-2-carbohydrazide;

2(compound 13). (E)-N'-[(2-chloro-1-methyl-1H-indol-3-yl)methylene]-5-methylbenzofuran-2-carbohydrazide;

3(compound 12). Ethyl (E)-2-{2-chloro-3-[(2-(5-methylbenzofuran-2-carbonyl)hydrazinylidene)methyl]-1H-indol-1-yl}acetate;

4(compound 1). (E)-N'-[(2-chloro-1-(2-ethoxyethyl)-1H-indol-3-yl]methylene}-5-methylbenzofuran-2-carbohydrazide;

5(compound 14). (E)-N'-[(2-bromo-1-(2-ethoxyethyl)-1H-indol-3-yl]methylene}-5-methylbenzofuran-2-carbohydrazide;

6(compound 15). (E)-N'-{[1-(2-ethoxyethyl)-2-(trifluoromethyl)-1H-indol-3-yl]methylene}-5-methylbenzofuran-2-carbohydrazide;

7(compound 19). (E)-N'-[(2-chloro-1-(2-methoxyethyl)-1H-indol-3-yl]methylene}-5-methylbenzofuran-2-carbohydrazide;

8(compound 2). (E)-N'-[(2-chloro-1-(2-ethoxyethyl)-5-methoxy-1H-indol-3-yl]methylene}-5-methylbenzofuran-2-carbohydrazide;

9(compound 6). (E)-N'-[(2-chloro-1-(2-ethoxyethyl)-6-methoxy-1H-indol-3-yl]methylene}-5-methylbenzofuran-2-carbohydrazide;

10(compound 5). (E)-N'-[(2-chloro-1-(2-ethoxyethyl)-5-fluoro-1H-indol-3-yl]methylene}-5-methylbenzofuran-2-carbohydrazide;

11(compound 9). (E)-N'-{[2,5-dichloro-1-(2-ethoxyethyl)-1H-indol-3-yl]methylene}-5-methylbenzofuran-2-carbohydrazide;

12(compound 3). (E)-N'-{[2-chloro-1-(2-ethoxyethyl)-5-(trifluoromethoxy)-1H-indol-3-yl]methylene}-5-methylbenzofuran-2-carbohydrazide;

13(compound 8). (E)-N'-[(2-chloro-1-(2-ethoxyethyl)-5-methyl-1H-indol-3-yl]methylene}-5-methylbenzofuran-2-carbohydrazide;

14(compound 16). (E)-N'-[(2-chloro-1-(2-ethoxyethyl)-1H-indol-3-yl]methylene}-5-methoxybenzofuran-2-carbohydrazide;

15(compound 17). (E)-N'-[(2-chloro-1-(2-ethoxyethyl)-5-methoxy-1H-indol-3-yl]methylene}-5-methoybenzofuran-2-carbohydrazide;

16(compound 20). (E)-5-chloro-N'-{[2-chloro-1-(2-ethoxyethyl)-1H-indol-3-yl]methylene}benzofuran-2-carbohydrazide;

17(compound 21). (E)-N'-{[2-chloro-1-(2-ethoxyethyl)-1H-indol-3-yl]methylene}-4,7-dimethylbenzofuran-2-carbohydrazide;

18(compound 22). (E)-N'-[(2-chloro-1-(2-ethoxyethyl)-1H-indol-3-yl]methylene}-4,6-dimethoxybenzofuran-2-carbohydrazide;

19(compound 18). (E)-N'-{2-[2-((2-chloro-1-(2-ethoxy-ethyl)-1H-indol-3-yl)methylene]hydrazine-1-carbonyl}benzofuran-5-yl)acetamide;

20(compound 23). (E)-ethyl-2-(3-((2-(4,6-dimethoxybenzofuran-2-carbonyl)hydrazinylidene)methyl)-2-methyl-1H-indol-1-yl)acetate;

21(compound 10). Ethyl (E)-2-(2-methyl-3-((2-(5-methylbenzofuran-2-carbonyl)hydrazinylidene)methyl)-1H-indol-1-yl)acetate;

22(compound 11). Ethyl (E)-2-(3-((2-(5-chlorobenzofuran-2-carbonyl)hydrazinylidene)methyl)-2-methyl-1H-indol-1-yl-acetate; and 23(compound 4). Methyl (E)-2-(2-chloro-3-((2-(5-methylbenzofuran-2-carbonyl)hydrazinylidene)methyl)-1H-indol-1-yl)acetate.

The structural formulas of the compounds (based on compound Nos.) are shown in Table below:

| No | Structural Formula (Compound No.) |
|---|---|
| 1 | 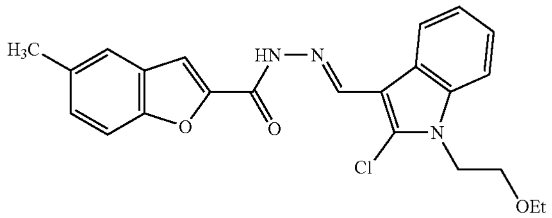 [SMILES: CCOCCn1c(Cl)c(/C=N/NC(=O)c2cc3cc(C)ccc3o2)c2ccccc21] |
| 2 | 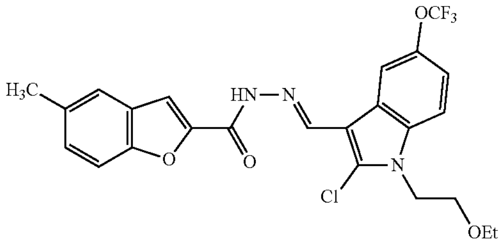 [SMILES: CCOCCn1c(Cl)c(/C=N/NC(=O)c2cc3cc(C)ccc3o2)c2cc(OC(F)(F)F)ccc21] |
| 3 | 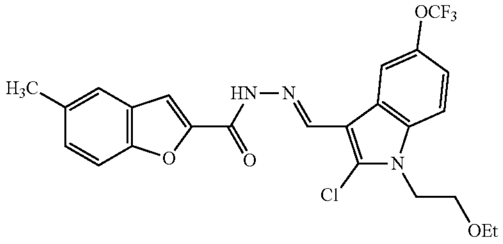 [SMILES: CCOCCn1c(Cl)c(/C=N/NC(=O)c2cc3cc(C)ccc3o2)c2cc(OC(F)(F)F)ccc21] |
| 4 | 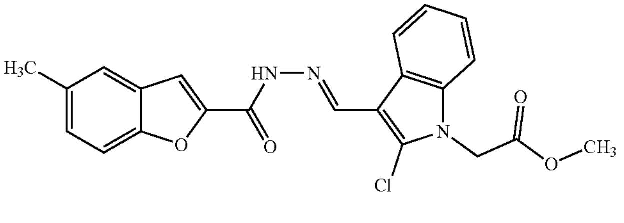 |
| 5 | 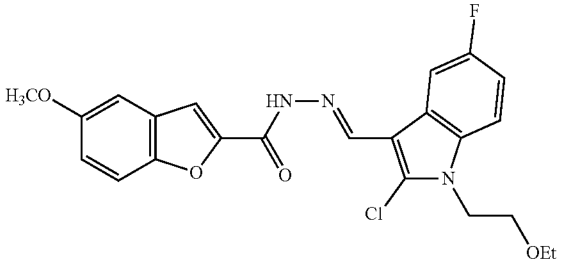 [SMILES: CCOCCn1c(Cl)c(/C=N/NC(=O)c2cc3cc(OC)ccc3o2)c2cc(F)ccc21] |

-continued
| No | Structural Formula (Compound No.) |
|---|---|
| 6 | 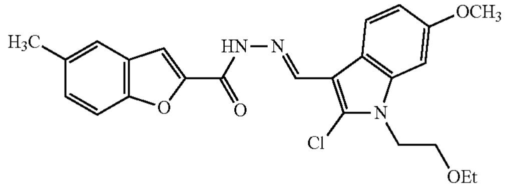 [SMILES: CCOCCn1c(Cl)c(/C=N/NC(=O)c2cc3cc(C)ccc3o2)c2ccc(OC)cc21] |
| 7 | 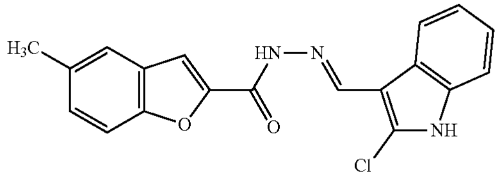 [SMILES: Cc1ccc2oc(C(=O)N/N=C/c3c(Cl)[nH]c4ccccc34)cc2c1] |
| 8 | 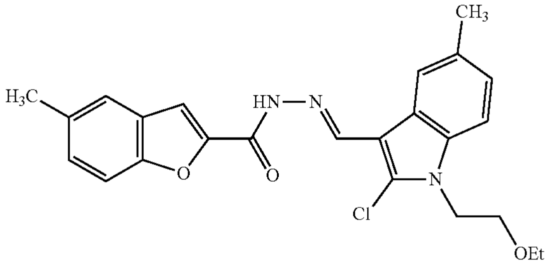 [SMILES: CCOCCn1c(Cl)c(/C=N/NC(=O)c2cc3cc(C)ccc3o2)c2cc(C)ccc21] |
| 9 | 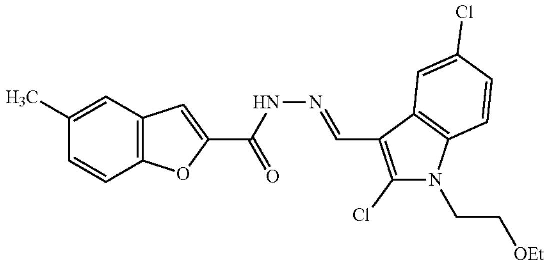 [SMILES: CCOCCn1c(Cl)c(/C=N/NC(=O)c2cc3cc(C)ccc3o2)c2cc(Cl)ccc21] |
| 10 | 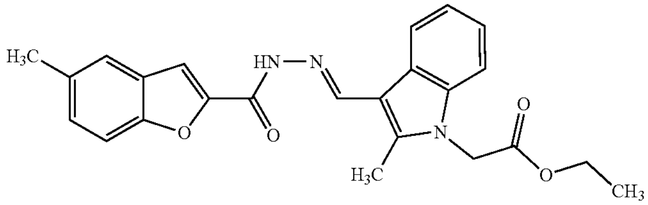 [SMILES: CCOC(=O)Cn1c(C)c(/C=N/NC(=O)c2cc3cc(C)ccc3o2)c2ccccc21] |
| 11 | 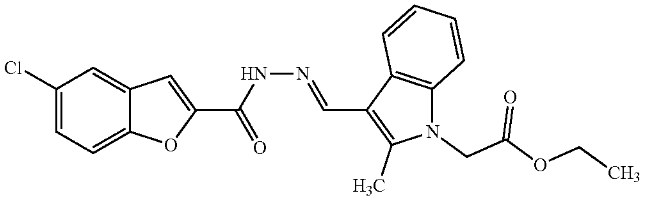 [SMILES: CCOC(=O)Cn1c(C)c(/C=N/NC(=O)c2cc3cc(Cl)ccc3o2)c2ccccc21] |
| 12 | 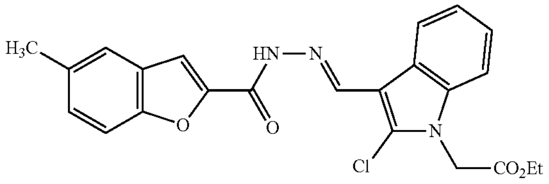 [SMILES: CCOC(=O)Cn1c(Cl)c(/C=N/NC(=O)c2cc3cc(C)ccc3o2)c2ccccc21] |

-continued
| No | Structural Formula (Compound No.) |
|---|---|
| 13 | 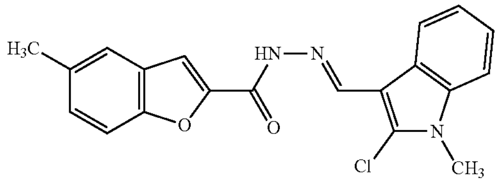 [SMILES: Cc1ccc2oc(C(=O)N/N=C/c3c(Cl)n(C)c4ccccc34)cc2c1] |
| 14 | 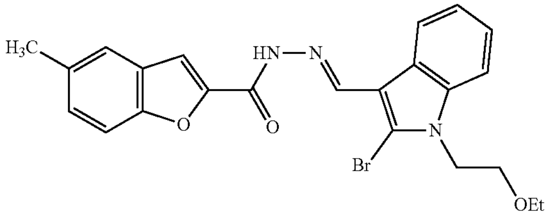 [SMILES: CCOCCn1c(Br)c(/C=N/NC(=O)c2cc3cc(C)ccc3o2)c2ccccc21] |
| 15 | 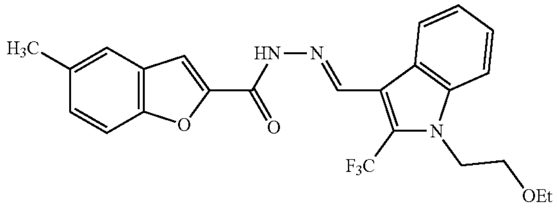 [SMILES: CCOCCn1c(C(F)(F)F)c(/C=N/NC(=O)c2cc3cc(C)ccc3o2)c2ccccc21] |
| 16 | 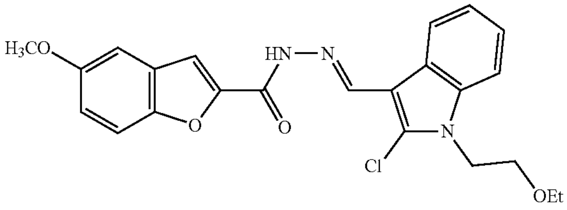 [SMILES: CCOCCn1c(Cl)c(/C=N/NC(=O)c2cc3cc(OC)ccc3o2)c2ccccc21] |
| 17 | 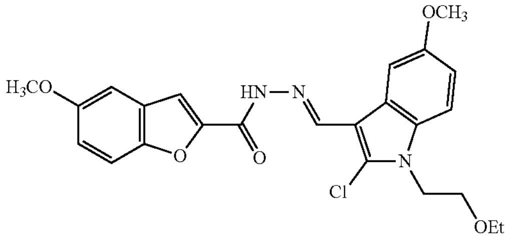 [SMILES: CCOCCn1c(Cl)c(/C=N/NC(=O)c2cc3cc(OC)ccc3o2)c2cc(OC)ccc21] |
| 18 | 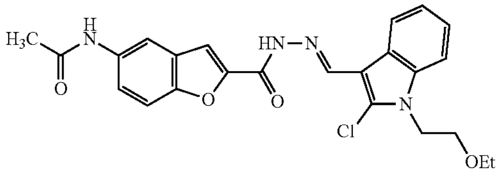 [SMILES: CCOCCn1c(Cl)c(/C=N/NC(=O)c2cc3cc(NC(C)=O)ccc3o2)c2ccccc21] |
| 19 | 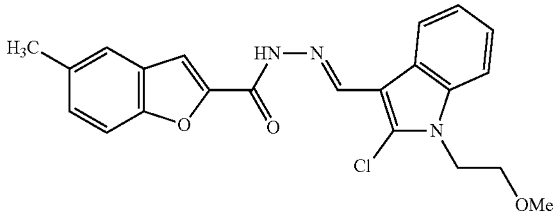 [SMILES: COCCn1c(Cl)c(/C=N/NC(=O)c2cc3cc(C)ccc3o2)c2ccccc21] |

-continued

| No | Structural Formula (Compound No.) |
|---|---|
| 20 | 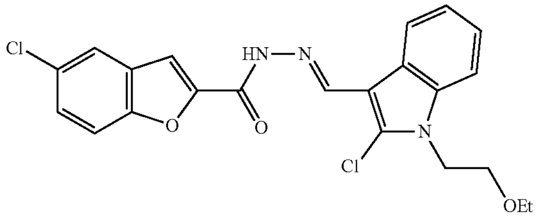 [SMILES: CCOCCn1c(Cl)c(/C=N/NC(=O)c2cc3cc(Cl)ccc3o2)c2ccccc21] |
| 21 | 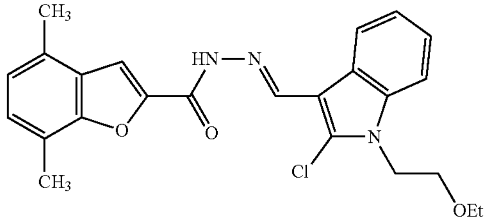 [SMILES: CCOCCn1c(Cl)c(/C=N/NC(=O)c2cc3c(C)ccc(C)c3o2)c2ccccc21] |
| 22 | 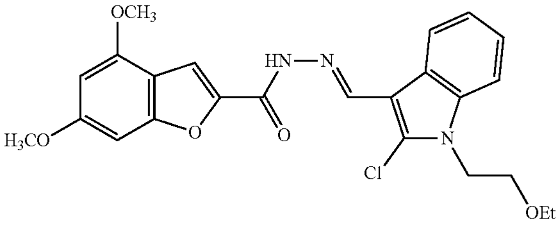 [SMILES: CCOCCn1c(Cl)c(/C=N/NC(=O)c2cc3c(OC)cc(OC)cc3o2)c2ccccc21] |
| 23 | 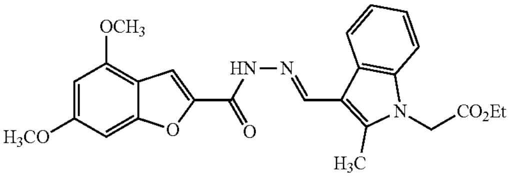 [SMILES: CCOC(=O)Cn1c(C)c(/C=N/NC(=O)c2cc3c(OC)cc(OC)cc3o2)c2ccccc21] |

More specifically, the compound represented by Chemical Formula 1 according to the present disclosure may be a compound represented by the following Chemical Formula 2:

[Chemical Formula 2]

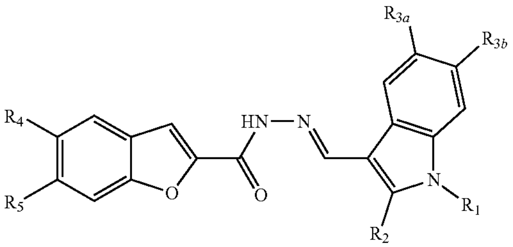

in Chemical Formula 2, $R_1$ is H, $C_{1-2}$alkyl, $C_{1-6}$alkoxycarbonyl$C_{1-3}$alkyl, or $C_{1-6}$alkoxy$C_{1-3}$alkyl;

$R_2$ is halogen, $C_{1-6}$alkyl or halo$C_{1-6}$alkyl;

$R_{3a}$ and $R_{3b}$ are both H, or when either $R_{3a}$ or $R_{3b}$ is halogen, $C_{1-6}$alkyl, $C_{1-6}$alkoxy, or halo$C_{1-6}$alkoxy, the other is H;

$R_4$ is halogen, $C_{1-6}$alkyl, $C_{1-6}$alkoxy, or $C_{1-6}$alkylcarbonylamino; and $R_5$ is H.

The substituents $R_1$, $R_2$, $R_4$, and $R_5$ are the same as defined in Chemical Formula 1.

Specific examples of $R_{3a}$ and $R_{3b}$ are each independently H, F, Cl, —$CH_3$, —$OCH_3$, or —$OCF_3$. More specifically, when either $R_{3a}$ or $R_{3b}$ is halogen, $C_{1-6}$alkyl, $C_{1-6}$alkoxy, or halo$C_{1-6}$ alkoxy, the halogen, $C_{1-6}$alkyl, $C_{1-6}$alkoxy, or halo$C_{1-6}$alkoxy is F, Cl, —$CH_3$, —$OCH_3$, or —$OCF_3$.

The present disclosure includes a pharmaceutically acceptable salt of the compound represented by Chemical Formula 1.

The pharmaceutically acceptable salt should have low toxicity to humans and should not have any negative effect on the biological activity and physicochemical properties of the parent compound.

For example, the pharmaceutically acceptable salt may be an acid addition salt formed by a pharmaceutically acceptable free acid.

The free acid may be an inorganic acid or an organic acid, wherein the inorganic acid may be hydrochloric acid, sulfuric acid, nitric acid, phosphoric acid, perchloric acid, hydrobromic acid, and the like, and the organic acid may be acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, and the like.

The acid addition salt may be prepared by a conventional method, for example, by dissolving the compound of Chemical Formula 1 in an excess of aqueous acid solution, and precipitating the salt using a water-miscible organic solvent such as methanol, ethanol, acetone or acetonitrile.

In addition, the pharmaceutically acceptable salt may be an alkali metal salt (such as a sodium salt, and the like) or an alkaline earth metal salt (such as a potassium salt, and the like).

The alkali metal salt or alkaline earth metal salt may be obtained by, for example, dissolving the compound of Chemical Formula 1 in an excess of alkali metal hydroxide or alkaline earth metal hydroxide solution, and filtering the undissolved compound salt, followed by evaporating and drying the filtrate.

The pharmaceutically acceptable salt may be appropriately changed into a food-acceptable salt, a cosmetic-acceptable salt, and the like, depending on the use of food, feed, cosmetics, and the like.

In addition, the compounds of the present disclosure may have chiral carbon centers and may therefore exist in the form of R or S isomers, racemic compounds, individual enantiomers or mixtures, individual diastereomers or mixtures, wherein all these stereoisomers and mixtures thereof may be included within the scope of the present disclosure. The stereoisomer may be synthesized in a stereospecific manner using optically pure starting materials and/or reagents with known configurations.

Further, the compound of the present disclosure may include hydrates and solvates of the compound of Chemical Formula 1. The hydrates and solvates may be prepared using known methods, and preferably nontoxic and water-soluble. In particular, preferably, the hydrate and the solvate may be prepared by binding 1 to 5 molecules of water and an alcoholic solvent (particularly, ethanol, or the like), respectively.

The compound of the present disclosure, i.e., the compound represented by Chemical Formula 1, a stereoisomer thereof, or a pharmaceutically acceptable salt thereof, exhibits its high stability and solubility in the body to have excellent bioavailability. The compound represented by Chemical Formula 1, a stereoisomer thereof, or a pharmaceutically acceptable salt thereof may inhibit the activity of NF-κB, which is a major signal transmitter in the inflammatory response, thereby disrupting the initial pathway and process of the biological inflammatory response system to prevent and treat various pathological diseases caused by the inflammatory response.

The benzofuran-based N-acylhydrazone compound represented by [Chemical Formula 1], a stereoisomer thereof, or a pharmaceutically acceptable salt thereof may be usefully employed for the prevention or treatment of an inflammatory disease.

As used herein, the term "inflammatory disease" refers to a condition characterized by one or more signs of pain (pain due to the production of harmful substances and nerve stimulation), fever (fever due to vasodilation), redness (redness due to vasodilation and increased blood flow), swelling (tumor due to excessive inflow or limited outflow of fluid); and loss of function (loss of function, which may be partial or complete, temporary or permanent).

Non-limiting examples of the inflammatory disease in which the compound represented by Chemical Formula 1 according to the present disclosure is capable of being used may include dermatitis, cytokine release syndrome (CRS), cytokine storm, allergy, nasal polyps, rhinitis, chronic sinusitis, nasal congestion, nasal itching, asthma, chronic obstructive pulmonary disease, rheumatoid arthritis, conjunctivitis, keratoconjunctivitis, ophthalmia, dry eye, heart failure, arrhythmia, atherosclerosis, multiple sclerosis, inflammatory bowel disease, inflammatory pain, neurogenic pain, osteoarthritis pain, lupus, sepsis, Crohn's disease, gout, Sjögren's syndrome, Alzheimer's disease, Parkinson's disease, thyroid autoimmune disease, multiple sclerosis, Guillain-Barré syndrome, autism, hemolytic dyslipidemia, thyroiditis, Hashimoto's disease, Graves' disease, ankylosing spondylitis, polymyalgic rheumatoiditis, celiac disease, ulcerative colitis, type 1 diabetes, peripheral neuropathy, diabetic peripheral neuropathy, Wegener's granulomatosis, muscular dystrophy, Fibromyalgia, systemic lupus erythematosus, Behcet's disease, uveitis, glomerulonephritis, Goodpasture syndrome, glandular autoimmune syndrome, Churg-Strauss syndrome, Henoch-Schonlein purpura, Polyarteritis nodosa, Takayasu's arteritis, temporal arteritis, relapsing polychondritis, alopecia areata, narcolepsy, severe acute respiratory syndrome coronavirus 2 infection disease, and the like, but the inflammatory disease is not limited thereto.

In an embodiment of the present disclosure, the benzofuran-based N-acylhydrazone compound represented by [Chemical Formula 1], a stereoisomer thereof or a pharmaceutically acceptable salt thereof may be usefully employed for the treatment of cytokine release syndrome (CRS) and/or cytokine storm.

Cytokine release syndrome (CRS) and/or cytokine storm is a type of systemic inflammatory response syndrome that may be caused by various factors, such as infection or certain drugs.

A symptom of the cytokine release syndrome (CRS) and/or cytokine storm may include elevated levels of inflammatory cytokines. For example, it is characterized by an increase in TNF-alpha, IFN-gamma, IL-1beta, IL-2, IL-6, IL-8, IL-10, IL-13, GM-CSF, IL-5, fractalkine, or a combination thereof or a subcombination thereof.

The cytokine release syndrome (CRS) and/or cytokine storm according to the present disclosure may be more specifically cytokine release syndrome (CRS) and/or cytokine storm caused by a viral infection.

For example, the virus may be any one or more viruses selected from the group consisting of influenza virus, influenza A virus subtype H1N1, avian influenza virus, rhinovirus, adenovirus, coronavirus, MERS Corona Virus, severe acute respiratory syndrome coronavirus 2, parainfluenza virus, respiratory syncytial virus, herpesvirus (HSV), human immunodeficiency virus (HIV), and hepatitis virus.

The compound represented by Chemical Formula 1, a stereoisomer thereof or a pharmaceutically acceptable salt thereof according to the present disclosure may inhibit a cytokine storm that rapidly progresses through the action of dual inhibition that regulates both canonical and non-canonical pathways in the regulation of NF-κB to thereby exhibit excellent effects in the treatment of diseases. In particular, it is possible to exhibit excellent treatment and improvement effects on viral infections in which acute inflammatory responses, particularly cytokine storms, are problematic, such as infection caused by severe acute respiratory syndrome coronavirus 2.

According to the present disclosure, the inflammatory disease may be dermatitis. The dermatitis may be, for example, any one or more selected from the group consisting of atopic dermatitis, contact dermatitis, allergic dermatitis, acne, eczema, rosacea, oily skin, psoriasis, eczema, prurtis, skin itching, urticaria, chronic idiopathic urticaria, systemic sclerosis, leukoplakia, scleroderma, Behcet's disease, and contact transmission impetigo, but is not limited thereto.

According to the present disclosure, the dermatitis may be atopic dermatitis. In the present disclosure, the term "atopic dermatitis" refers to a chronic skin disorder that is inflammatory, recurrent, non-infectious, and pruritic.

Specific forms of atopic dermatitis, named from the place where the dermatitis occurs or an appearance thereof or a stress factor causing the dermatitis, are also included in the term atopic dermatitis of the present disclosure. Atopic dermatitis shows symptoms such as dry eczematous skin, papules, and severe itching, wherein epidermal hyperplasia, epidermal proliferation, and accumulation of lymphocytes and mast cells are found in lesion samples of atopic patients. Patients with atopic dermatitis generally suffer from severe itching, thereby causing inflammation of skin lesions, further aggravating itching, and further exacerbating clinical symptoms.

According to the present disclosure, the inflammatory disease may be sepsis.

The benzofuran-based N-acylhydrazone compound represented by [Chemical Formula 1], a stereoisomer thereof or a pharmaceutically acceptable salt thereof according to the present disclosure inhibits the expression of inflammatory cytokines or chemokines and exhibits anti-inflammatory action with respect to sepsis presenting symptoms of a cytokine storm and/or severe cytokine syndrome due to a rapid inflammatory response, thereby suppressing death or disease progress caused by sepsis.

According to the present disclosure, the inflammatory disease may be severe acute respiratory syndrome coronavirus 2 infection disease. A disease caused by severe acute respiratory syndrome coronavirus 2 infection may be an inflammatory disease in the respiratory tract. Symptoms of the severe acute respiratory syndrome coronavirus 2 infection disease may appear after, for example, an incubation period of 2 to 14 days after infection with the virus. These symptoms include, for example, any symptoms caused by the virus infection, including high fever, cough, shortness of breath, pneumonia, gastrointestinal symptoms such as diarrhea, organ dysfunction (kidney failure, kidney dysfunction, and the like), septic shock, and death in severe cases. In particular, in the severe acute respiratory syndrome coronavirus 2 infection disease, the majority of symptoms leading to death are highly related to cytokine storm and/or severe cytokine syndrome symptoms. The benzofuran-based N-acylhydrazone compound represented by [Chemical Formula 1], a stereoisomer thereof or a pharmaceutically acceptable salt thereof according to the present disclosure may selectively bind to IKKa, an important factor in the NF-κB inflammatory signaling pathway, thereby inhibiting the formation of active structures to inhibit and treat the cytokine storm and/or severe cytokine syndrome symptoms through the action of dual inhibition that regulates both the canonical and non-canonical pathways.

The benzofuran-based N-acylhydrazone compound represented by [Chemical Formula 1], a stereoisomer thereof or a pharmaceutically acceptable salt thereof according to the present disclosure may inhibit the activity of NF-κB, thereby inhibiting the symptoms of the cytokine storm and/or cytokine release syndrome and exhibiting anti-inflammatory activity, but the present disclosure is not limited thereto.

It was confirmed that the benzofuran-based N-acylhydrazone compound according to the present disclosure had an inhibitory effect on the NF-κB inflammatory response pathway, which is the main signaling system of inflammatory response control, through a cell-based reporter assay, and exhibited the anti-inflammatory activity by disrupting the phosphorylation of p65, an important factor in the NF-κB signaling pathway.

The benzofuran-based N-acylhydrazone compound according to the present disclosure selectively binds to IKKa, an important factor in the NF-κB inflammatory signaling pathway, and inhibits the formation of an active structure.

The benzofuran-based N-acylhydrazone compound according to the present disclosure may inhibit and treat the cytokine storm and/or severe cytokine syndrome symptoms through the action of dual inhibition that regulates both the canonical and non-canonical pathways of NF-κB.

In particular, in the case of a rapid increase in inflammatory cytokines that may occur in the lungs or an increase in inflammatory response levels due to sepsis, the action of the dual inhibition may have a significantly excellent effect in the treatment of related diseases.

The benzofuran-based N-acylhydrazone compound represented by [Chemical Formula 1], a stereoisomer thereof, or a pharmaceutically acceptable salt thereof according to the present disclosure may exhibit anti-inflammatory activity by reducing the number of inflammatory immune cells, and may also exhibit anti-inflammatory activity by inhibiting the expression of inflammatory cytokines.

In particular, it is possible to exhibit excellent therapeutic efficacy by suppressing epithelial hyperplasia, and the like, caused by inflammation in the skin or the like.

The pharmaceutical composition of the present disclosure may further comprise at least one active ingredient exhibiting anti-inflammatory or anti-viral activity.

The composition of the present disclosure may further comprise a pharmaceutically acceptable additive, wherein the pharmaceutically acceptable additive may include starch, gelatinized starch, microcrystalline cellulose, milk sugar, povidone, colloidal silicon dioxide, calcium hydrogen phosphate, lactose, mannitol, taffy, gum arabic, pregelatinized starch, corn starch, powdered cellulose, hydroxypropyl cellulose, opadry, sodium starch glycolate, carnauba wax, synthetic aluminum silicate, stearic acid, magnesium stearate, aluminum stearate, calcium stearate, white sugar, dextrose, sorbitol, talc, and the like. The pharmaceutically acceptable additive according to the present disclosure is preferably contained in an amount of 0.1 to 90 parts by weight based on the composition, but is not limited thereto.

In other words, the composition of the present disclosure may be administered in various oral and parenteral formulations during actual clinical administration. When formulated, the composition of the present disclosure may be prepared using diluents or excipients such as fillers, extenders, binders, wetting agents, disintegrants, surfactants, and the like, that are commonly used in the art. Solid preparations for oral administration may include tablets, pills, powders, granules, capsules, and the like, and these solid preparations may be prepared by mixing tobacco weed extract with at least one or more excipients such as starch, calcium carbonate, sucrose, lactose, gelatin, and the like. Further, in addition to simple excipients, lubricants such as magnesium stearate and talc may also be used. Liquid preparations for oral use may be suspensions, internal solutions, emulsions, syrups, and the like, and may include various excipients such as wetting agents, sweeteners, aromatic agents, preservatives, and the like, in addition to water and liquid paraffin, which are commonly used simple diluents. Preparations for parenteral administration may include sterilized aqueous solutions, non-aqueous solvents, suspensions, emulsions, freeze-dried preparations, and suppositories. Propylene glycol, polyethylene glycol, vegetable oils such as olive oil, and injectable esters such as ethyl oleate, and the like, may be used as the non-aqueous solvents and suspensions. As a base for the suppository, witepsol, macrogol, tween 61, cacao butter, laurin oil, glycerogelatin, and the like, may be used.

The composition of the present disclosure may be administered orally or parenterally depending on the desired method. For parenteral administration, transdermal administration, skin external use, intraperitoneal injection, intrarectal injection, subcutaneous injection, intravenous injection, intramuscular injection, or intrathoracic injection may be selected as an injection method. For example, the composition of the present disclosure may be administered transdermally. The dosage varies depending on the patient's weight, age, sex, health condition, diet, administration time, administration method, excretion rate, and severity of the disease, and the like.

The composition according to the present disclosure is administered in a pharmaceutically effective amount. In the present disclosure, the "pharmaceutically effective amount" means an amount sufficient to treat a disease at a reasonable benefit/risk ratio applicable to medical treatment, and the effective dose level may be determined depending on factors including the type and severity of the patient's disease, the activity of the drug, the sensitivity to the drug, the time of administration, the route of administration, the rate of excretion, the duration of treatment, drugs used concurrently, and other factors well known in the medical field. The composition of the present disclosure may be administered as an individual therapeutic agent or in combination with other therapeutic agents, and may be administered sequentially or simultaneously with conventional therapeutic agents, and may be administered singly or multiple times. In consideration of all of the above factors, it is important to administer the composition in an amount capable of obtaining the maximum effect with the minimum amount without side effects, which may be easily determined by a person skilled in the art.

Specifically, the effective amount of the compound according to the present disclosure may vary depending on the patient's age, sex, and weight. In general, 0.1 mg to 100 mg, preferably 0.5 mg to 10 mg per 1 kg of body weight may be administered daily, every other day or 1 to 5 times a week, or may be administered in an amount divided into 1 to 5 times a day. However, the dosage may increase or decrease depending on the route of administration, severity, sex, weight, age, and the like, and thus the dosage is not intended to limit the scope of the present disclosure in any way.

The compound of the present disclosure or the pharmaceutical composition comprising the same may be used as an anti-inflammatory agent.

Accordingly, the present disclosure provides use of the compound represented by Chemical Formula 1, a stereoisomer thereof, or a pharmaceutically acceptable salt thereof for the prevention or treatment of an inflammatory disease.

Further, the present disclosure provides use of the compound represented by Chemical Formula 1, a stereoisomer thereof or a pharmaceutically acceptable salt thereof for the manufacture of a medicament for the prevention or treatment of an inflammatory disease.

In addition, the present disclosure provides a method for preventing or treating an inflammatory disease, comprising administering the compound represented by Chemical Formula 1, a stereoisomer thereof, or a pharmaceutically acceptable salt thereof to a subject in need thereof.

Herein, "prevention" means any action that inhibits or delays the occurrence, spread, and recurrence of the disease by administration of the compound, and "treatment" refers to any action in which the symptoms of the disease are ameliorated or beneficially changed by administration of the compound.

Herein, the term "subject in need" refers to all animals such as monkeys, cows, horses, sheep, pigs, chickens, turkeys, quails, cats, dogs, mice, rats, rabbits, guinea pigs, and the like, including humans (patients) who have or are likely to develop the disease, and may specifically refer to mammals. In addition, the subject in need may refer to a biological sample.

In addition, "administration" means providing a predetermined substance to a subject in need thereof by any suitable method, and the administration route of the compound of the present disclosure may be achieved through any general route as long as it is able to reach the target tissue.

The benzofuran-based N-acylhydrazone compound represented by [Chemical Formula 1] of the present disclosure inhibits the NF-κB inflammatory response pathway and disrupts the phosphorylation of p65 (RelA), which is an important factor in the NF-κB signaling pathway, thereby exhibiting excellent anti-inflammatory efficacy. Further, anti-inflammatory activity is exhibited by reducing the number of inflammatory immune cells and inhibiting the expression of inflammatory cytokines.

The present disclosure also provides the compound represented by Chemical Formula 1, a stereoisomer thereof, or a pharmaceutically acceptable salt thereof for use in the prevention or treatment of an inflammatory disease.

The present disclosure also provides use of the compound represented by Chemical Formula 1, a stereoisomer thereof, or a pharmaceutically acceptable salt thereof in the manufacture of a medicament for the treatment of an inflammatory disease.

Thus, the composition comprising the compound represented by Chemical Formula 1, a stereoisomer thereof, or a pharmaceutically acceptable salt thereof may be usefully employed as a food composition for preventing or improving an inflammatory disease.

According to the present disclosure, the food composition comprises a health functional food.

In general, the food composition according to the present disclosure may further comprise an additive, or the like, in other food compositions, health functional foods or beverages.

For example, the food composition of the present disclosure may contain sweeteners such as sucrose, fructose, glucose, D-sorbitol, mannitol, isomaltooligosaccharide, stevioside, aspartame, acesulfame potassium, and sucralose, acidulants such as anhydrous citric acid, DL-malic acid, succinic acid and salts thereof, preservatives such as benzoic acid and derivatives thereof, various nutrients, vitamins, minerals (electrolytes), flavors such as synthetic flavors and natural flavors, colorants and enhancers (cheese, chocolate, and the like), pectic acid and salts thereof, alginic acid and salts thereof, organic acids, protective colloidal thickeners, pH adjusters, stabilizers, preservatives, glycerin, alcohol, carbonation agents used in carbonated beverages, and the like. In addition, the food compositions of the present disclosure may contain fruit flesh for preparing natural fruit juice and vegetable beverages. The ratio of these additives may range from about 20 parts by weight or less per 100 parts by weight of the food composition of the present disclosure.

When the food composition of the present disclosure is a beverage, the food composition may further comprise a flavoring agent or natural carbohydrate commonly contained in beverages. The natural carbohydrate may be a monosaccharide such as glucose or fructose, a disaccharide such as maltose or sucrose, a polysaccharide such as dextrin or cyclodextrin, or a sugar alcohol such as xylitol, sorbitol or erythritol. In addition, the flavoring agent may be a natural flavoring agent such as thaumatin or *stevia* extract (rebaudioside A, glycyrrhizin, or the like) or a synthetic flavoring agent such as saccharin, aspartame, or the like. When the food composition is a beverage, the natural carbohydrate may be generally contained in an amount of about 1 to 20 g, preferably about 5 to 12 g, per 100 mL of the composition.

The food composition of the present disclosure may be prepared in the form of powder, granule, tablet, capsule or beverage to be used as foods, beverages, gum, tea, vitamin complexes, and health food supplements.

The benzofuran-based N-acylhydrazone compound represented by [Chemical Formula 1] of the present disclosure inhibits the NF-κB inflammatory response pathway and disrupts the phosphorylation of p65 (ReIA), which is an important factor in the NF-κB signaling pathway, thereby exhibiting excellent anti-inflammatory efficacy. In addition, the development of diseases such as cytokine release syndrome (CRS) and cytokine storm is ameliorated or prevented by reducing high expression of inflammatory cytokines.

Thus, the composition comprising the compound represented by Chemical Formula 1, a stereoisomer thereof, or a pharmaceutically acceptable salt thereof may be usefully employed as a feed composition for preventing or improving an inflammatory disease.

In the present disclosure, the feed may be a feed for reptiles, fish, birds or mammals, and preferably, may be a feed for livestock or aquatic organisms, which are suitable for breeding by acclimation of wild habits and are able to contribute to the farm household income increase, under the provisions of Article 2(1) of the Livestock Act and any of the subparagraphs of Article (2) of Enforcement Rule of the same Act. The livestock may include cattle, horses, mules, donkeys, goats, mountain goats, sheep, deer, pigs, rabbits, poultry, and the like, and the poultry may include chickens, turkeys, ducks, ostriches, geese, quails, and the like, preferably chickens, but is not limited thereto as long as it is suitable for obtaining livestock products by breeding. The "livestock product" refers to meat, milk, eggs, and honey produced from livestock and processed products thereof, raw hides (including raw fur), raw wool, and other livestock products, under the provisions of Article 2(3) of the Livestock Act, as prescribed by the Ordinance of the Ministry of Agriculture and Forestry. In addition, the livestock may be a dog, cat, and the like, including companion animals, but is not limited thereto.

The term "feed" in the present disclosure means any natural or artificial diet, one-meal, or the like, or components of the one-meal, intended to be eaten, ingested, digested by an animal or suitable for this practice. As an embodiment, a feed composition containing an american king mealworm larva extract of the present disclosure may comprise concentrated feed, coarse feed and/or special feed.

The concentrated feed includes seed fruits including cereals such as wheat, oats, and corn; bran including rice bran, wheat bran, barley bran, and the like, as by-products obtained by refining grain; oil cakes, as by-products obtained from oil extraction of soybeans, fluids, sesame seeds, linseed, and coco palms; residues such as residual starches, the main component of starch residues, which are the remainder after removing starch from sweet potatoes and potatoes; fish meal; fish offal; fish soluble, which is a concentrate of fresh liquid obtained from fish; animal feeds, such as meat meal, blood meal, feather meal, skim milk powder, and dried whey obtained by drying whey which is the remainder when cheese is produced from milk and casein is produced from skim milk; yeast, chlorella, seaweed, and the like.

The coarse feed includes raw grass feed such as wild grass, forage, and fodder; root vegetables such as turnip for feed, beet for feed, Lutherbearer which is a type of turnip; silage which is a storage feed obtained by filling a silo with raw grass, forage crops, and grains, followed by lactic acid fermentation; hay obtained by cutting and drying wild grass and forage; straw of breeding crops; leaves of leguminous plants, and the like. Special feed includes mineral feed such as oyster shells and rock salt; urea feed such as urea or derivatives thereof such as diureido isobutane, and the like; and feed additives which are substances added in small amounts to formulated feeds in order to supplement ingredients that are likely to be lacking when only natural feed ingredients are blended, or to improve the storability of feeds.

The benzofuran-based N-acylhydrazone compound represented by [Chemical Formula 1] of the present disclosure inhibits the NF-κB inflammatory response pathway and disrupts the phosphorylation of p65 (ReIA), which is an important factor in the NF-κB signaling pathway, thereby exhibiting excellent anti-inflammatory efficacy. In addition, the development of diseases such as cytokine release syndrome (CRS) and cytokine storm is ameliorated or prevented by reducing high expression of inflammatory cytokines.

Therefore, the present disclosure may provide a cosmetic composition for preventing or improving dermatitis, comprising the benzofuran-based N-acylhydrazone compound represented by Chemical Formula 1, a stereoisomer thereof or a pharmaceutically acceptable salt thereof. Further, the present disclosure provides a cosmetic composition for relieving skin irritation and/or skin inflammation, comprising the benzofuran-based N-acylhydrazone compound represented by Chemical Formula 1, a stereoisomer thereof or a pharmaceutically acceptable salt thereof.

As used herein, "skin damage" refers to any skin damage capable of being ameliorated, prevented or rapidly recovered by suppression, reduction, or decrease of increased cytokine expression levels. As used herein, "skin irritation" means irritations that may occur in any skin such as itching, stinging, erythema, and skin swelling due to any stimulation.

The cosmetic composition of the present disclosure may be prepared in any formulation conventionally prepared in the art, and for example, may be formulated into a solution, suspension, emulsion, paste, gel, cream, lotion, powder, soap, surfactant-containing cleanser, oil, powder foundation, emulsion foundation, wax foundation, spray, and the like, but is not limited thereto. More specifically, the cosmetic composition may be prepared in the formulation of softening lotion, nourishing lotion, nourishing cream, massage cream, essence, eye cream, cleansing cream, cleansing foam, cleansing water, pack, spray or powder.

When the formulation of the present disclosure is a paste, cream or gel, animal oil, vegetable oil, wax, paraffin, starch, tracanth, cellulose derivative, polyethylene glycol, silicone, bentonite, silica, talc, zinc oxide, or the like, may be used as a carrier component.

When the formulation of the present disclosure is a powder or spray, lactose, talc, silica, aluminum hydroxide, calcium silicate or polyamide powder may be used as the carrier component, and in particular, when the formulation of the present disclosure is a spray, a propellant such as chlorofluorohydrocarbon, propane/butane or dimethyl ether may be additionally included.

When the formulation of the present disclosure is a solution or emulsion, a solvent, a solubilizing agent or an emulsifying agent is used as the carrier component, such as water, ethanol, isopropanol, ethyl carbonate, ethyl acetate, benzyl alcohol, benzyl benzoate, propylene glycol, 1,3-butyl glycol oil, glycerol fatty ester, polyethylene glycol or sorbitan fatty acid ester.

When the formulation of the present disclosure is a suspension agent, the carrier component may be a liquid diluent such as water, ethanol or propylene glycol, a suspension such as ethoxylated isostearyl alcohol, polyoxyethylene sorbitol ester or polyoxyethylene sorbitan ester, microcrystalline cellulose, aluminum metahydroxide, bentonite, agar, tracanth, or the like.

When the formulation of the present disclosure is a surfactant-containing cleanser, the carrier component may be aliphatic alcohol sulfate, aliphatic alcohol ether sulfate, sulfosuccinic acid monoester, isethionate, imidazolinium derivative, methyl taurate, sarcosinate, fatty acid amide ether sulfate, alkylamidobetaine, aliphatic alcohol, fatty acid glyceride, fatty acid diethanolamide, vegetable oil, lanolin derivative, or ethoxylated glycerol fatty acid ester, or the like.

Hereinafter, preferred embodiments are presented to assist understanding of the present disclosure. However, the following Examples are merely illustrative of the present disclosure, and it is obvious to those skilled in the art that various changes and modifications can be made within the scope and spirit of the present disclosure, and these variations and modifications fall within the scope of the appended claims.

Abbreviations used in the Examples below are defined as follow:

EA: ethyl acetate, EtOH: ethanol,
DMF: dimethylformamide, n-Hex: n-hexane,
PrOH: propanol, DMSO: dimethyl sulfoxide,
Et: ethyl.

<Preparation of Aromatic Substituted Benzofuran-2-Carbohydrazide Derivative>

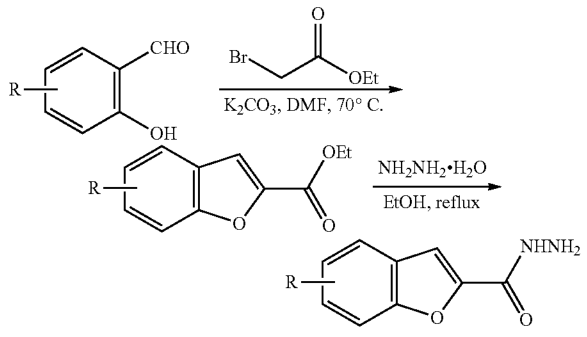

R: 5-$CH_3$, 5-$OCH_3$, 4,7-dimethyl, 4,6-dimethoxy

-continued

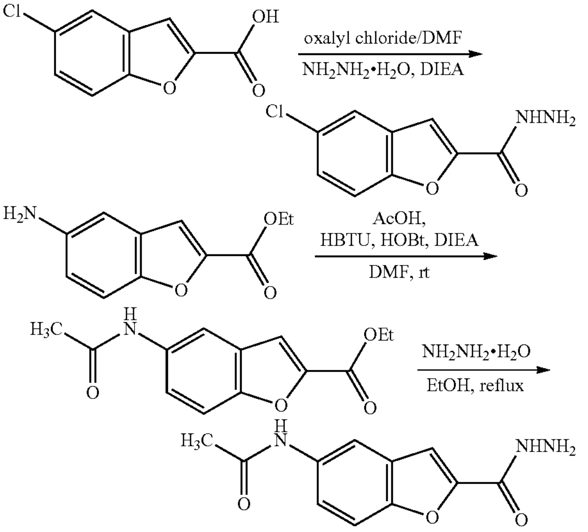

Preparation Example 1: Ethyl 5-Methylbenzofuran-2-Carboxylate

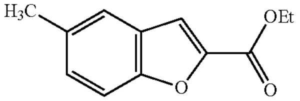

5-Methylsalicylaldehyde (1.40 g, 10.3 mmol) was dissolved in DMF (30 mL), then $Ce_2SO_4$(10.07 g, 30.9 mmol) and ethyl bromoacetate (1.38 mL, 12.4 mmol) were added thereto, and reacted at 70° C. for 15 hours. The reaction solution was diluted with water and extracted with EA. The organic layer was dried over $MgSO_4$, filtered, and distilled under reduced pressure. The residue was separated by column chromatography (n-Hex:EA=10:1) to obtain 1.28 g of the title compound (yield 61%, colorless liquid).

$^1$H NMR (400 MHz, $CDCl_3$): δ 7.49-7.46 (m, 3H), 7.26 (m, 1H), 4.45 (q, J=7.2 Hz, 2H), 2.46 (s, 3H), 1.44 (t, J=7.2 Hz, 3H); $^{13}$C NMR (100 MHz, $CDCl_3$): δ 159.85, 154.37, 145.92, 133.51, 129.27, 127.22, 122.45, 113.74, 112.02, 61.61, 21.45, 14.51; mp 38-39° C.

Preparation Example 2: 5-Methylbenzofuran-2-carbohydrazide

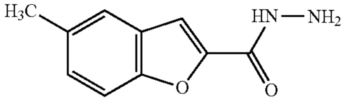

Ethyl 5-methylbenzofuran-2-carboxylate (2.04 g, 10.0 mmol) obtained in Preparation Example 1 was dissolved in EtOH (30 mL), then hydrazine monohydrate (1.50 g, 30.0 mmol) was added thereto, and refluxed for 24 hours. The reaction solution was distilled under reduced pressure to obtain a solid, and the obtained solid was washed with water and dried to obtain 1.72 g of the title compound (yield 90%, white solid).

$^1$H NMR (400 MHz, DMSO-$d_6$): δ 9.97 (s, 1H), 7.52-7.49 (m, 2H), 7.43 (s, 1H), 7.25 (dd, J=8.4, 1.6 Hz, 1H), 4.55 (br s, 2H), 2.40 (s, 3H); $^{13}$C NMR (100 MHz, DMSO-$d_6$): δ 157.92, 152.64, 148.48, 132.68, 127.84, 127.11, 122.04, 111.27, 108.47, 20.81; MS (MALDI-TOF): m/z 213 $[M+Na]^+$; mp 159° C.

Preparation Example 3: Ethyl 5-methoxybenzofuran-2-carboxylate

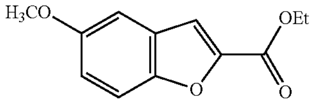 [SMILES: CCOC(=O)c1cc2cc(OC)ccc2o1]

2-Hydroxy-5-methoxybenzaldehyde (1.25 mL, 10.0 mmol) was dissolved in DMF (30 mL), then $K_2CO_3$ (6.91 g, 50.0 mmol) and ethyl bromoacetate (1.33 mL, 12.0 mmol) were added thereto, and reacted at 70° C. for 15 hours. The reaction solution was diluted with water and extracted with EA. The organic layer was dried over $MgSO_4$, filtered, and distilled under reduced pressure. The residue was separated by column chromatography (n-Hex:EA=3:1) to obtain 1.1 g of the title compound (yield 50%, white solid).

$^1$H NMR (400 MHz, $CDCl_3$): δ 7.50-7.47 (m, 2H), 7.08-7.05 (m, 2H), 4.45 (q, 2H, J=7.2 Hz), 3.86 (s, 3H), 1.44 (t, 3H, J=7.2 Hz); mp 53° C.

Preparation Example 4: 5-Methoxybenzofuran-2-carbohydrazide

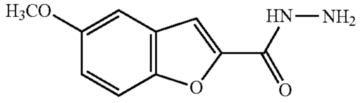 [SMILES: COc1ccc2oc(C(=O)NN)cc2c1]

Ethyl 5-methoxybenzofuran-2-carboxylate (1.03 g, 4.68 mmol) obtained in Preparation Example 3 was dissolved in EtOH (30 mL), then hydrazine monohydrate (702.8 mg, 14.04 mmol) was added thereto, and refluxed for 24 hours. The reaction solution was distilled under reduced pressure to obtain a solid, and the obtained solid was washed with $CH_2Cl_2$ and dried to obtain 918 mg of the title compound (yield 95%, white solid).

$^1$H NMR (400 MHz, DMSO-$d_6$): δ 9.98 (s, 1H), 7.53 (d, 1H, J=9.0 Hz), 7.44 (s, 1H), 7.25 (d, 1H, J=2.7 Hz), 7.02 (dd, 1H, J=9.0, 2.7 Hz), 4.55 (br s, 2H), 3.79 (s, 3H); $^{13}$C NMR (100 MHz, DMSO-$d_6$): δ 157.85, 155.97, 149.10, 149.03, 127.65, 115.80, 112.34, 108.34, 104.09, 55.58; MS (MALDI-TOF): m/z 229.0 [M+Na]+, 245 $[M+K]^+$; mp 163-164° C.

Preparation Example 5: 5-Chlorobenzofuran-2-carbohydrazide

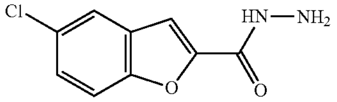 [SMILES: NNC(=O)c1cc2cc(Cl)ccc2o1]

Oxalic chlonde (272.2 μL, 3.0 mmol) and DMF (50 μL) were added to CH2Cl2 (5 mL) at 0° C., stirred for 5 minutes, and a mixed solution of 5-chlorobenzofuran-2-carboxylic acid (393.2 mg, 2.0 mmol) in $CH_2Cl_2$/DMF (5 mL, 4:1) was then added thereto, and stirred at room temperature for 2 hours. The reaction solution was distilled under reduced pressure, $CH_2Cl_2$ (5 mL) was added again, and a solution of hydrazine monohydrate (120.1 mg, 2.4 mmol) in $CH_2Cl_2$ (5 mL) and N,N-diisopropylethylamine (DIEA, 1.74 mL, 10 mmol) were added at 0° C. and stirred at room temperature for 15 hours. The reaction solution was diluted with water and extracted with EA. The organic layer was dried over $Na_2SO_4$, filtered, and distilled under reduced pressure. The residue was washed with $CH_2Cl_2$ and dried to obtain 295 mg of the title compound (yield 70%, pale yellow solid).

$^1$H NMR (400 MHz, DMSO-$d_6$): δ 10.10 (s, 1H), 7.86 (d, J=2.4 Hz, 1H), 7.68 (d, J=9.2 Hz, 1H), 7.48 (s, 1H), 7.46 (dd, J=9.2, 2.4 Hz, 1H), 4.59 (br s, 2H); $^{13}$C NMR (100 MHz, DMSO-$d_6$): δ 157.41, 152.66, 149.79, 128.65, 127.99, 126.56, 122.02, 113.44, 108.25; MS (MALDI-TOF): m/z 233 $[M+Na]^+$; mp 174-175° C.

Preparation Example 6: Ethyl 4,7-dimethylbenzofuran-2-carboxylate

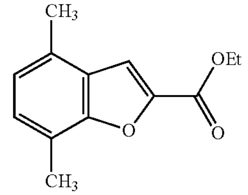 [SMILES: CCOC(=O)c1cc2c(C)ccc(C)c2o1]

3,6-dimethylsalicylaldehyde (450.5 mg, 3.0 mmol) was dissolved in DMF (30 mL), then $Ce_2SO_4$(2.93 g, 9.0 mmol) and ethyl bromoacetate (399.2 μL, 3.60 mmol) were added thereto, and reacted at 70° C. for 15 hours. The reaction solution was diluted with water and extracted with EA. The organic layer was dried over $MgSO_4$, filtered, and distilled under reduced pressure. The residue was separated by column chromatography (n-Hex:EA=20:1) to obtain 360 mg of the title compound (yield 55%, colorless liquid).

$^1$H NMR (400 MHz, $CDCl_3$): δ 7.56 (s, 1H), 7.14 (d, J=7.2 Hz, 1H), 6.99 (d, J=7.2 Hz, 1H), 4.45 (q, J=7.2 Hz, 2H), 2.55 (s, 3H), 2.52 (s, 3H), 1.44 (t, J=7.2 Hz, 3H); $^{13}$C NMR (100 MHz, $CDCl_3$): δ 159.91, 154.90, 145.08, 130.19, 128.30, 126.63, 123.90, 119.85, 113.01, 61.43, 18.29, 15.00, 14.46

Preparation Example 7: 4,7-Dimethylbenzofuran-2-carbohydrazide

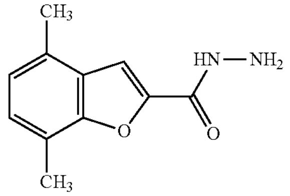

Ethyl 4,7-dimethylbenzofuran-2-carboxylate (290.3 mg, 1.33 mmol) obtained in Preparation Example 6 was dissolved in EtOH (30 mL), then hydrazine monohydrate (199.7 mg, 3.99 mmol) was added thereto, and refluxed for 24 hours. The reaction solution was distilled under reduced pressure to obtain a solid, and the obtained solid was washed with water and dried to obtain 236 mg of the title compound (yield 87%, white solid).

$^{1}H$ NMR (400 MHz, DMSO-$d_6$): δ 9.97 (s, 1H), 7.55 (s, 1H), 7.13 (d, J=7.4 Hz, 1H), 7.00 (d, J=7.4 Hz, 1H), 4.59 (br s, 2H), 2.46 (s, 6H, $CH_3$x2); $^{13}C$ NMR (100 MHz, DMSO-$d_6$): δ 158.05, 153.07, 147.65, 129.34, 127.07, 126.47, 123.64, 118.65, 107.94, 17.86, 14.38; MS (MALDI-TOF): m/z 227 $[M+Na]^+$; mp 187° C.

Preparation Example 8: Ethyl 4,6-dimethoxybenzofuran-2-carboxylate

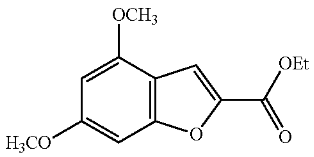 [SMILES: CCOC(=O)c1cc2c(OC)cc(OC)cc2o1]

4,6-Dimethoxysalicylaldehyde (499.2 mg, 2.74 mmol) was dissolved in DMF (10 mL), and $K_2CO_3$ (1.89 g, 13.7 mmol) and ethyl bromoacetate (364.8 μL, 3.29 mmol) were then added thereto, and reacted at 70° C. for 15 hours. The reaction solution was diluted with water and extracted with EA. The organic layer was dried over $MgSO_4$, filtered, and distilled under reduced pressure. The residue was separated by column chromatography (n-Hex:EA=20:1) to obtain 460 mg of the title compound (yield 67%, white solid). [232]$^{1}H$ NMR (400 MHz, $CDCl_3$): δ 7.54 (m, 1H), 6.67 (m, 1H), 6.35 (d, J=1.9 Hz, 1H), 4.41 (q, J=7.2 Hz, 2H), 3.90 (s, 3H), 3.857 (s, 3H), 1.40 (t, J=7.2 Hz, 3H); (MALDI-TOF): m/z 251 $[M+H]^+$; mp 98° C.

Preparation Example 9: 4,6-Dimethoxybenzofuran-2-carbohydrazide

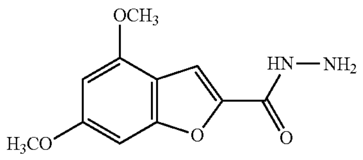 [SMILES: COc1cc(OC)c2cc(C(=O)NN)oc2c1]

Ethyl 4,6-dimethoxybenzofuran-2-carboxylate (450.5 mg, 1.80 mmol) obtained in Preparation Example 8 was dissolved in EtOH (20 mL), and hydrazine monohydrate (450.5 mg, 9.0 mmol) was then added thereto, and refluxed for 6 hours. The reaction solution was poured into cold water to obtain a solid, and the resulting solid was filtered, washed with ethyl ether, and dried to obtain 360 mg of the title compound (yield 85%, white solid).

$^{1}H$ NMR (400 MHz, DMSO-$d_6$): δ 9.78 (s, 1H), 7.40 (d, J=0.8 Hz, 1H), 6.79 (m, 1H), 6.45 (d, J=2.0 Hz, 1H), 4.49 (br s, 2H), 3.88 (s, 3H), 3.82 (s, 3H); $^{13}C$ NMR (100 MHz, DMSO-$d_6$): δ 160.64, 158.10, 156.16, 153.94, 146.15, 110.83, 105.97, 94.98, 88.36, 55.79, 55.71; MS (MALDI-TOF): m/z 259 $[M+Na]^+$; mp 194° C.

Preparation Example 10: Ethyl 5-acetamidobenzofuran-2-carboxylate

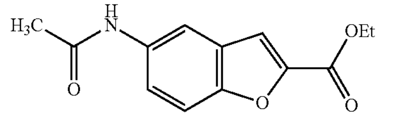 [SMILES: CCOC(=O)c1cc2cc(NC(C)=O)ccc2o1]

Ethyl 5-aminobenzofuran-2-carboxylate (205.2 mg, 1.0 mmol) was dissolved in DMF (3 mL), and (2-(1H-benzotriazol-1-yl)-1,1,3,3-tetramethyluronium hexafluorophosphate (HBTU, 417.2 mg, 1.1 mmol), hydroxybenzotriazole (HOBt, 148.6 mg, 1.1 mmol), N,N-diisopropylethylamine (DIEA, 209.0 μL, 1.2 mmol), and acetic acid (63.0 μL, 1.1 mmol) were then added thereto, and reacted at room temperature for 15 hours. The reaction solution was diluted with water and extracted with EA. The organic layer was dried over $MgSO_4$, filtered, and distilled under reduced pressure. The residue was separated by column chromatography ($CH_2Cl_2$:EA=3:1) to obtain 162 mg of the title compound (yield 66%, white solid).

$^{1}H$ NMR (400 MHz, DMSO-$d_6$): δ 10.06 (s, 1H), 8.19 (d, J=2.0 Hz, 1H), 7.75 (d, J=0.8 Hz, 1H), 7.65 (d, J=8.8 Hz, 1H), 7.53 (dd, J=8.8, 2.0 Hz, 1H), 4.35 (q, J=7.2 Hz, 2H), 2.07 (s, 3H), 1.33 (t, J=7.2 Hz, 3H); $^{13}C$ NMR (100 MHz, DMSO-$d_6$): δ 168.76, 159.66, 152.77, 146.68, 134.10, 127.54, 121.15, 114.18, 114.07, 112.66, 61.79, 24.64, 14.49; mp 181-182° C.

Preparation Example 11: N-(2-(hydrazinecarbonyl)benzofuran-5-yl)acetamide

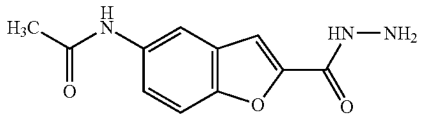 [SMILES: CC(=O)Nc1ccc2oc(C(=O)NN)cc2c1]

Ethyl 5-acetamidobenzofuran-2-carboxylate (514.3 mg, 2.08 mmol) obtained in Preparation Example 10 was dissolved in 1-PrOH (20 mL), then hydrazine monohydrate (312.4 mg, 6.24 mmol) was added thereto, and refluxed for 24 hours. The reaction solution was distilled under reduced pressure to obtain a solid, and the obtained solid was washed with a mixed solvent of n-Hex and $CH_2Cl_2$(1:1) and dried to obtain 392 mg of the title compound (yield 81%, white solid).

$^{1}H$ NMR (400 MHz, DMSO-$d_6$): δ 10.02 (s, 1H), 9.97 (s, 1H), 8.10 (d, J=1.6 Hz, 1H), 7.55 (d, J=9.2 Hz, 1H), 7.48-7.45 (m, 2H), 4.55 (br s, 2H), 2.06 (s, 3H); $^{13}C$ NMR (100 MHz, DMSO-$d_6$): δ 168.23, 157.84, 150.42, 148.93, 135.37, 127.10, 119.12, 111.98, 111.72, 109.06, 23.96; MS (MALDI-TOF) m/z 256 [M+Na]+, 272 [M+K]+; mp 219-220° C.

Preparation of Aromatic/N-Substituted indol-3-carboxaldehyde Derivative

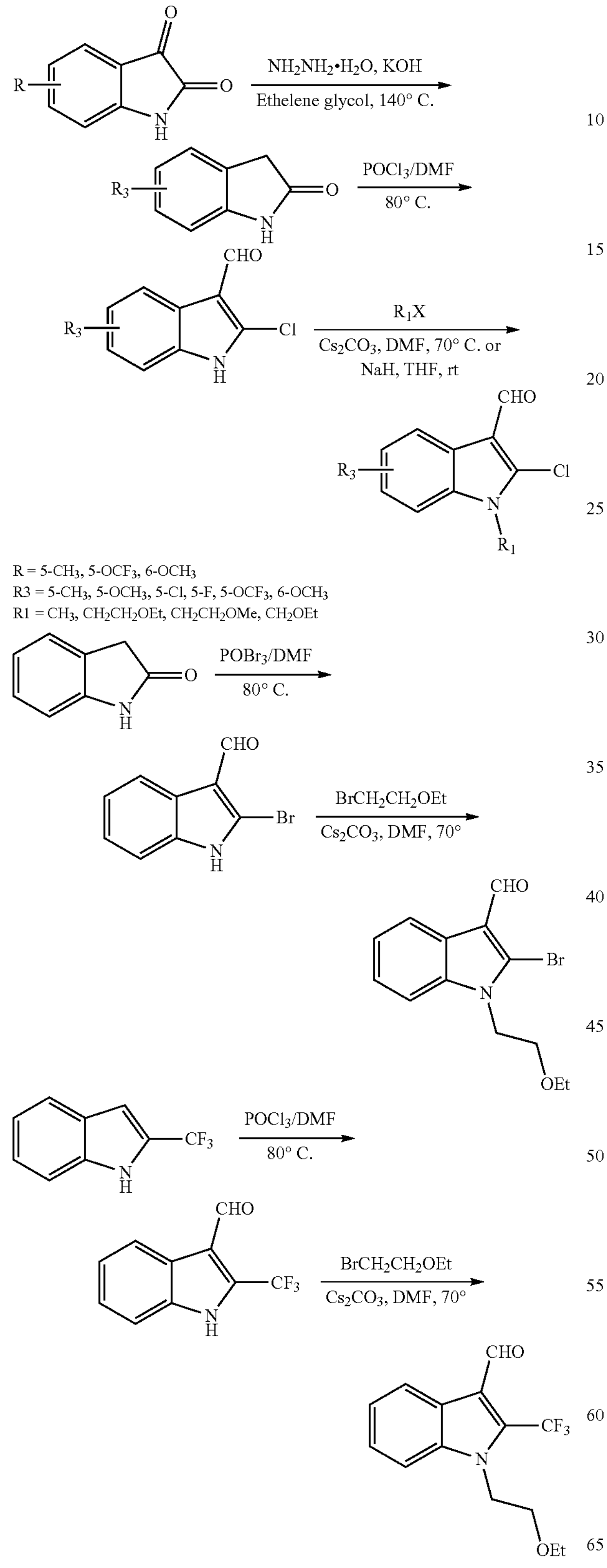

Preparation Example 12: 2-Chloro-1-methyl-1H-indol-3-carboxaldehyde

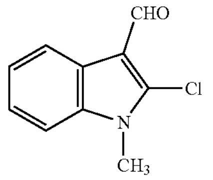

THF (20 mL) was added to 2-chloro-1H-indol-3-carboxaldehyde (359.2 mg, 2.0 mmol) and NaH (120.0 mg, 3.0 mmol, 60% in oil) at 0° C. and stirred for 5 minutes. Then, iodomethane (149.4 μL, 2.4 mmol) was added and stirred at room temperature for 5 hours. The reaction solution was diluted with water and extracted with EA. The organic layer was dried over $MgSO_4$, filtered, and distilled under reduced pressure. The residue was separated by column chromatography ($CH_2Cl_2$:EA=15:1) to obtain 330 mg of the title compound (yield 85%, white solid).

$^1$H NMR (400 MHz, $CDCl_3$): δ 10.13 (s, 1H), 8.30 (m, 1H), 7.36-7.32 (m, 3H), 3.82 (s, 3H); $^{13}$C NMR (100 MHz, DMSO-$d_6$): δ 184.07, 136.99, 136.13, 124.44, 124.20, 123.69, 121.43, 113.02, 109.64, 30.28; MS (MALDI-TOF): m/z 194 $[M+H]^+$; mp 97-98° C.

Preparation Example 13: Ethyl 2-(2-chloro-3-formyl-1H-indol-1-yl)acetate

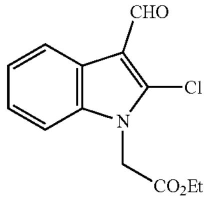

THF (10 mL) was added to 2-chloro-1H-indol-3-carboxaldehyde (200.0 mg, 1.11 mmol) and NaH (66.8 mg, 1.67 mmol, 60% in oil) at 0° C. and stirred for 5 minutes. Then, ethyl bromoacetate (147.5 μL, 1.33 mmol) was added and stirred at room temperature for 7 hours. The reaction solution was diluted with water and extracted with EA. The organic layer was dried over $MgSO_4$, filtered, and distilled under reduced pressure. The residue was separated by column chromatography ($CH_2Cl_2$:EA=20:1) to obtain 244 mg of the title compound (yield 83%, white solid).

$^1$H NMR (400 MHz, $CDCl_3$): δ 10.16 (s, 1H), 8.32 (m, 1H), 7.36-7.32 (m, 2H), 7.23 (m, 1H), 4.95 (s, 2H), 4.26 (q, J=7.2 Hz, 2H), 1.28 (t, J=7.2 Hz, 3H); $^{13}$C NMR (100 MHz, $CDCl_3$): δ 184.09, 166.47, 136.48, 135.70, 124.45, 124.34, 123.78, 121.55, 113.62, 109.03, 62.36, 44.81, 14.05; MS (MALDI-TOF): m/z 266 $[M+H]^+$; mp 110° C.

Preparation Example 14: 2-Chloro-1-(2-ethoxy-ethyl)-1H-indol-3-carboxaldehyde

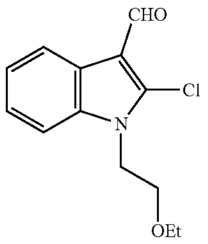 [SMILES: CCOCCn1c(Cl)c(C=O)c2ccccc21]

2-chloro-1H-indol-3-carboxaldehyde (2.69 g, 15.0 mmol) was dissolved in DMF (50 mL), then 2-bromoethyl ethyl ether (2.01 mL, 18.0 mmol) and $Cs_2CO_3$ (14.7 g, 45.0 mmol) were added thereto, and heated at 70° C. for 15 hours. The reaction solution was diluted with water and extracted with EA. The organic layer was dried over $MgSO_4$, filtered, and distilled under reduced pressure. The residue was separated by column chromatography (n-Hex:$CH_2Cl_2$:EA=4:2:1) to obtain 2.95 g of the title compound (yield 78%, pale yellow solid).

$^{1}H$ NMR (400 MHz, $CDCl_3$): δ 10.14 (s, 1H), 8.30 (m, 1H), 7.41 (m, 1H), 7.34-7.30 (m, 2H), 4.42 (t, J=5.6 Hz, 2H), 3.76 (t, J=5.6 Hz, 2H), 3.44 (q, J=7.2 Hz, 2H), 1.12 (t, J=7.2 Hz, 3H); $^{13}C$ NMR (100 MHz, $CDCl_3$): δ 184.09, 136.58, 135.80, 124.41, 123.95, 123.43, 121.24, 113.08, 110.04, 68.13, 66.91, 43.97, 14.97; MS (MALDI-TOF): m/z 252 $[M+H]^+$; mp 52° C.

Preparation Example 15: 2-Chloro-1-(2-methoxy-ethyl)-1H-indol-3-carboxaldehyde

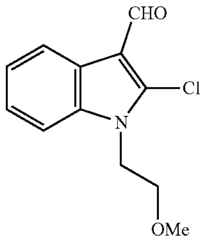 [SMILES: COCCn1c(Cl)c(C=O)c2ccccc21]

2-Chloro-1H-indol-3-carboxaldehyde (538.8 mg, 3.0 mmol) was dissolved in DMF (10 mL), then 2-bromoethyl methyl ether (422.6 μL, 4.5 mmol) and $Cs_2CO_3$ (2.93 g, 9.0 mmol) were added thereto, and heated at 70° C. for 15 hours. The reaction solution was diluted with water and extracted with EA. The organic layer was dried over $MgSO_4$, filtered, and distilled under reduced pressure. The residue was separated by column chromatography (n-Hex:EA=2:1) to obtain 468 mg of the title compound (yield 66%, pale yellow solid). [262]$^{1}H$ NMR (400 MHz, $CDCl_3$): δ 10.14 (s, 1H), 8.30 (m, 1H), 7.42-7.31 (m, 3H), 4.43 (t, J=5.7 Hz, 2H), 3.74 (t, J=5.7 Hz, 2H), 3.32 (s, 3H); $^{13}C$ NMR (100 MHz, $CDCl_3$): δ 184.27, 136.79, 135.97, 124.56, 124.21, 123.64, 121.44, 113.25, 110.17, 70.49, 59.35, 44.00; MS (MALDI-TOF): m/z 238 [M+H]+, 260 $[M+Na]^+$; mp 66-67° C.

Preparation Example 16: 5-Methyloxyindole

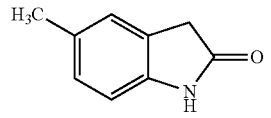

Ethylene glycol (10 mL) was added to 5-methylisatin (1.50 g, 9.31 mmol), then KOH (522.4 mg, 9.31 mmol) and hydrazine monohydrate (1.40 g, 27.9 mmol) were added thereto, and heated at 140° C. for 4 hours. The reaction solution was cooled, acidified with 1N HCl, and extracted with EA. The organic layer was distilled under reduced pressure, and the residue was separated by column chromatography (n-Hex:EA=3:2) to obtain 1.0 g of the title compound (yield 73%, light brown solid).

$^{1}H$ NMR (400 MHz, DMSO-$d_6$): δ 10.23 (br s, 1H), 7.01 (s, 1H), 6.96 (d, J=7.9 Hz, 1H), 6.69 (d, J=7.9 Hz, 1H), 3.41 (s, 2H), 2.23 (s, 3H)

Preparation Example 17: 2-Chloro-5-methyl-1H-indol-3-carboxaldehyde

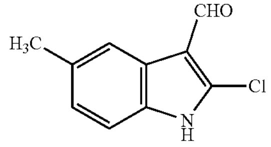

$POCl_3$ (2.65 mL, 28.9 mmol) was added to DMF (10 mL) at 0° C., and stirred for 10 minutes. Then, a solution of 5-methyloxyindole (850.0 mg, 5.78 mmol) in DMF (10 mL) was added and heated at 80° C. for 3 hours. The reaction solution was alkalized by addition of 1N NaOH, and extracted with EA. The organic layer was washed with water, dried over $Na_2SO_4$, filtered, and distilled under reduced pressure. The residue was separated by column chromatography (n-Hex:EA=3:2) to obtain 600 mg of the title compound (yield 54%, pale yellow solid).

$^{1}H$ NMR (400 MHz, DMSO-$d_6$): δ 12.96 (s, 1H), 9.96 (s, 1H), 7.87 (s, 1H), 7.31 (d, J=8.3 Hz), 7.10 (dd, J=8.3, 1.5 Hz, 1H), 2.39 (s, 3H); mp 215° C.

Preparation Example 18: 2-Chloro-1-(2-ethoxy-ethyl)-5-methyl-1H-indol-3-carboxaldehyde

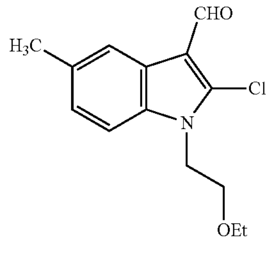 [SMILES: CCOCCn1c(Cl)c(C=O)c2cc(C)ccc21]

To a solution of 2-chloro-5-methyl-1H-indol-3-carboxaldehyde (440.0 mg, 2.27 mmol) in $CH_3CN$ (20 mL), 2-bromoethyl ethyl ether (303.8 μL, 2.72 mmol) and $Cs_2CO_3$ (3.71 g, 11.4 mmol) were added and refluxed for 15 hours. The reaction solution was distilled under reduced pressure, and water was added to the residue, followed by extraction with EA. The organic layer was dried over $MgSO_4$, filtered, and distilled under reduced pressure. The residue was separated by column chromatography (n-Hex:EA=9:1) to obtain 570 mg of the title compound (yield 94%, white solid).

$^1$H NMR (400 MHz, $CDCl_3$): δ 10.09 (s, 1H), 8.10 (s, 1H), 7.28 (d, J=8.5 Hz, 1H), 7.14 (d, J=8.5, 1.5 Hz, 1H), 4.39 (t, J=5.5 Hz, 2H), 3.74 (t, J=5.5 Hz, 2H), 3.43 (q, J=7.0 Hz, 2H), 2.46 (s, 3H), 1.11 (t, J=7.0 Hz, 3H); $^{13}$C NMR (400 MHz, DMSO-$d_6$): δ 184.35, 136.69, 134.28, 133.48, 125.59, 124.73, 121.19, 112.92, 109.89, 68.30, 67.09, 44.19, 21.61, 15.17; MS (MALDI-TOF): m/z 266 [M+H]$^+$; mp 54° C.

Preparation Example 19: 2-Chloro-5-methoxy-1H-indol-3-carboxaldehyde

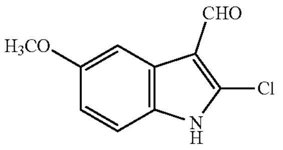 [SMILES: COc1ccc2[nH]c(Cl)c(C=O)c2c1]

$POCl_3$ (2.65 mL g, 24.5 mmol) was added to DMF (10 mL) at 0° C., and stirred for 10 minutes. Then, a solution of 5-methoxyoxyindole (1.60 g, 9.81 mm) in DMF (10 mL) was added and heated at 80° C. for 2 hours. After alkalizing the reaction solution by adding 1N NaOH, the resulting solid was washed with water and dried to obtain the title compound. The filtrate was again extracted with EA, dried over $Na_2SO_4$, filtered, and distilled under reduced pressure. The residue was separated by column chromatography (n-Hex: EA=1:2) to obtain 1.27 g of the title compound (yield 62%, light brown solid).

$^1$H NMR (300 MHz, DMSO-$d_6$): δ 12.96 (br s, 1H), 9.96 (s, 1H), 7.57 (d, J=2.7 Hz, 1H), 7.33 (d, J=8.7 Hz, 1H), 6.90 (dd, J=8.7, 2.7 Hz, 1H), 3.79 (s, 3H); mp 225° C.

Preparation Example 20: 2-Chloro-1-(2-ethoxyethyl)-5-methoxy-1H-indol-3-carboxaldehyde

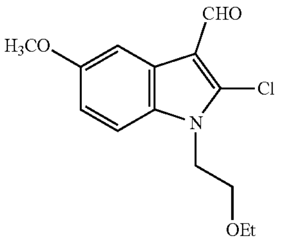 [SMILES: CCOCCn1c(Cl)c(C=O)c2cc(OC)ccc21]

5-Methoxy-2-chloro-1H-indol-3-carboxaldehyde (1.97 g, 9.40 mmol) was dissolved in DMF (70 mL), then 2-bromoethyl ethyl ether (1.26 mL, 11.3 mmol) and $Cs_2CO_3$ (15.3 g, 47.0 mmol) were added thereto, and heated at 70° C. for 11 hours. The reaction solution was diluted with water and extracted with EA. The organic layer was dried over $MgSO_4$, filtered, and distilled under reduced pressure. The residue was separated by column chromatography (n-Hex: EA=3:1) to obtain 2.18 g of the title compound (yield 82%, pale yellow solid).

$^1$H NMR (400 MHz, $CDCl_3$): δ 10.09 (s, 1H), 7.79 (d, J=2.7 Hz, 1H), 7.29 (d, J=9.0 Hz, 1H), 6.94 (dd, J=9.0, 2.7 Hz, 1H), 4.37 (t, J=5.7 Hz, 2H), 3.89 (s, 3H), 3.74 (t, J=5.7 Hz, 2H), 3.43 (q, J=7.2 Hz, 2H), 1.11 (t, J=7.2 Hz, 3H); $^{13}$C NMR (100 MHz, $CDCl_3$): δ 184.10, 156.90, 135.99, 130.59, 125.12, 114.17, 112.95, 111.06, 102.64, 68.21, 66.90, 55.77, 44.16, 14.96; MS (MALDI-TOF): m/z 282 [M+H]$^+$; mp 48° C.

Preparation Example 21: 6-Methoxyoxyindole

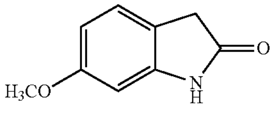 [SMILES: COc1ccc2c(c1)NC(=O)C2]

Ethylene glycol (10 mL) was added to 6-methoxyisatin (500 mg, 2.82 mmol), then KOH (158.2 mg, 2.82 mmol) and hydrazine monohydrate (282.3 mg, 5.64 mmol) were added thereto, and heated at 140° C. for 4 hours. The reaction solution was cooled, acidified with 1N HCl, and extracted with EA. The organic layer was distilled under reduced pressure, and the residue was separated by column chromatography (n-Hex:EA=1:1) to obtain 278 mg of the title compound (yield 60%, pale yellow solid).

$^1$H NMR (400 MHz, DMSO-$d_6$): δ 10.30 (br s, 1H), 7.08 (d, J=8.0 Hz, 1H), 6.48 (d, J=8.0, 2.4 Hz, 1H), 6.38 (d, J=2.4 Hz, 1H), 3.71 (s, 3H), 3.37 (s, 2H)

Preparation Example 22: 2-Chloro-6-methoxy-1H-indol-3-carboxaldehyde

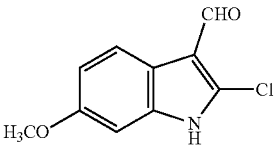 [SMILES: COc1ccc2c(C=O)c(Cl)[nH]c2c1]

$POCl_3$ (1.79 mL g, 19.5 mmol) was added to DMF (5 mL) at 0° C., and stirred for 10 minutes. Then, a solution of 6-methoxyoxyindole (1.27 g, 7.78 mmol) in DMF (15 mL) was added and heated at 80° C. for 2 hours. After alkalizing the reaction solution by adding 1N NaOH, the resulting solid was filtered, washed with water, and dried to obtain the title compound. The filtrate was again extracted with EA, dried over $Na_2SO_4$, filtered, and distilled under reduced pressure. The residue was separated by column chromatography ($CH_2Cl_2$:EA=10:1) to obtain 945 mg of the title compound (yield, white solid). [290]$^1$H NMR (400 MHz, DMSO-$d_6$): δ 12.87 (br s, 1H), 9.94 (s, 1H), 7.91 (m, 1H), 6.89-6.87 (m, 2H), 3.79 (s, 3H); $^{13}$C NMR (100 MHz, DMSO-$d_6$): δ 183.09, 156.90, 135.57, 133.26, 120.73, 118.09, 112.23, 112.10, 95.09, 55.31; mp 230° C.

Preparation Example 23: 2-Chloro-1-(2-ethoxyethyl)-6-methoxy-1H-indol-3-carboxaldehyde

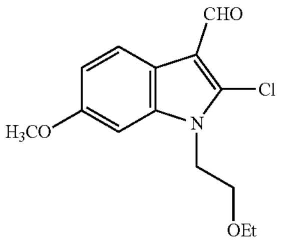 [SMILES: CCOCCn1c(Cl)c(C=O)c2ccc(OC)cc21]

6-Methoxy-2-chloro-1H-indol-3-carboxaldehyde (765.1 mg, 3.65 mmol) was dissolved in DMF (15 mL), then 2-bromoethyl ethyl ether (489.2 μL, 4.38 mmol) and $Cs_2CO_3$ (3.58 g, 11.0 mmol) were added thereto, and heated at 70° C. for 5 hours. The reaction solution was diluted with water and extracted with EA. The organic layer was dried over $MgSO_4$, filtered, and distilled under reduced pressure. The residue was separated by column chromatography (n-Hex:$CH_2Cl_2$:EA=3:1:0.5) to obtain 420 mg of the title compound (yield 41%, white solid).

$^1$H NMR (400 MHz, $CDCl_3$): δ 10.08 (s, 1H), 8.15 (d, J=8.8 Hz, 1H), 6.95 (dd, J=8.8, 2.4 Hz, 1H), 6.89 (d, J=2.4 Hz, 1H), 4.36 (t, J=5.6 Hz, 2H), 3.87 (s, 3H), 3.75 (t, J=5.6 Hz, 2H), 3.45 (q, J=7.2 Hz, 2H), 1.13 (t, J=7.2 Hz, 3H); $^{13}$C NMR (100 MHz, DMSO-$d_6$): δ 184.02, 157.51, 136.85, 135.25, 122.00, 118.29, 113.20, 112.31, 94.46, 68.25, 66.92, 55.68, 44.00, 15.04; MS (MALDI-TOF): m/z 281 $[M]^+$; mp 82° C.

Preparation Example 24: 2-Chloro-5-fluoro-1H-indol-3-carboxaldehyde

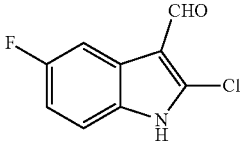 [SMILES: O=Cc1c(Cl)[nH]c2ccc(F)cc12]

$POCl_3$ (1.36 mL g, 14.9 mmol) was added to DMF (5 mL) at 0° C., and stirred for 10 minutes. Then, a solution of 5-fluorooxyindole (900.0 mg, 5.95 mmol) in DMF (15 mL) was added and heated at 80° C. for 4 hours. The reaction solution was alkalized by addition of 1N NaOH, and extracted with EA. The organic layer was dried over $Na_2SO_4$, filtered, and distilled under reduced pressure. The residue was separated by column chromatography (n-Hex: EA=1:1) to obtain 235 mg of the title compound (yield 20%, white solid).

$^1$H NMR (300 MHz, DMSO-$d_6$): δ 13.22 (br s, 1H), 9.96 (s, 1H), 7.73 (dd, J=9.0, 2.7 Hz, 1H), 7.45 (dd, J=9.0, 4.5 Hz, 1H), 7.13 (m, 1H); $^{13}$C NMR (100 MHz, DMSO-$d_6$): δ 183.27, 158.93 (d, J=235.2 Hz), 135.60, 131.21, 124.89 (d, J=11.3 Hz), 113.27 (d, J=9.9 Hz), 112.11 (d, J=4.4 Hz), 111.92 (d, J=25.9 Hz), 105.09 (d, J=25.1 Hz); mp 208-210° C.

Preparation Example 25: 2-Chloro-1-(2-ethoxyethyl)-5-fluoro-1H-indol-3-carboxaldehyde

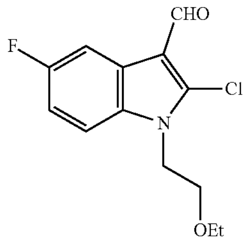 [SMILES: CCOCCn1c(Cl)c(C=O)c2cc(F)ccc21]

2-Chloro-5-fluoro-1H-indol-3-carboxaldehyde (197.6 mg, 1.0 mmol) was dissolved in DMF (5 mL), then 2-bromoethyl ethyl ether (134.0 μL, 1.2 mmol) and $Cs_2CO_3$ (977.5 mg, 3.0 mmol) were added thereto, and heated at 70° C. for 15 hours. The reaction solution was diluted with water and extracted with EA. The organic layer was dried over $MgSO_4$, filtered, and distilled under reduced pressure. The residue was separated by column chromatography (n-Hex: $CH_2Cl_2$:EA=3:1:0.5) to obtain 125 mg of the title compound (yield 46%, white solid).

$^1$H NMR (400 MHz, $CDCl_3$): δ 10.09 (s, 1H), 7.98 (d, J=9.2, 2.4 Hz, 1H), 7.36 (d, J=9.2, 4.4 Hz, 1H), 7.06 (m, 1H), 4.41 (t, J=5.6 Hz, 2H), 3.76 (t, J=5.6 Hz, 2H), 3.43 (q, J=7.2 Hz, 2H), 1.11 (t, J=7.2 Hz, 3H); $^{13}$C NMR (400 MHz, DMSO-$d_6$): δ 183.79, 159.96 (d, J=238.6 Hz), 137.13, 132.38, 124.95 (d, J=11.3 Hz), 113.07 (d, J=4.4 Hz), 112.19 (d, J=26.2 Hz), 111.30 (d, J=9.4 Hz), 106.80 (d, J=25.1 Hz), 68.23, 66.91, 44.37, 14.93; MS (MALDI-TOF): m/z 270 $[M+H]^+$; mp 83-84° C.

Preparation Example 26: 2,5-Dichloro-1H-indol-3-carboxaldehyde

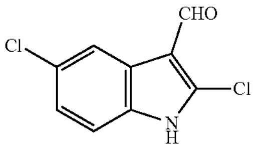 [SMILES: O=Cc1c(Cl)[nH]c2ccc(Cl)cc12]

$POCl_3$ (2.74 mL, 29.9 mmol) was added to DMF (5 mL) at 0° C., and stirred for 10 minutes. Then, a solution of 5-chlorooxyindole (1.0 g, 5.97 mmol) in DMF (5 mL) was added and heated at 80° C. for 3 hours. The reaction solution was alkalized by addition of 1 N NaOH, and extracted with EA. The organic layer was washed with water, dried over $Na_2SO_4$, filtered, and distilled under reduced pressure. The residue was separated by column chromatography (n-Hex: EA=2:1) to obtain 530 mg of the title compound (yield 41%, light brown solid).

$^1$H NMR (400 MHz, DMSO-$d_6$): δ 13.31 (br s, 1H), 9.97 (s, 1H), 8.04 (d, J=2.0 Hz, 1H), 7.47 (d, J=8.5 Hz, 1H), 7.31 (dd, J=8.5, 2.0 Hz, 1H); mp 245-248° C.

Preparation Example 27: 2,5-Dichloro-1-(2-ethoxyethyl)-1H-indol-3-carboxaldehyde

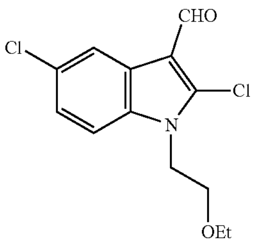 [SMILES: CCOCCn1c(Cl)c(C=O)c2cc(Cl)ccc21]

To a solution in which 2,5-dichloro-1H-indol-3-carboxaldehyde (350 mg, 1.64 mmol) obtained in Preparation Example 26 was dissolved in $CH_3CN$ (20 mL), 2-bromoethyl ethyl ether (274.8 μL, 2.46 mmol) and $Cs_2CO_3$ (2.67 g, 8.20 mmol) were added and refluxed for 15 hours. The reaction solution was distilled under reduced pressure, and water was added to the residue, followed by extraction with EA. The organic layer was dried over $MgSO_4$, filtered, and distilled under reduced pressure. The residue was separated by column chromatography (n-Hex:EA=9:1) to obtain 360 mg of the title compound (yield 77%, pale yellow solid).

$^1H$ NMR (400 MHz, $CDCl_3$): δ 10.06 (s, 1H), 8.26 (d, J=2.0 Hz, 1H), 7.32-7.23 (m, 2H), 4.38 (t, J=5.6 Hz, 2H), 3.73 (t, J=5.6 Hz, 2H), 3.41 (q, J=7.2 Hz, 2H), 1.08 (t, J=7.2 Hz, 3H); $^{13}C$ NMR (100 MHz, DMSO-$d_6$): δ 184.01, 137.39, 134.50, 129.64, 125.40, 124.51, 120.95, 112.84, 111.60, 68.41, 67.13, 44.55, 15.15; MS (MALDI-TOF): m/z 286 $[M+H]^+$; mp 104° C.

Preparation Example 28: 5-(Trifluoromethoxy)oxyindole

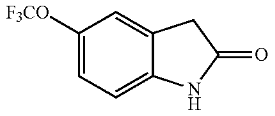 [SMILES: O=C1Cc2cc(OC(F)(F)F)ccc2N1]

Ethylene glycol (10 mL) was added to 5-(trifluoromethoxy)isatin (1.75 g, 7.57 mmol), then KOH (424.8 mg, 7.57 mmol) and hydrazine monohydrate (1.14 g, 22.7 mmol) were added thereto, and heated at 140° C. for 4 hours. The reaction solution was cooled, acidified with 1 N HCl, and extracted with EA. The organic layer was distilled under reduced pressure, and the residue was separated by column chromatography (n-Hex:EA=1:2) to obtain 855 mg of the title compound (yield 52%, light brown solid).

$^1H$ NMR (400 MHz, DMSO-$d_6$): δ 10.52 (br s, 1H), 7.24 (s, 1H), 7.16 (m, 1H), 6.86 (d, J=8.0 Hz, 1H), 3.54 (s, 2H)

Preparation Example 29: 2-Chloro-5-(trifluoromethoxy)-1H-indol-3-carboxaldehyde

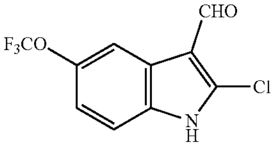 [SMILES: O=Cc1c(Cl)[nH]c2ccc(OC(F)(F)F)cc12]

$POCl_3$ (727.7 μL g, 7.95 mmol) was added to DMF (1 mL) at 0° C., and stirred for 10 minutes. Then, a solution of 5-(trifluoromethoxy)oxyindole (575.0 mg, 2.65 mmol) in DMF (5 mL) was added and heated at 80° C. for 3 hours. The reaction solution was alkalized by addition of 1 N NaOH, and extracted with EA. The organic layer was dried over $Na_2SO_4$, filtered, and distilled under reduced pressure. The residue was separated by column chromatography (n-Hex:EA=1:1) to obtain 120 mg of the title compound (yield 17%, white solid).

$^1H$ NMR (400 MHz, DMSO-$d_6$): δ 13.40 (br s, 1H), 9.99 (s, 1H), 7.95 (m, 1H), 7.54 (d, J=8.8 Hz, 1H), 7.29 (m, 1H); mp 191-192° C.

Preparation Example 30: 2-Chloro-1-(2-ethoxyethyl)-5-(trifluoromethoxy)-1H-indol-3-carboxaldehyde

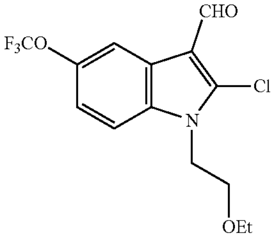 [SMILES: CCOCCn1c(Cl)c(C=O)c2cc(OC(F)(F)F)ccc21]

2-Chloro-5-(trifluoromethoxy)-1H-indol-3-carboxaldehyde (100 mg, 0.38 mmol) was dissolved in DMF (3 mL), then 2-bromoethyl ethyl ether (51.4 μL, 0.46 mmol) and $Cs_2CO_3$ (371.4 mg, 1.14 mmol) were added thereto, and heated at 70° C. for 8 hours. The reaction solution was diluted with water and extracted with EA. The organic layer was dried over $MgSO_4$, filtered, and distilled under reduced pressure. The residue was separated by column chromatography (n-Hex:$CH_2Cl_2$:EA=4:4:1) to obtain 43 mg of the title compound (yield 34%, pale yellow solid).

$^1H$ NMR (400 MHz, $CDCl_3$): δ 10.11 (s, 1H), 8.18 (s, 1H), 7.42 (d, J=8.8 Hz, 1H), 7.20 (dd, J=8.8, 1.6 Hz, 1H), 4.42 (t, J=5.6 Hz, 2H), 3.77 (t, J=5.6 Hz, 2H), 3.44 (q, J=5.2 Hz, 2H), 1.11 (t, J=7.2 Hz, 3H); $^{13}C$ NMR (100 MHz, $CDCl_3$): δ 183.78, 145.66 (q, J=1.9 Hz), 137.58, 134.20, 124.73, 120.62 (q, J=255.0 Hz), 117.81, 113.86 (q, J=0.8 Hz), 113.23, 111.29, 68.25, 66.96, 44.46, 14.94; MS (MALDI-TOF): m/z 335 $[M]^+$; mp 79° C.

Preparation Example 31: 2-Bromo-1H-indol-3-carboxaldehyde

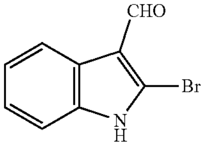 [SMILES: O=Cc1c(Br)[nH]c2ccccc12]

DMF (1.8 mL) was added to $CH_2Cl_2$ (6 mL) at 0° C., and then a solution of $POBr_3$ (5.33 g, 18.6 mmol) in $CH_2Cl_2$ (10 mL) was slowly added and refluxed for 15 minutes. Thereafter, oxyindole (1.03 g, 7.74 mmol) was added little by little, and the mixture was refluxed for 1 hour more. The reaction solution was put in cold water and stirred for 20 minutes to separate the water layer. The water layer was neutralized with solid $K_2CO_3$ and the resulting solid was filtered. The obtained solid was purified by column chromatography (n-Hex:EA=2:1) to obtain 1.2 g of the title compound (yield 70%, light brown solid).

$^1$H NMR (400 MHz, DMSO-$d_6$): δ 13.04 (br s, 1H), 9.90 (s, 1H), 8.08 (m, 1H), 7.43 (m, 1H), 7.29-7.21 (m, 2H)

Preparation Example 32: Ethyl 2-(2-bromo-3-formyl-1H-indol-1-yl)acetate

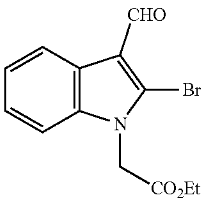

THF (5 mL) and DMF (2 mL) were added to 2-bromo-1H-indol-3-carboxaldehyde (120.0 mg, 0.54 mmol) obtained in Preparation Example 31 and NaH (32.4 mg, 0.81 mmol, 60% in oil) at 0° C. and stirred for 5 minutes. Then, ethyl bromoacetate (72.1 μL, 0.65 mmol) was added and stirred at room temperature for 15 hours. The reaction solution was diluted with water and extracted with EA. The organic layer was dried over $MgSO_4$, filtered, and distilled under reduced pressure. The residue was separated by column chromatography ($CH_2Cl_2$:EA=20:1) to obtain 91 mg of the title compound (yield 54%, white solid).

$^1$H NMR (400 MHz, $CDCl_3$): δ 10.07 (s, 1H), 8.33 (m, 1H), 7.34-7.31 (m, 2H), 7.25 (m, 1H), 4.99 (s, 2H), 4.26 (q, J=7.2 Hz, 2H), 1.28 (t, J=7.2 Hz, 3H); $^{13}$C NMR (100 MHz, $CDCl_3$): δ 185.45, 166.55, 137.11, 126.09, 125.18, 124.49, 123.62, 121.40, 116.07, 109.21, 62.35, 46.27, 14.06; MS (MALDI-TOF): m/z 309 $[M]^+$; mp 94° C.

Preparation Example 33: 2-Bromo-1-(2-ethoxyethyl)-1H-indol-3-carboxaldehyde

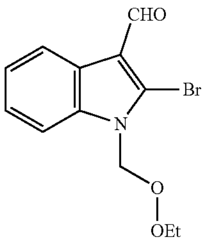 [SMILES: CCOOCn1c(Br)c(C=O)c2ccccc21]

2-Bromo-1H-indol-3-carboxaldehyde (400.0 mg, 1.79 mmol) obtained in Preparation Example 31 was dissolved in DMF (10 mL), then 2-bromoethyl ethyl ether (240.1 μL, 2.15 mmol) and $Cs_2CO_3$ (1.75 g, 5.37 mmol) were added thereto, and heated at 70° C. for 6 hours. The reaction solution was diluted with water and extracted with EA. The organic layer was dried over $MgSO_4$, filtered, and distilled under reduced pressure. The residue was separated by column chromatography ($CH_2Cl_2$:EA=20:1) to obtain 436 mg of the title compound (yield 82%, white solid).

$^1$H NMR (400 MHz, $CDCl_3$): δ 10.06 (s, 1H), 8.32 (m, 1H), 7.43 (m, 1H), 7.34-7.30 (m, 2H), 4.46 (t, J=5.6 Hz, 2H), 3.77 (t, J=5.6 Hz, 2H), 3.45 (q, J=7.2 Hz, 2H), 1.23 (t, J=7.2 Hz, 3H); $^{13}$C NMR (100 MHz, $CDCl_3$): δ 185.61, 137.43, 126.59, 125.43, 124.25, 123.57, 121.30, 115.60, 110.47, 68.40, 67.14, 45.59, 15.17; MS (MALDI-TOF): m/z 295 $[M]^+$; mp 56-57° C.

Preparation Example 34: 2-(Trifluoromethyl)-1H-indol-3-carboxaldehyde

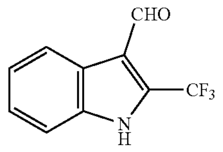 [SMILES: O=Cc1c(C(F)(F)F)[nH]c2ccccc12]

$POCl_3$ (1.83 mL g, 20.0 mmol) was added to DMF (10 mL) at 0° C., and stirred for 10 minutes. Then, a solution of 2-trifluoromethylindole (740.6 mg, 4.0 mmol) in DMF (10 mL) was added and heated at 80° C. for 5 hours. The reaction solution was alkalized by addition of 1 N NaOH, and extracted with EA. The organic layer was washed with brine, dried over $Na_2SO_4$, filtered, and distilled under reduced pressure. The residue was separated by column chromatography (n-Hex:EA=7:1) to obtain 324 mg of the title compound (yield 38%, white solid).

$^1$H NMR (400 MHz, DMSO-$d_6$): δ 13.42 (br s, 1H), 10.24 (s, 1H), 8.25 (d, J=8.0 Hz, 1H), 7.61 (d, J=8.0 Hz, 1H), 7.44 (m, 1H), 7.36 (m, 1H); mp 171-173° C.

Preparation Example 35: 1-(2-Ethoxyethyl)-2-(trifluoromethyl)-1H-indol-3-carboxaldehyde

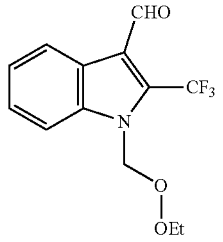 [SMILES: CCOOCn1c(C(F)(F)F)c(C=O)c2ccccc21]

2-(Trifluoromethyl)-1H-indol-3-carboxaldehyde (350.0 mg, 1.64 mmol) was dissolved in DMF (10 mL), then 2-bromoethyl ethyl ether (220.0 μL, 1.97 mmol) and $Cs_2CO_3$ (1.60 g, 4.92 mmol) were added thereto, and heated at 70° C. for 15 hours. The reaction solution was diluted with water and extracted with EA. The organic layer was dried over $MgSO_4$, filtered, and distilled under reduced pressure. The residue was separated by column chromatography (n-Hex:EA=5:1) to obtain 184 mg of the title compound (yield 39%, white solid).

$^1$H NMR (400 MHz, $CDCl_3$): δ 10.41 (s, 1H), 8.52 (d, J=8.0 Hz, 1H), 7.58 (d, J=8.0 Hz, 1H), 7.46 (m, 1H), 7.39 (m, 1H), 4.52 (t, J=6.0 Hz, 2H), 3.80 (t, J=6.0 Hz, 2H), 3.45 (q, J=7.2 Hz, 2H), 1.13 (t, J=7.2 Hz, 3H); $^{13}$C NMR (100 MHz, $CDCl_3$): δ 185.81, 137.63, 131.27 (q, J=37.9 Hz), 126.02, 124.30, 124.21, 123.66, 121.29 (q, J=270.3 Hz), 117.84 (q, J=1.5 Hz), 111.18, 68.82, 66.93, 45.58 (q, J=2.5 Hz), 14.94; MS (MALDI-TOF): m/z 286 $[M+H]^+$; mp 46° C.

Preparation of benzofuran-based N-acylhydrazone Derivative

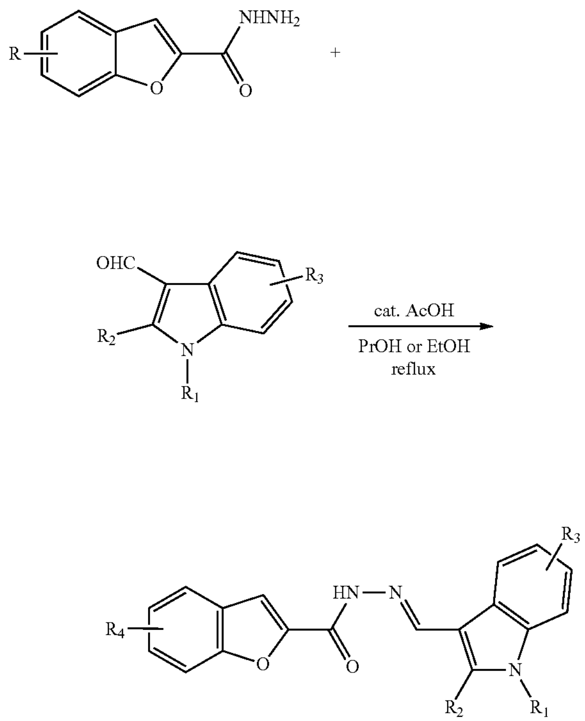

$R_1$ = H, $CH_3$, —$CH_2CO_2Et$, —$CH_2CH_2OEt$, —$CH_2CH_2OMe$ $R_2$ = Cl, Br, $CF_3$
$R_3$ = H, 5-$CH_3$, 5-$OCH_3$, 6-$OCH_3$, 5-F, 5-Cl, 5-$OCF_3$ $R_4$ = 5- $CH_3$, 5-$OCH_3$, 5-Cl, 4,7-Dimethyl, 4,6-Dimethoxy 5-$HNCOCH_3$ Example 1: Preparation of (E)-N'-[(2-chloro-1H-indol-3-yl)methylene]-5-methylbenzofuran-2-carbohydrazide (CAP-1052, Compound 7)

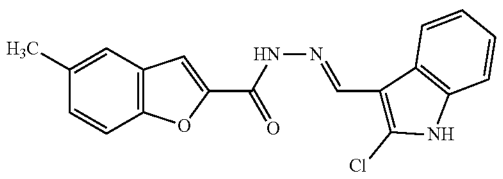 [SMILES: Cc1ccc2oc(C(=O)N/N=C/c3c(Cl)[nH]c4ccccc34)cc2c1]

To 5-methylbenzofuran-2-carbohydrazide (95.1 mg, 0.50 mmol) and 2-chloro-1H-indol-3-carboxaldehyde (89.8 mg, 0.50 mmol), 1-PrOH (15 mL) and acetic acid (1-2 drops) were added and refluxed for 8 hours. The reaction solution was distilled under reduced pressure, and the residue was washed with a mixed solvent of n-Hex/$CH_2Cl_2$ (1:1) to obtain 153 mg of the title compound (yield 87%, pale yellow solid). [348]$^1$H NMR (300 MHz, DMSO-$d_6$) δ 12.48 (s, 1H), 11.98 (s, 1H), 8.73 (s, 1H), 8.28 (d, J=7.2 Hz, 1H), 7.63-7.58 (m, 3H), 7.39 (d, J=7.2 Hz, 1H), 7.32 (d, J=8.8 Hz, 1H), 7.27-7.19 (m, 2H), 2.44 (s, 3H); $^{13}$C NMR (100 MHz, DMSO-$d_6$) δ 154.20, 152.86, 148.41, 142.86, 135.02, 132.91, 128.33, 127.26, 127.16, 124.06, 123.20, 122.24, 121.33, 121.28, 111.37, 111.21, 110.03, 107.39, 20.83; HRMS (TOF MS $ES^-$): m/z calcd for $C_{19}H_{13}ClN_3O_2$(M−H)$^-$ 350.0696, found 350.0700; mp 242° C.

Example 2: Preparation of (E)-N'-[(2-chloro-1-methyl-1H-indol-3-yl)methylene]-5-methylbenzofuran-2-carbohydrazide (CAP-1041, Compound 13)

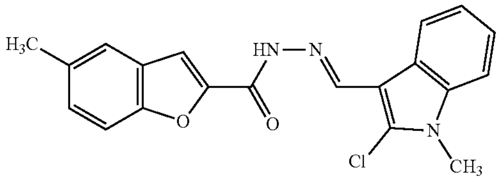 [SMILES: Cc1ccc2oc(C(=O)N/N=C/c3c(Cl)n(C)c4ccccc34)cc2c1]

To 5-methylbenzofuran-2-carbohydrazide (95.1 mg, 0.50 mmol) and 2-chloro-1-methyl-1H-indol-3-carboxaldehyde (96.8 mg, 0.50 mmol), 1-PrOH (15 mL) and acetic acid (1-2 drops) were added and refluxed for 24 hours. The reaction solution was cooled, and the solid was filtered and washed with EtOH to obtain 100 mg of the title compound (yield 55%, light brown solid).

$^1$H NMR (400 MHz, DMSO-$d_6$): δ 12.00 (s, 1H), 8.75 (s, 1H), 8.32 (d, J=7.6 Hz, 1H), 7.63-7.57 (m, 4H), 7.35-7.25 (m, 3H), 3.81 (s, 3H), 2.43 (s, 3H); $^{13}$C NMR (100 MHz, DMSO-$d_6$): δ 154.22, 152.87, 148.40, 142.93, 136.08, 132.92, 129.29, 128.34, 127.16, 123.24, 123.21, 122.25, 121.67, 121.42, 111.38, 110.34, 110.06, 107.28, 30.19, 20.84; HRMS (TOF MS $ES^-$): m/z calcd for $C_{20}H_{15}ClN_3O_2$ (M−H)$^+$ 364.0853, found 364.0847; mp 246-247° C.

Example 3: Preparation of ethyl (E)-2-{2-chloro-3-[(2-(5-methylbenzofuran-2-carbonyl)hydrazinylidene)methyl]-1H-indol-1-yl}acetate (CAP-1038, Compound 12)

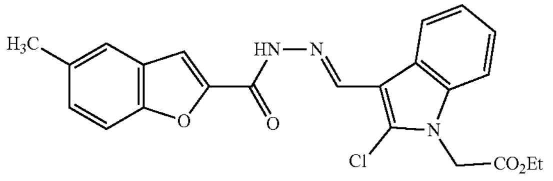 [SMILES: CCOC(=O)Cn1c(Cl)c(/C=N/NC(=O)c2cc3cc(C)ccc3o2)c2ccccc21]

To 5-methylbenzofuran-2-carbohydrazide (60.9 mg, 0.32 mmol) and ethyl 2-(2-chloro-3-formyl-1H-indol-1-yl)acetate (85.0 mg, 0.32 mmol), 1-PrOH (15 mL) and acetic acid (1-2 drops) were added and refluxed for 30 hours. The reaction solution was distilled under reduced pressure, and the residue was washed with $Et_2O$ to obtain 85 mg of the title compound (yield 61%, white solid). [356]$^1$H NMR (400 MHz, DMSO-$d_6$): δ 12.06 (s, 1H), 8.76 (s, 1H), 8.34 (d, J=6.8 Hz, 1H), 7.64-7.58 (m, 4H), 7.34-7.27 (m, 3H), 5.26 (s, 2H), 4.19 (q, J=7.2 Hz, 2H), 2.43 (s, 3H), 1.22 (t, J=7.2 Hz, 3H); $^{13}$C NMR (100 MHz, DMSO-$d_6$): δ 167.84, 154.28, 152.88, 148.33, 142.65, 136.14, 132.94, 129.17, 128.39, 127.15, 123.57, 123.29, 122.27, 121.97, 121.49, 111.39, 110.30, 110.19, 108.22, 61.45, 44.78, 20.84, 14.00; HRMS (TOF MS $ES^-$): m/z calcd for $C_{23}H_{19}ClN_3O_4$ (M−H)$^-$ 436.1064, found 436.1068; mp 198° C.

Example 4: Preparation of (E)-N'-[(2-chloro-1-(2-ethoxyethyl)-1H-indol-3-yl]methylene}-5-methyl-benzofuran-2-carbohydrazide (CAP-1042, Compound 1)

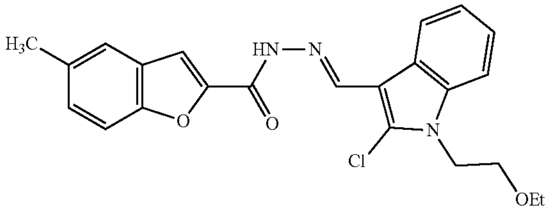 [SMILES: CCOCCn1c(Cl)c(/C=N/NC(=O)c2cc3cc(C)ccc3o2)c2ccccc21]

To 5-methylbenzofuran-2-carbohydrazide (98.9 mg, 0.52 mmol) and 2-chloro-1-(2-ethoxyethyl)-1H-indol-3-carboxaldehyde (130.9 mg, 0.52 mmol), 1-PrOH (15 mL) and acetic acid (1-2 drops) were added and refluxed for 24 hours. The reaction solution was distilled under reduced pressure, and the residue was separated by column chromatography (n-Hex:EA=1:1) to obtain 179 mg of the title compound (yield 81%, pale yellow solid).

$^{1}$H NMR (400 MHz, DMSO-$d_6$): δ 12.01 (s, 1H), 8.75 (s, 1H), 8.32 (d, J=7.6 Hz, 1H), 7.63-7.58 (m, 4H), 7.33-7.24 (m, 3H), 4.46 (t, J=5.6 Hz, 2H), 3.71 (t, J=5.6 Hz, 2H), 3.39 (q, J=6.8 Hz, 2H), 2.43 (s, 3H), 1.00 (t, J=6.8 Hz, 3H); $^{13}$C NMR (100 MHz, DMSO-$d_6$): δ 154.23, 152.87, 148.40, 142.99, 135.76, 132.92, 129.26, 128.34, 127,16, 123.35, 123.21, 122.25, 121.67, 121.43, 111.37, 110.67, 110.08, 107.53, 67.85, 65.63, 43.52, 20.83, 14.90; HRMS (TOF MS ES$^-$): m/z calcd for $C_{23}H_{21}ClN_3O_3(M-H)^-$ 422.1271, found 422.1261; mp 172° C.

Example 5: Preparation of (E)-N'-[(2-bromo-1-(2-ethoxyethyl)-1H-indol-3-yl]methylene}-5-methyl-benzofuran-2-carbohydrazide (CAP-1044, Compound 14)

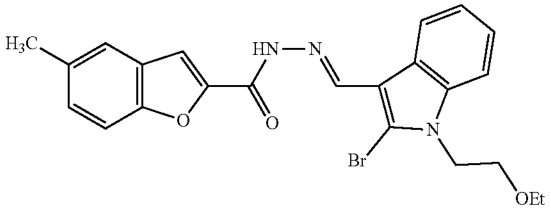 [SMILES: CCOCCn1c(Br)c(/C=N/NC(=O)c2cc3cc(C)ccc3o2)c2ccccc21]

To 5-methylbenzofuran-2-carbohydrazide (108.4 mg, 0.57 mmol) and 2-bromo-1-(2-ethoxyethyl)-1H-indol-3-carboxaldehyde (168.8 mg, 0.57 mmol), 1-PrOH (15 mL) and acetic acid (1-2 drops) were added and refluxed for 24 hours. The reaction solution was distilled under reduced pressure, dissolved in a small amount of $CH_2Cl_2$, and then added dropwise to n-Hex solution. The resulting solid was filtered to obtain 209 mg of the title compound (yield 78%, pale yellow solid). [364]$^{1}$H NMR (400 MHz, DMSO-$d_6$): δ 12.03 (s, 1H), 8.72 (s, 1H), 8.35 (d, J=7.2 Hz, 1H), 7.63-7.58 (m, 4H), 7.33-7.22 (m, 3H), 4.48 (t, J=5.6 Hz, 2H), 3.71 (t, J=5.6 Hz, 2H), 3.39 (q, J=7.2H, 2H), 2.44 (s, 3H), 1.01 (t, J=7.2 Hz, 3H); $^{13}$C NMR (100 MHz, DMSO-$d_6$): δ 154.21, 152.86, 148.41, 144.36, 137.00, 132.90, 128.32, 127.16, 124.14, 123.13, 122.23, 121.46, 121.29, 119.80, 111.36, 110.77, 110.43, 110.03, 67.96, 65.69, 44.81, 20.83, 14.91; HRMS (TOF MS ES$^-$): m/z calcd for $C_{23}H_{21}BrN_3O_3$ $(M-H)^-$ 466.0766, found 466.0776; mp 190° C.

Example 6: Preparation of (E)-N'-{[1-(2-ethoxy-ethyl)-2-(trifluoromethyl)-1H-indol-3-yl]methyl-ene}-5-methylbenzofuran-2-carbohydrazide (CAP-1045, Compound 15)

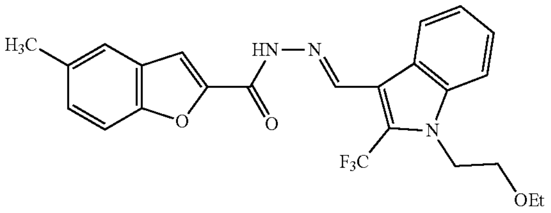 [SMILES: CCOCCn1c(C(F)(F)F)c(/C=N/NC(=O)c2cc3cc(C)ccc3o2)c2ccccc21]

To 5-methylbenzofuran-2-carbohydrazide (93.2 mg, 0.49 mmol) and 1-(2-ethoxyethyl)-2-trifluoromethyl-1H-indol-3-carboxaldehyde (139.8 mg, 0.49 mmol), 1-PrOH (15 mL) and acetic acid (1-2 drops) were added and refluxed for 24 hours. The reaction solution was distilled under reduced pressure, and the residue was separated by column chromatography (n-Hex:EA=2:1) to obtain 176 mg of the title compound (yield 79%, white solid).

$^{1}$H NMR (400 MHz, DMSO-$d_6$): δ 12.24 (s, 1H), 9.00 (s, 1H), 8.63 (d, J=8.0 Hz, 1H), 7.75 (d, J=8.4 Hz, 1H), 7.67 (s, 1H), 7.61-7.59 (m, 2H), 7.47 (m, 1H), 7.37-7.32 (m, 2H), 4.54 (t, J=5.4 Hz, 2H), 3.72 (t, J=5.4 Hz, 2H), 3.37 (q, J=7.0 Hz, 2H), 2.44 (s, 3H), 10.00 (t, J=7.0 Hz, 3H); $^{13}$C NMR (100 MHz, DMSO-$d_6$): δ 154.52, 152.93, 148.17, 142.47, 137.83, 133.01, 128.53, 127.12, 125.66, 125.10 (q, J=35.8 Hz), 124.20, 123.14, 122.48, 122.32, 121.75 (q, J=269.0 Hz), 113.45, 111.85, 111.42, 110.56, 68.36, 65.79, 45.01, 20.84, 14.85; $^{19}$F NMR (376 MHz, DMSO-$d_6$): 5-52.9 (s, 3F); HRMS (TOF MS ES$^-$): m/z calcd for $C_{24}H_{21}F_3N_3O_3$ $(M-H)^-$ 456.1535, found 456.1531; mp 183° C.

Example 7: Preparation of (E)-N'-[(2-chloro-1-(2-methoxyethyl)-1H-indol-3-yl]methylene}-5-methyl-benzofuran-2-carbohydrazide (CAP-1070, Compound 19)

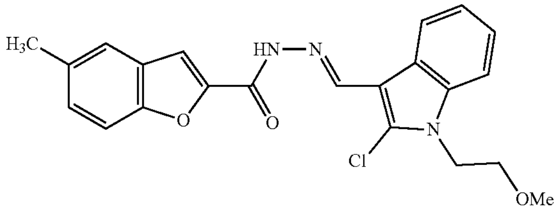 [SMILES: COCCn1c(Cl)c(/C=N/NC(=O)c2cc3cc(C)ccc3o2)c2ccccc21]

To 5-methylbenzofuran-2-carbohydrazide (319.5 mg, 1.68 mmol) and 2-chloro-1-(2-methoxyethyl)-1H-indol-3-carboxaldehyde (399.3 mg, 1.68 mmol), 1-PrOH (20 mL) and acetic acid (1-2 drops) were added and refluxed for 15 hours. The reaction solution was cooled, and the solid was filtered and washed with n-Hex to obtain 630 mg of the title compound (yield 91%, pale yellow solid).

$^{1}$H NMR (400 MHz, DMSO-$d_6$): δ 12.01 (s, 1H), 8.75 (s, 1H), 8.33 (d, J=7.5 Hz, 1H), 7.63-7.58 (m, 4H), 7.33-7.24

(m, 3H), 4.48 (t, J=5.4 Hz, 2H), 3.68 (t, J=5.4 Hz, 2H), 3.21 (s, 3H), 2.43 (s, 3H); $^{13}C$ NMR (100 MHz, DMSO-$d_6$): δ 154.23, 152.88, 148.40, 142.97, 135.76, 132.93, 129.20, 128.36, 127.16, 123.34, 123.25, 122.25, 121.68, 121.44, 111.38, 110.68, 110.10, 107.55, 70.11, 58.29, 43.34, 20.84; HRMS (TOF MS ES$^-$): m/z calcd for $C_{22}H_{19}ClN_3O_3$ $(M-H)^-$ 408.1115, found 408.1099; mp 243° C.

Example 8: Preparation of (E)-N'-[(2-chloro-1-(2-ethoxyethyl)-5-methoxy-1H-indol-3-yl]methylene}-5-methylbenzofuran-2-carbohydrazide (CAP-1046, Compound 2)

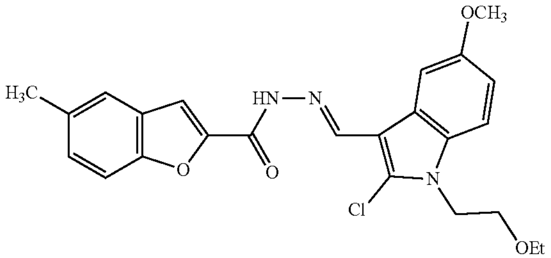 [SMILES: CCOCCn1c(Cl)c(/C=N/NC(=O)c2cc3cc(C)ccc3o2)c2cc(OC)ccc21]

To 5-methylbenzofuran-2-carbohydrazide (127.4 mg, 0.67 mmol) and 2-chloro-1-(2-ethoxyethyl)-5-methoxy-1H-indol-3-carboxaldehyde (188.8 mg, 0.67 mmol), 1-PrOH (15 mL) and acetic acid (1-2 drops) were added and refluxed for 24 hours. The reaction solution was distilled under reduced pressure, and the residue was separated by column chromatography (n-Hex:EA=1:2) to obtain 213 mg of the title compound (yield 70%, pale yellow solid).

$^1H$ NMR (400 MHz, DMSO-$d_6$): δ 12.01 (s, 1H), 8.73 (s, 1H), 7.91 (d, J=2.4 Hz, 1H), 7.61-7.57 (m, 3H), 7.52 (d, J=9.2 Hz, 1H), 7.32 (dd, J=8.8, 1.6 Hz, 1H), 6.95 (dd, J=8.8, 2.4 Hz, 1H), 4.42 (t, J=5.2 Hz, 2H), 3.82 (s, 3H), 3.68 (t, J=5.2 Hz, 2H), 3.38 (q, J=7.2 Hz, 2H), 2.43 (s, 3H), 1.00 (t, J=7.2 Hz, 3H); $^{13}C$ NMR (400 MHz, DMSO-$d_6$): δ 155.20, 154.17, 152.85, 148.48, 142.94, 132.91, 130.74, 128.95, 128.31, 127.17, 124.01, 122.23, 112.24, 111.53, 111.35, 110.04, 107.24, 104.11, 67.91, 65.62, 55.33, 43.65, 20.83, 14.90; HRMS (TOF MS ES$^-$): m/z calcd for $C_{24}H_{23}ClN_3O_4$ $(M-H)^-$ 452.1377, found 452.1355; mp 208° C.

Example 9: Preparation of (E)-N'-[(2-chloro-1-(2-ethoxyethyl)-6-methoxy-1H-indol-3-yl]methylene}-5-methylbenzofuran-2-carbohydrazide (CAP-1050, Compound 6)

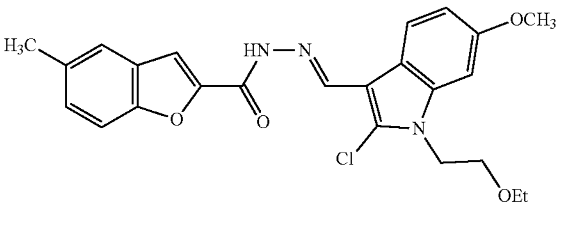 [SMILES: CCOCCn1c(Cl)c(/C=N/NC(=O)c2cc3cc(C)ccc3o2)c2ccc(OC)cc21]

To 5-methylbenzofuran-2-carbohydrazide (95.1 mg, 0.50 mmol) and 2-chloro-1-(2-ethoxyethyl)-6-methoxy-1H-indol-3-carboxaldehyde (140.9 mg, 0.50 mmol), 1-PrOH (15 mL) and acetic acid (1-2 drops) were added and refluxed for 16 hours. The reaction solution was distilled under reduced pressure, dissolved in a small amount of $CH_2Cl_2$, and then added dropwise to n-Hex solution. The resulting solid was filtered to obtain 205 mg of the title compound (yield 90%, pale yellow solid).

$^1H$ NMR (400 MHz, DMSO-$d_6$): δ 11.98 (s, 1H), 8.70 (s, 1H), 8.16 (d, J=8.8 Hz, 1H), 7.62-7.58 (m, 3H), 7.32 (dd, J=8.4, 1.2 Hz, 1H), 7.17 (d, J=2.0 Hz, 1H), 6.90 (dd, J=8.8, 2.4 Hz, 1H), 4.42 (t, J=5.6 Hz, 2H), 3.83 (s, 3H), 3.70 (t, J=5.6 Hz, 2H), 3.40 (q, J=7.2 Hz, 2H), 2.43 (s, 3H), 1.02 (t, J=7.2 Hz, 3H); $^{13}C$ NMR (100 MHz, DMSO-$d_6$): δ 156.75, 154.17, 152.85, 148.39, 142.91, 136.73, 132.91, 128.33, 127.54, 127.15, 122.24, 122.16, 117.27, 111.37, 111.24, 110.03, 107.62, 94.53, 67.88, 65.62, 55.44, 43.41, 20.83, 14.97; HRMS (TOF MS ES$^-$): m/z calcd for $C_{24}H_{23}ClN_3O_4$ $(M-H)^-$ 452.1377, found 452.1372; mp 210° C.

Example 10: Preparation of (E)-N'-[(2-chloro-1-(2-ethoxyethyl)-5-fluoro-1H-indol-3-yl]methylene}-5-methylbenzofuran-2-carbohydrazide (CAP-1049, Compound 5)

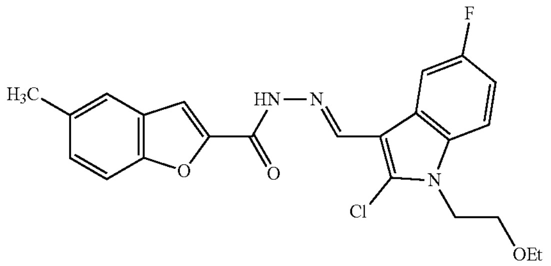 [SMILES: CCOCCn1c(Cl)c(/C=N/NC(=O)c2cc3cc(C)ccc3o2)c2cc(F)ccc21]

To 5-methylbenzofuran-2-carbohydrazide (66.6 mg, 0.35 mmol) and 2-chloro-1-(2-ethoxyethyl)-5-fluoro-1H-indol-3-carboxaldehyde (94.4 mg, 0.35 mmol), 1-PrOH (10 mL) and acetic acid (1-2 drops) were added and refluxed for 8 hours. The reaction solution was distilled under reduced pressure, dissolved in a small amount of $CH_2Cl_2$, and then added dropwise to n-Hex solution. The resulting solid was filtered to obtain 137 mg of the title compound (yield 89%, white solid).

$^1H$ NMR (400 MHz, DMSO-$d_6$): δ 12.06 (s, 1H), 8.73 (s, 1H), 8.02 (dd, J=9.6, 2.8 Hz, 1H), 7.67 (dd, J=9.2, 4.8 Hz, 1H), 7.63-7.58 (m, 3H), 7.32 (d, J=9.6 Hz, 1H), 7.18 (m, 1H), 4.47 (t, J=5.6 Hz, 2H), 3.69 (t, J=5.6 Hz, 2H), 3.38 (q, J=6.8 Hz, 2H), 2.43 (s, 3H), 0.99 (t, J=6.8 Hz, 3H); $^{13}C$ NMR (100 MHz, DMSO-$d_6$): δ 158.31 (d, J=233.8 Hz), 154.27, 152.88, 148.31, 142.49, 132.93, 132.47, 130.35, 128.37, 127.14, 123.65 (d, J=11.3 Hz), 122.24, 112.30 (d, J=9.4 Hz), 111.36, 111.21 (d, J=25.9 Hz), 110.19, 107.65 (d, J=4.4 Hz), 106.37 (d, J=25.1 Hz), 67.88, 65.64, 43.85, 20.82, 14.88; $^{19}F$ NMR (376 MHz, DMSO-$d_6$): 5-121.3 (s, 1F); HRMS (TOF MS ES$^-$): m/z calcd for $C_{23}H_{20}ClFN_3O_3$ $(M-H)^-$ 440.1177, found 440.1185; mp 187° C.

Example 11: Preparation of (E)-N'-[(2,5-dichloro-1-(2-ethoxyethyl)-1H-indol-3-yl]methylene}-5-methylbenzofuran-2-carbohydrazide (CAP-1060, Compound 9)

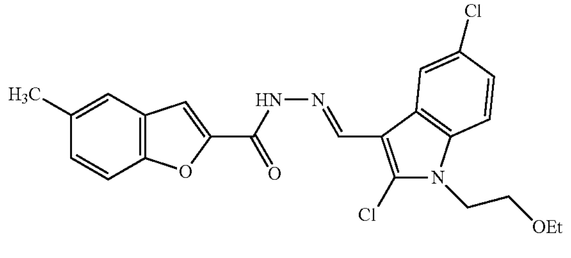

To 5-methylbenzofuran-2-carbohydrazide (165.5 mg, 0.87 mmol) and 2,5-dichloro-1-(2-ethoxyethyl)-1H-indol-3-carboxaldehyde (249.0 mg, 0.87 mmol), 1-PrOH (30 mL) and acetic acid (1-2 drops) were added and refluxed for 3 hours. The reaction solution was distilled under reduced pressure and recrystallized from EtOH. The resulting solid was filtered and washed with cold EtOH to obtain 270 mg of the title compound (yield 68%, white solid).

$^1$H NMR (400 MHz, DMSO-$d_6$): δ 12.07 (s, 1H), 8.73 (s, 1H), 8.32 (s, 1H), 7.67 (d, J=8.8 Hz, 1H), 7.63-7.58 (m, 3H), 7.35-7.31 (m, 2H), 4.46 (t, J=5.0 Hz, 2H), 3.69 (t, J=5.0 Hz, 2H), 3.38 (q, J=7.0 Hz, 2H), 2.43 (s, 3H), 0.98 (t, J=7.0 Hz, 3H); $^{13}$C NMR (100 MHz, DMSO-$d_6$): δ 154.31, 152.92, 148.30, 142.52, 134.40, 132.98, 130.52, 128.44, 127.17, 126.42, 124.25, 123.16, 122.30, 120.44, 112.65, 111.42, 110.30, 107.33, 67.89, 65.68, 43.88, 20.88, 14.93; HRMS (ESI): m/z calcd for $C_{23}H_{22}Cl_2N_3O_3$ $(M+H)^+$ 458.1038, found 458.1037; mp 98° C.

Example 12: Preparation of (E)-N'-[(2-chloro-1-(2-ethoxyethyl)-5-(trifluoromethoxy)-1H-indol-3-yl]methylene}-5-methylbenzofuran-2-carbohydrazide (CAP-1047, Compound 3)

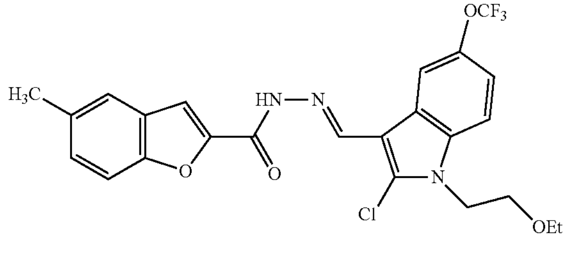 [SMILES: CCOCCn1c(Cl)c(/C=N/NC(=O)c2cc3cc(C)ccc3o2)c2cc(OC(F)(F)F)ccc21]

To 5-methylbenzofuran-2-carbohydrazide (22.8 mg, 0.12 mmol) and 2-chloro-1-(2-ethoxyethyl)-5-trifluoromethoxy-1H-indol-3-carboxaldehyde (40.3 mg, 0.12 mmol), 1-PrOH (10 mL) and acetic acid (1-2 drops) were added and refluxed for 18 hours. The reaction solution was distilled under reduced pressure, and the residue was separated by column chromatography (n-Hex:EA=1:2) to obtain 52 mg of the title compound (yield 85%, pale yellow solid).

$^1$H NMR (400 MHz, DMSO-$d_6$): δ 12.10 (s, 1H), 8.75 (s, 1H), 8.26 (s, 1H), 7.45 (d, J=9.2 Hz, 1H), 7.63-7.58 (m, 3H), 7.33-7.29 (m, 2H), 4.49 (t, J=5.2 Hz, 2H), 3.71 (t, J=5.2 Hz, 2H), 3.39 (q, J=7.2 Hz, 2H), 2.43 (s, 3H), 0.99 (t, J=7.2 Hz, 3H); $^{13}$C NMR (100 MHz, DMSO-$d_6$): δ 154.27, 152.88, 148.29, 143.57, 142.30, 134.32, 132.95, 130.87, 128.41, 127.13, 123.45, 122.27, 120.34 (q, J=253.9 Hz), 116.68, 113.47, 112.43, 111.37, 110.27, 107.92, 67.84, 65.63, 43.93, 20.83, 14.87; $^{19}$F NMR (376 MHz, DMSO-$d_6$): 5-56.8 (s, 3F); HRMS (TOF MS $ES^-$): m/z calcd for $C_{24}H_{20}ClF_3N_3O_4$ $(M-H)^-$ 506.1094, found 506.1087; mp 84-85° C.

Example 13: Preparation of (E)-N'-[(2-chloro-1-(2-ethoxyethyl)-5-methyl-1H-indol-3-yl]methylene}-5-methylbenzofuran-2-carbohydrazide (CAP-1059, Compound 8)

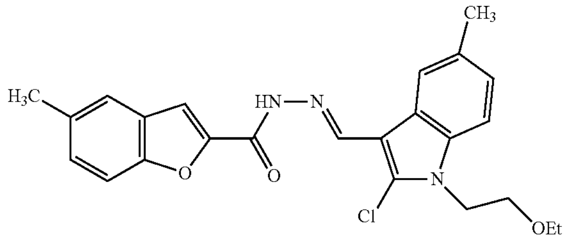 [SMILES: CCOCCn1c(Cl)c(/C=N/NC(=O)c2cc3cc(C)ccc3o2)c2cc(C)ccc21]

To 5-methylbenzofuran-2-carbohydrazide (374.7 mg, 1.97 mmol) and 2-chloro-1-(2-ethoxyethyl)-5-methyl-1H-indol-3-carboxaldehyde (523.5 mg, 1.97 mmol), 1-PrOH (30 mL) and acetic acid (1-2 drops) were added and heated to reflux for 3 hours. The reaction solution was distilled under reduced pressure and recrystallized from EtOH. The resulting solid was filtered and washed with cold EtOH to obtain 690 mg of the title compound (yield 80%, pale yellow solid).

$^1$H NMR (400 MHz, DMSO-$d_6$): δ 11.99 (s, 1H), 8.75 (s, 1H), 8.11 (s, 1H), 7.63-7.59 (m, 3H), 7.50 (d, J=8.4 Hz, 1H), 7.33 (dd, J=8.4, 1.4 Hz, 1H), 7.14 (dd, J=8.4, 1.4 Hz, 1H), 4.43 (t, J=5.4 Hz, 2H), 3.69 (t, J=5.4 Hz, 2H), 3.39 (q, J=7.0 Hz, 2H), 2.45 (s, 3H), 2.44 (s, 3H), 1.01 (t, J=7.0 Hz, 3H); $^{13}$C NMR (100 MHz, DMSO-$d_6$): δ 154.21, 152.90, 148.46, 143.38, 134.16, 132.95, 130.58, 129.22, 128.37, 127.20, 124.64, 123.54, 122.28, 121.08, 111.41, 110.42, 110.10, 107.09, 67.90, 65.66, 43.57, 21.34, 20.88, 14.95; HRMS (TOF MS $ES^-$): m/z calcd for $C_{24}H_{23}ClN_3O_3$ $(M-H)^-$ 436.1428, found 436.1442; mp 197° C.

Example 14: Preparation of (E)-N'-[(2-chloro-1-(2-ethoxyethyl)-1H-indol-3-yl]methylene}-5-methoxybenzofuran-2-carbohydrazide (CAP-1051, Compound 16)

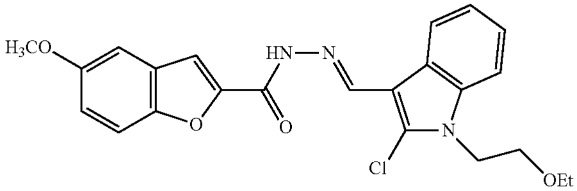 [SMILES: CCOCCn1c(Cl)c(/C=N/NC(=O)c2cc3cc(OC)ccc3o2)c2ccccc21]

To 5-methoxybenzofuran-2-carbohydrazide (103.1 mg, 0.50 mmol) and 2-chloro-1-(2-ethoxyethyl)-1H-indol-3-carboxaldehyde (125.9 mg, 0.50 mmol), 1-PrOH (15 mL) and acetic acid (1-2 drops) were added and refluxed for 7 hours. The reaction solution was distilled under reduced pressure, and the residue was washed with a mixed solvent of n-Hex/$CH_2Cl_2$ (1:1) to obtain 204 mg of the title compound (yield 93%, pale yellow solid).

$^1$H NMR (400 MHz, DMSO-$d_6$): δ 12.01 (s, 1H), 8.75 (s, 1H), 8.32 (d, J=7.6 Hz, 1H), 7.63-7.60 (m, 3H), 7.33-7.24 (m, 3H), 7.10 (dd, J=8.8, 2.4 Hz, 1H), 4.46 (t, J=5.6 Hz, 2H), 3.82 (s, 3H), 3.70 (t, J=5.6 Hz, 2H), 3.39 (q, J=7.2 Hz, 2H), 1.00 (t, J=7.2 Hz, 3H); $^{13}$C NMR (100 MHz, DMSO-$d_6$): δ 156.11, 154.16, 149.34, 148.94, 143.01, 135.76, 129.27, 127.72, 123.35, 123.21, 121.68, 121.43, 116.39, 112.47, 110.68, 110.43, 107.53, 104.20, 67.85, 65.63, 55.63, 43.53, 14.90; HRMS (TOF MS ES$^-$): m/z calcd for $C_{23}H_{21}ClN_3O_4$ $(M-H)^-$ 438.1221, found 438.1218; mp 185° C.

Example 15: Preparation of (E)-N'-[(2-chloro-1-(2-ethoxyethyl)-5-methoxy-1H-indol-3-yl]methylene}-5-methoxybenzofuran-2-carbohydrazide (CAP-1053, Compound 17)

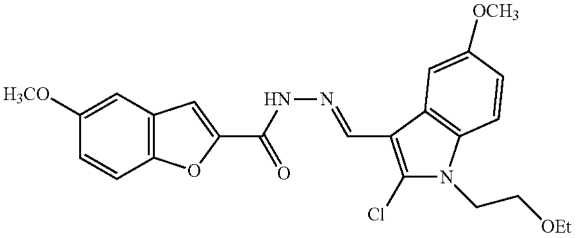 [SMILES: CCOCCn1c(Cl)c(/C=N/NC(=O)c2cc3cc(OC)ccc3o2)c2cc(OC)ccc21]

To 5-methoxybenzofuran-2-carbohydrazide (103.1 mg, 0.50 mmol) and 2-chloro-1-(2-ethoxyethyl)-5-methoxy-1H-indol-3-carboxaldehyde (140.9 mg, 0.50 mmol), 1-PrOH (15 mL) and acetic acid (1-2 drops) were added and refluxed for 8 hours. The reaction solution was distilled under reduced pressure, and the residue was separated by column chromatography (n-Hex:EA=2:3) to obtain 222 mg of the title compound (yield 94%, pale yellow solid).

$^1$H NMR (400 MHz, DMSO-$d_6$): δ 12.01 (s, 1H), 8.73 (s, 1H), 7.91 (d, J=2.4 Hz, 1H), 7.62-7.59 (m, 2H), 7.52 (d, J=8.8 Hz, 1H), 7.32 (d, J=2.4 Hz, 1H), 7.09 (dd, J=8.8, 2.4 Hz, 1H), 6.95 (dd, J=8.8, 2.4 Hz, 1H), 4.42 (t, J=5.2 Hz, 2H), 3.82 (s, 3H), 3.817 (s, 3H), 3.68 (t, J=5.2 Hz, 2H), 3.38 (q, J=7.2 Hz, 2H), 1.00 (t, J=7.2 Hz, 3H); $^{13}$C NMR (100 MHz, DMSO-$d_e$): δ 156.11, 155.21, 154.12, 149.33, 149.03, 142.97, 130.75, 128.96, 127.74, 124.02, 116.37, 112.45, 112.27, 111.54, 110.42, 107.25, 104.20, 104.09, 67.92, 65.63, 55.63, 55.33, 43.67, 14.91; HRMS (TOF MS ES$^-$): m/z calcd for $C_{24}H_{23}ClN_3O_5$ $(M-H)^-$ 468.1326, found 468.1322; mp 128-129° C.

Example 16: Preparation of (E)-5-chloro-N'-{[2-chloro-1-(2-ethoxyethyl)-1H-indol-3-yl]methylene}benzofuran-2-carbohydrazide (CAP-1062, Compound 20)

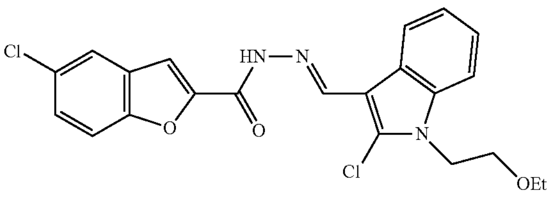 [SMILES: CCOCCn1c(Cl)c(/C=N/NC(=O)c2cc3cc(Cl)ccc3o2)c2ccccc21]

To 5-chlorobenzofuran-2-carbohydrazide (103.2 mg, 0.49 mmol) and 2-chloro-1-(2-ethoxyethyl)-1H-indol-3-carboxaldehyde (123.3 mg, 0.49 mmol), 1-PrOH (15 mL) and acetic acid (1-2 drops) were added and refluxed for 24 hours. The reaction solution was distilled under reduced pressure, and the residue was separated by column chromatography ($CH_2Cl_2$:EA=5:1) to obtain 188 mg of the title compound (yield 86%, pale yellow solid). [408]$^1$H NMR (400 MHz, DMSO-$d_6$): δ 12.10 (s, 1H), 8.75 (s, 1H), 8.32 (d, J=7.6 Hz, 1H), 7.94 (d, J=2.0 Hz, 1H), 7.76 (d, J=9.2 Hz, 1H), 7.69 (s, 1H), 7.61 (d, J=7.6 Hz, 1H), 7.53 (dd, J=9.2, 2.0 Hz, 1H), 7.33-7.24 (m, 2H), 4.46 (t, J=5.2 Hz, 2H), 3.70 (t, J=5.2 Hz, 2H), 3.39 (q, J=7.2 Hz, 2H), 1.00 (t, J=7.2 Hz, 3H); $^{13}$C NMR (100 MHz, DMSO-$d_6$): δ 153.79, 152.86, 149.68, 143.29, 135.76, 129.43, 128.66, 128.15, 126.97, 123.33, 123.23, 122.21, 121.72, 121.39, 113.52, 110.71, 109.75, 107.44, 67.84, 65.63, 43.55, 14.90; HRMS (ESI): m/z calcd for $C_{22}H_{20}Cl_2N_3O_3$ $(M+H)^+$ 444.0882, found 444.0884; mp 117° C.

Example 17: Preparation of (E)-N'-[(2-chloro-1-(2-ethoxyethyl)-1H-indol-3-yl]methylene}-4,7-dimethylbenzofuran-2-carbohydrazide (CAP-1063, Compound 21)

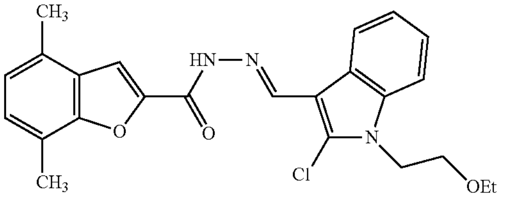 [SMILES: CCOCCn1c(Cl)c(/C=N/NC(=O)c2cc3c(C)ccc(C)c3o2)c2ccccc21]

To 4,7-dimethylbenzofuran-2-carbohydrazide (81.7 mg, 0.40 mmol) and 2-chloro-1-(2-ethoxyethyl)-1H-indol-3-carboxaldehyde (100.7 mg, 0.40 mmol), 1-PrOH (15 mL) and acetic acid (1-2 drops) were added and refluxed for 24 hours. The reaction solution was distilled under reduced pressure and separated by column chromatography ($CH_2Cl_2$:EA=5:1) to obtain 158 mg of the title compound (yield 90%, white solid).

$^1$H NMR (400 MHz, DMSO-$d_6$): δ 11.87 (s, 1H), 8.76 (s, 1H), 8.34 (d, J=7.2 Hz, 1H), 7.76 (s, 1H), 7.61 (d, J=8.0 Hz, 1H), 7.34-7.25 (m, 2H), 7.19 (d, J=8.0 Hz, 1H), 7.05 (d, J=7.2 Hz, 1H), 4.46 (t, J=5.6 Hz, 2H), 3.71 (t, J=5.6 Hz, 2H), 3.39 (q, J=7.2 Hz, 2H), 2.54 (s, 3H), 2.51 (s, 3H), 1.00 (t, J=7.2 Hz, 3H); $^{13}$C NMR (100 MHz, DMSO-$d_6$): δ 154.34, 153.35, 147.46, 142.86, 135.76, 129.60, 129.25, 127.53, 126.50, 123.81, 123.35, 123.22, 121.67, 121.42, 118.71, 110.69, 109.48, 107.50, 67.85, 65.62, 43.53, 17.88, 14.90, 14.52; HRMS (ESI): m/z calcd for $C_{24}H_{25}ClN_3O_3$ $(M+H)^+$ 438.1584, found 438.1584; mp 202° C.

Example 18: Preparation of (E)-N'-[(2-chloro-1-(2-ethoxyethyl)-1H-indol-3-yl]methylene}-4,6-dimethoxybenzofuran-2-carbohydrazide (CAP-1064, Compound 22)

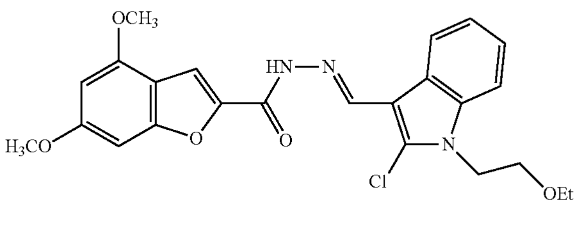 [SMILES: CCOCCn1c(Cl)c(/C=N/NC(=O)c2cc3c(OC)cc(OC)cc3o2)c2ccccc21]

To 4,6-dimethoxybenzofuran-2-carbohydrazide (118.1 mg, 0.50 mmol) and 2-chloro-1-(2-ethoxyethyl)-1H-indol-3-carboxaldehyde (125.9 mg, 0.50 mmol), 1-PrOH (15 mL) and acetic acid (1-2 drops) were added and refluxed for 4 hours. The reaction solution was cooled, and the solid was filtered and washed with EtOH to obtain 210 mg of the title compound (yield 89%, white solid).

$^1$H NMR (400 MHz, DMSO-$d_6$): δ 11.82 (s, 1H), 8.69 (s, 1H), 8.32 (d, J=7.6 Hz, 1H), 7.63 (s, 1H), 7.60 (d, J=7.6 Hz, 1H), 7.33-7.23 (m, 2H), 6.87 (s, 1H), 6.50 (d, J=2.0 Hz, 1H), 4.45 (t, J=5.6 Hz, 2H), 3.92 (s, 3H), 3.85 (s, 3H), 3.70 (t, J=5.6 Hz, 2H), 3.38 (q, J=7.2 Hz, 2H), 1.00 (t, J=7.2 Hz, 3H); $^{13}$C NMR (100 MHz, DMSO-$d_6$): δ 161.07, 156.44, 154.11, 146.03, 142.31, 135.74, 129.04, 123.33, 123.18, 121.60, 121.41, 110.98, 110.65, 107.58, 107.53, 95.13, 88.44, 67.85, 65.62, 55.84, 43.50, 14.90; HRMS (ESI): m/z calcd for $C_{24}H_{25}ClN_3O_5$ $(M+H)^+$ 470.1483, found 470.1482; mp 215° C.

Example 19: Preparation of (E)-N'-{2-[2-((2-chloro-1-(2-ethoxyethyl)-1H-indol-3-yl)methylene]hydrazine-1-carbonyl}benzofuran-5-yl)acetamide (CAP-1056, Compound 18)

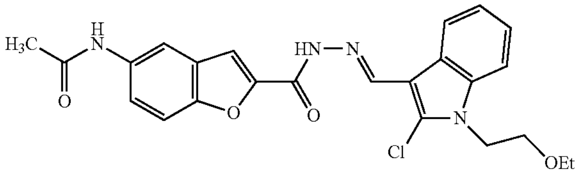 [SMILES: CCOCCn1c(Cl)c(/C=N/NC(=O)c2cc3cc(NC(C)=O)ccc3o2)c2ccccc21]

To N-((2-hydrazinecarbonyl)benzofuran-5-yl)acetamide (116.6 mg, 0.50 mmol) and 2-chloro-1-(2-ethoxyethyl)-1H-indol-3-carboxaldehyde (125.9 mg, 0.50 mmol), 1-PrOH (20 mL) and acetic acid (1-2 drops) were added and refluxed for 12 hours. The reaction solution was cooled, and the solid was filtered and washed with EtOH to obtain 166 mg of the title compound (yield 71%, pale yellow solid). [420]$^1$H NMR (400 MHz, DMSO-$d_6$): δ 12.02 (s, 1H), 10.07 (s, 1H), 8.76 (s, 1H), 8.32 (d, J=7.2 Hz, 1H), 8.17 (d, J=2.4 Hz, 1H), 7.68 (s, 1H), 7.65-7.60 (m, 2H), 7.53 (dd, J=9.2, 2.4 Hz, 1H), 7.33-7.24 (m, 2H), 4.46 (t, J=5.6 Hz, 2H), 3.70 (t, J=5.6 Hz, 2H), 3.39 (q, J=7.2 Hz, 2H), 2.08 (s, 3H), 1.00 (t, J=7.2 Hz, 3H); $^{13}$C NMR (100 MHz, DMSO-$d_6$): δ 168.24, 154.15, 150.62, 148.84, 143.08, 135.77, 135.54, 129.32, 127.18, 123.36, 123.24, 121.70, 121.44, 119.61, 112.10, 111.83, 110.72, 110.66, 107.53, 67.88, 65.65, 43.55, 23.97, 14.94; HRMS (TOF MS $ES^-$): m/z calcd for $C_{24}H_{22}ClN_4O_4$ $(M-H)^-$ 465.1330, found 465.1323; mp 226° C.

Example 20: Preparation of (E)-ethyl-2-(3-((2-(4,6-dimethoxybenzofuran-2-carbonyl)hydrazinylidene)methyl)-2-methyl-1H-indol-1-yl)acetate (CAP-1061, Compound 23)

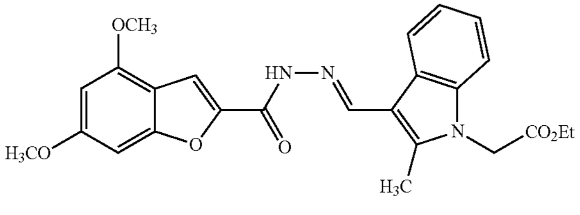 [SMILES: CCOC(=O)Cn1c(C)c(/C=N/NC(=O)c2cc3c(OC)cc(OC)cc3o2)c2ccccc21]

To 4,6-dimethoxybenzofuran-2-carbohydrazide (118.1 mg, 0.50 mmol) and ethyl 2-(3-formyl-2-methyl-1H-indol-1-yl)acetate (122.6 mg, 0.50 mmol), 1-PrOH (15 mL) and acetic acid (1-2 drops) were added and refluxed for 4 hours. The reaction solution was cooled, and the solid was filtered and washed with EtOH to obtain 197 mg of the title compound (yield 85%, white solid).

HRMS (ESI): m/z calcd for $C25H25N_3O_6Na(M+Na)$ 486.1641, found 486.1642

Example 21: Preparation of ethyl (E)-2-(2-methyl-3-((2-(5-methylbenzofuran-2-carbonyl)hydrazinylidene)methyl)-1H-indol-1-yl)acetate (CAP-1034, Compound 10)

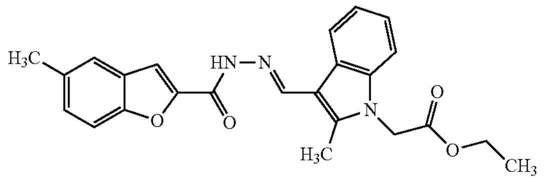 [SMILES: CCOC(=O)Cn1c(C)c(/C=N/NC(=O)c2cc3cc(C)ccc3o2)c2ccccc21]

To 5-methylbenzofuran-2-carbohydrazide (82.5 mg, 0.43 mmol) and ethyl 2-(3-formyl-2-methyl-1H-indol-1-yl)acetate (105.5 mg, 0.43 mmol), 1-PrOH (15 mL) and acetic acid (1-2 drops) were added and refluxed for 36 hours. The reaction solution was distilled under reduced pressure, and the residue was washed with $Et_2O$ to obtain 176 mg of the target compound (98%, white solid).

$^1$H NMR (400 MHz, DMSO-$d_6$) δ11.77 (s, 1H), 8.83 (s, 1H), 8.30 (m, 1H), 7.61-7.58 (m, 3H), 7.48 (m, 1H), 7.32 (d, J=8.8 Hz, 1H), 7.22-7.19 (m, 2H), 5.19 (s, 2H), 4.19 (q, J=7.2 Hz, 2H), 2.49 (s, 3H), 2.44 (s, 3H), 1.23 (t, J=7.2 Hz, 3H); $^{13}$C NMR (100 MHz, DMSO-$d_6$) δ 168.64, 153.98, 152.84, 148.71, 145.25, 141.50, 137.05, 132.92, 128.26, 127.25, 124.69, 122.27, 122.23, 121.40, 121.02, 111.37, 109.86, 109.57, 108.23, 61.24, 44.44, 20.87, 14.05, 9.98; HRMS (TOF MS $ES^-$): m/z calcd for $C_{24}H_{22}N_3O_4$ $(M-H)^-$ 416.1610, found 416.1628; mp 186° C.

Example 22: Preparation of ethyl (E)-2-(3-((2-(5-chlorobenzofuran-2-carbonyl)hydrazinylidene)methyl)-2-methyl-1H-indol-1-yl-acetate (CAP-1035, Compound 11)

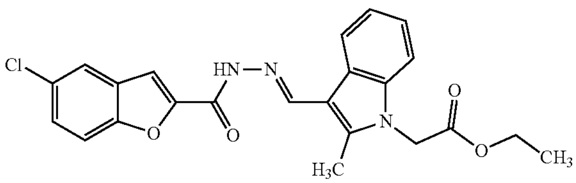 [SMILES: CCOC(=O)Cn1c(C)c(/C=N/NC(=O)c2cc3cc(Cl)ccc3o2)c2ccccc21]

To 5-chlorobenzofuran-2-carbohydrazide (105.3 mg, 0.50 mmol) and ethyl 2-(3-formyl-2-methyl-1H-indol-1-yl)acetate (122.6 mg, 0.50 mmol), 1-PrOH (15 mL) and acetic acid (1-2 drops) were added and refluxed for 24 hours. The reaction solution was cooled, and the solid was filtered and washed with EtOH to obtain 107 mg of the target compound (49%, pale yellow solid).

$^1$H NMR (400 MHz, DMSO-$d_6$) δ 11.84 (s, 1H), 8.81 (s, 1H), 8.28 (m, 1H), 7.93 (d, J=2.0 Hz, 1H), 7.76 (d, J=8.8 Hz,

1H), 7.66 (s, 1H), 7.52 (dd, J=8.8, 2.0 Hz, 1H), 7.47 (m, 1H), 7.22-7.17 (m, 2H), 5.18 (s, 2H), 4.18 (q, J=6.8 Hz, 2H), 2.49 (s, 3H), 1.23 (t, J=6.8 Hz, 3H); $^{13}C$ NMR (100 MHz, DMSO-$d_6$) δ 168.63, 153.56, 152.84, 150.01, 145.56, 141.69, 137.05, 128.76, 128.16, 126.89, 124.67, 122.31, 122.17, 121.39, 121.07, 113.51, 109.59, 109.55, 108.17, 61.25, 44.45, 14.06, 9.99; HRMS (TOF MS $ES^-$): m/z calcd for $C_{23}H1ClN_3O_4$ $(M-H)^-$ 436.1064, found 436.1062; mp 214° C.

Example 23: Preparation of methyl (E)-2-(2-chloro-3-((2-(5-methylbenzofuran-2-carbonyl)hydrazinylidene)methyl)-1H-indol-1-yl)acetate (CAP-1048, Compound 4)

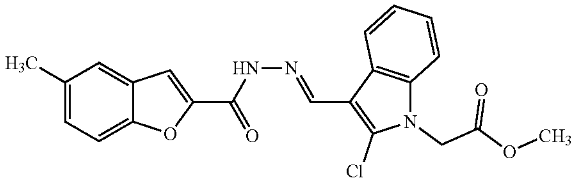

To 5-methylbenzofuran-2-carbohydrazide (319.5 mg, 1.68 mmol) and methyl 2-(2-chloro-3-formyl-1H-indol-1-yl)acetate (422.8 mg, 1.68 mmol), 1-PrOH (20 mL) and acetic acid (1-2 drops) were added and refluxed for 15 hours. The reaction solution was cooled, and the solid was filtered and washed with n-hexane to obtain 648 mg of the target compound (91%, pale yellow solid).

$^1H$ NMR (400 MHz, DMSO-$d_6$) δ 12.01 (s, 1H), 8.75 (s, 1H), 8.33 (d, J=7.5 Hz, 1H), 7.63-7.58 (m, 4H), 7.33-7.24 (m, 3H), 4.48 (s, 2H), 3.68 (s, 3H), 2.43 (s, 3H); $^{13}C$ NMR (100 MHz, DMSO-$d_6$) δ 166.12, 154.23, 152.88, 148.40, 142.97, 135.76, 132.93, 129.20, 128.36, 127.16, 123.34, 123.25, 122.25, 121.68, 121.44, 111.38, 110.68, 110.10, 107.55, 51.60, 20.84; HRMS (TOF MS $ES^-$): m/z calcd for $C_{22}H_{17}ClN_3O_4$$(M-H)^-$ 422.0908, found 422.0902; mp 212° C.

The following experiments were carried out on the Example compounds as prepared above.

<Test Example 1> Confirmation of Inhibitory Effect of NF-κB Inflammatory Response Pathway Through Cell-Based Reporter Assay The cultured human-derived HEK293 cell line was transfected with the NF-κB luciferase (reporter) vector, and treated with 10 ng/ml of TNF-α to induce activation of the NF-κB signaling pathway. In addition, during the above process, 1 uM of each of 9 kinds of compounds represented by [Chemical Formula 1] was treated to measure the inhibitory effect of the NF-κB-mediated inflammatory response regulatory pathway. Specifically, the relative expression level of NF-κB was confirmed.

As shown in FIG. 1, it was observed that in the positive control group treated only with TNF-α, the NF-κB inflammatory response pathway was activated, and the activity of the reporter was greatly increased, whereas in the case of treatment with the compounds represented by [Chemical Formula 1](in FIG. 1, represented as Compounds 1 to 9, respectively), the NF-κB activity was inhibited by 50% or more.

<Test Example 2> Confirmation of Disruption Effect of Phosphorylation of p65 (RelA) which is an Important Determinant of the NF-κB Inflammatory Response Pathway Previous studies related to the regulation of NF-κB inflammatory responses have shown that the phosphorylation process of p65 (RelA) is very important to induce an inflammatory response on the pathway. This is because phosphorylated p65 actually migrates into the nucleus of immune cells and increases the production of cytokines that cause an inflammatory response.

It was confirmed whether phosphorylation of p65 (RelA), which is the most important process in the NF-κB signaling pathway, was disrupted by culturing the same HEK293 cell line and treating the cell line with each compound.

As shown in FIG. 2, it was confirmed that all of the compounds represented by [Chemical Formula 1] of the present disclosure (In FIG. 2, indicated as compounds 1 to 9, respectively) disrupted the phosphorylation process of p65.

As shown above, it was confirmed that the compound according to the present disclosure effectively inhibited the NF-κB inflammatory response pathway, and also disrupted the phosphorylation of p65 (RelA), an important factor in the NF-κB signaling pathway, thereby exhibiting excellent anti-inflammatory efficacy.

<Test Example 3> Confirmation of Inhibitory Effect of NF-κB Inflammatory Response Pathway Through Cell-Based Reporter Assay HEK293 cell line, a human-derived embryonic kidney cell line, was cultured, transfected with NF-κB luciferase vector, treated with 1 uM of the compound, and then treated with 10 ng/ml of TNF-α to induce the NF-κB pathway. Luciferase assay method was performed to quantitatively measure the effect on NF-κB gene expression using a luminometer.

Results thereof are shown in FIG. 3.

As could be confirmed in FIG. 3, a large amount of NF-κB gene was expressed in the positive control group treated only with TNF-α. However, it was observed that the NF-κB inflammatory signaling pathway was inhibited at the time of the treatment with the compounds (indicated by CAP-No. (+"No")) of Examples according to the present disclosure.

In particular, it was confirmed in samples treated with five compounds, i.e., Example 4 (CAP-1042), Example 12 (CAP-1047), Example 10 (CAP-1049), Example 13 (CAP-1059), and Example 11 (CAP-11) 1060), that the expression amount of the NF-κB gene was significantly decreased.

<Test Example 4> Confirmation of Anti-Inflammatory Effect on Skin

3% Oxazolone (150 μl) was applied to the abdominal skin of 6-week-old mice to induce an immune response, and 0.5% diluted oxazolone (20 μl) was applied to the ears of mice a total of 5 times at intervals of one day to induce an inflammatory response. After 30 minutes of oxazolone application, Example 4 (CAP-1042) or Example 12 (CAP-1047) was applied a total of 5 times in an amount of 20 μl each at a concentration of 500 nM each.

The number of mice in each experimental group was maintained at 10 or more, and the experiment was repeated twice in total.

1. Inflammation Inhibitory Effect Confirmed with Naked Eye

As results of the above experiment, the visual results confirming inflammation inhibition and H&E staining results showing anti-inflammatory effect are shown in FIGS. 4 and 5.

Specifically, FIG. 4 shows the visual results of confirming the inflammatory changes with the naked eye. It could be appreciated that the ears of the mice applied with oxazolone alone showed red redness, indicating that the inflammatory response was well induced, compared to the ears applied with only ethanol, the solvent. On the other hand, the animal group treated with the compound of Example 4 (1042) or Example 12 (CAP-1047) showed skin conditions very similar to those of normal animals treated with ethanol.

In addition, the H&E staining results are shown in FIG. 5. When skin inflammation is induced, a pathological phenomenon called epidermal hyperplasia, in which the thickness of the entire skin and the epithelium increase together, is generally observed. It was observed that the skin to which oxazolone was applied alone had an increase in overall thickness by about two times and an increase in epithelial thickness by about three times compared to the skin to which only ethanol, a solvent, was applied. On the other hand, it was observed that when the compound of Example 4 (CAP-1042) or Example 12 (CAP-1047) was treated, the thickness of the entire skin and epithelium was reduced to the extent very similar to that of the normal skin treated with ethanol, confirming the excellent anti-inflammatory efficacy of the compounds. In particular, it could be confirmed that in view of the epithelial hyperplasia inhibitory effect, the effect was superior to that of the positive control groups.

2. Confirmation of Reduction in the Number of Inflammatory Immune Cells

When skin inflammation is induced, a pathological phenomenon in which the number of inflammatory immune cells in the entire skin is increased is generally observed.

Accordingly, in the present disclosure, the therapeutic effect of the compounds according to the present disclosure was confirmed by measuring the change in the number of inflammatory immune cells.

Specifically, after H&E staining (FIG. 5), photographs of at least 10 different parts of each sample were taken evenly under a microscope. Then, the number of inflammatory immune cells stained in dark red was directly counted from the pictures taken, and the average value was calculated.

Results thereof are shown in FIG. 6.

As could be confirmed in FIG. 6, it was observed that the skin to which oxazolone was applied alone increased the number of inflammatory immune cells by about 3 times compared to the skin to which only ethanol, a solvent, was applied. On the other hand, treatment with the compound of Example 4 (1042) or Example 7 (1047) according to the present disclosure reduced the number of immune cells induced by the inflammatory reaction to the extent very similar to that of the normal case treated with ethanol.

3. Confirmation of Reduction of Inflammatory Cytokines

After the application experiment regarding the NF-κB signaling pathway was completed, skin tissue was collected from each mouse and pulverized with a tissue crusher to extract RNA. The extracted RNA was reverse transcribed into cDNA, and then the amount of cytokines of IL-4 and IL-13 present in the skin tissue was measured by a quantitative PCR (qPCR) method using a real-time PCR machine.

Results thereof are shown in FIG. 7.

As could be appreciated in FIG. 7, it was confirmed that the amounts of interleukin-4 (IL-4) and interleukin-13 (IL-13), which are inflammatory cytokines in tissues, increased in the ears of the mice in which inflammation was induced by treatment with oxazolone alone, whereas mice treated together with oxazolone and the compound of Example 4 (1042) or Example 7 (1047) of the present disclosure had the expression level of the cytokine significantly reduced to a level of 20-25%.

It was confirmed from the above results that the compound according to the present disclosure exhibited an excellent anti-inflammatory effect.

<Test Example 5> Confirmation of Inhibition of NF-κB Canonical and Non-Canonical Inflammatory Signaling Activity and Reduction of Target Gene Expression The NF-κB signaling pathway is largely divided into canonical and non-canonical pathways. In the canonical pathway, when an inflammatory response is induced by treatment with TNF-α, the amount of P-p65 protein, which is a phosphorylated product of p65 protein, increases and migrates into the nucleus, inducing an inflammatory response. In the non-canonical pathway, when an inflammatory response is induced with a LIGHT compound that activates the non-canonical NF-κB pathway, the p100 protein is converted into p52 protein through processing and migrates into the nucleus to induce an inflammatory response.

For each of these different pathways, it was confirmed whether or not the compounds according to the present disclosure had an effect on pathway inhibition. Specifically, in order to confirm whether the activation of NF-κB signaling pathways (canonical and non-canonical pathways) is regulated, the regulation of phosphorylated p65 and p100 proteins, which are major signal regulating molecules, was confirmed using Western blotting. In the present experiment, the compound of Example 4 (1042) was used as the compound according to the present disclosure.

Results thereof are shown in FIG. 8.

As could be confirmed in FIG. 8, in the canonical pathway, when the inflammatory response was induced by treatment with TNFα, the amount of P-p65 protein, which is a phosphorylated product of p65 protein, increased and migrated into the nucleus, inducing an inflammatory response (+). In addition, when the inflammatory response was induced with the LIGHT compound, the p100 protein was converted into p52 protein through processing and migrated into the nucleus to induce an inflammatory response (+). TPCA1, which is known to act on the p65 protein, acts on the canonical pathway, but not on the non-canonical pathway.

On the other hand, the compound according to the present disclosure acted as a dual inhibitor that inhibits both the canonical and non-canonical pathways of the NF-κB inflammatory signaling pathway, and exhibited excellent pathway inhibitory effects in both pathways.

It was confirmed from the above results that the compounds according to the present disclosure exhibited an effect as a dual inhibitor that inhibits both the canonical and non-canonical pathways of the NF-κB inflammatory signaling pathway.

<Test Example 6> Confirmation of Selective Binding of Compounds to IKKa and Inhibition of Structure Formation In order to confirm the mechanism of NF-κB activity regulation, an experiment was performed to determine whether the bindings to NF-κB key regulatory molecules were achieved by binding biotin to the drug (Example 4). Specifically, the bindings to IKKa, IKK3, IKKγ, p65, and IκBα related to canonical and/or non-canonical pathways were confirmed.

Results thereof are shown in FIG. 9.

As could be confirmed in FIG. 9, it was confirmed that the compound of the present disclosure selectively bound to IKKa specifically among the NF-κB key regulatory molecules.

IKKα is in the form of a hexamer (6mer), that is, 6 monomers combine to mediate the NF-κB signaling pathway.

Thus, the compound according to the present disclosure (Example 4) was treated to determine whether the active form of hexamer was generated, and results thereof are shown in FIG. 10.

As could be confirmed in FIG. 10, it was confirmed that the treatment with the compounds of Examples according to the present disclosure inhibited the formation of hexamer IKKa and acted as a selective inhibitor for IKKa.

<Test Example 7> Confirmation of Cytokine Storm Suppression and Sepsis Treatment Effect Using Sepsis Model Since there were no disease model animals leading to death from a cytokine storm caused by coronaviruses, particularly Sars-Cov2, the present inventors used an acute sepsis model in which an acute inflammatory response is induced to cause the cytokine storm problem and confirmed inhibition of the cytokine storm, the possibility of treating severe acute respiratory syndrome coronavirus 2 infection disease and the possibility of treating sepsis.

An experiment was performed by treating LPS on an animal model (cytokine storm-like model) of sepsis (death). The experimental design is shown in FIG. 11A. Mice were intraperitoneally administered with LPS for induction of sepsis and injected intravenously with the drug (Example 4), and then blood was collected at 3, 6, and 12 hours. The survival rate was confirmed for 48 hours to observe mortality due to sepsis.

The survival rate after 48 hours was confirmed, and as a result, the administration of the compound of Example 4 according to the present disclosure significantly reduced mortality due to sepsis, as could be confirmed in FIG. 11B.

In addition, as could be confirmed in FIG. 11C, the compounds of the present disclosure were excellent in inhibiting cytokine and chemokine production.

It was confirmed through the above results that the compounds of Examples according to the present disclosure inhibited the expression of cytokines and chemokines in the body, thereby reducing mortality due to sepsis, and inhibiting an acute inflammatory reaction, in particular, a cytokine storm phenomenon.

The invention claimed is:

1. A method for treating dermatitis, comprising administering to a subject in need thereof an effective amount of compounds selected from the group consisting of the following compounds, a stereoisomer thereof, or a pharmaceutically acceptable salt thereof:

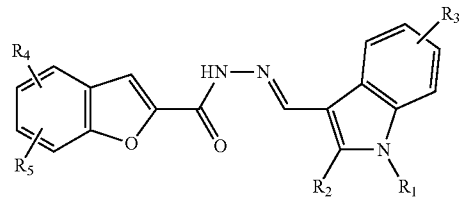

(E)-N'-[(2-chloro-1H-indol-3-yl)methylene]-5-methylbenzofuran-2-carbohydrazide;

(E)-N'-[(2-chloro-1-(2-ethoxyethyl)-1H-indol-3-yl]methylene}-5-methylbenzofuran-2-carbohydrazide;

(E)-N'-[(2-chloro-1-(2-ethoxyethyl)-5-methoxy-1H-indol-3-yl]methylene}-5-methylbenzofuran-2-carbohydrazide;

(E)-N'-[(2-chloro-1-(2-ethoxyethyl)-6-methoxy-1H-indol-3-yl]methylene}-5-methylbenzofuran-2-carbohydrazide;

(E)-N'-[(2-chloro-1-(2-ethoxyethyl)-5-fluoro-1H-indol-3-yl]methylene}-5-methylbenzofuran-2-carbohydrazide;

(E)-N'-{[2,5-dichloro-1-(2-ethoxyethyl)-1H-indol-3-yl] methylene}-5-methylbenzofuran-2-carbohydrazide;

(E)-N'-{[2-chloro-1-(2-ethoxyethyl)-5-(trifluoromethoxy)-1H-indol-3-yl]methylene}-5-methylbenzofuran-2-carbohydrazide;

(E)-N'-[(2-chloro-1-(2-ethoxyethyl)-5-methyl-1H-indol-3-yl]methylene}-5-methylbenzofuran-2-carbohydrazide; and methyl (E)-2-(2-chloro-3-((2-(5-methylbenzofuran-2-carbonyl)hydrazinylidene)methyl)-1H-indol-1-yl)acetate, wherein the dermatitis is any one or more selected from the group consisting of atopic dermatitis, contact dermatitis, allergic dermatitis, psoriasis, and pruritus.

2. The method of claim 1, wherein the administering is oral administration or parenteral administration.

3. The method of claim 2, wherein the parenteral administration is any one selected from the group consist of transdermal administration, skin external use, intraperitoneal injection, intrarectal injection, subcutaneous injection, intravenous injection, intramuscular injection, and intrathoracic injection.

* * * * *